(12) United States Patent
Duggan

(10) Patent No.: US 11,053,202 B2
(45) Date of Patent: Jul. 6, 2021

(54) COMPOSITIONS FOR THE TREATMENT OF HYPERTENSION AND/OR FIBROSIS

(71) Applicant: Vectus Biosystems Limited, New South Wales (AU)

(72) Inventor: Karen Annette Duggan, New South Wales (AU)

(73) Assignee: Vectus Biosystems Limited, New South Wales (AU)

( * ) Notice: Subject to any disclaimer, the term of this patent is extended or adjusted under 35 U.S.C. 154(b) by 0 days.

(21) Appl. No.: 16/334,283

(22) PCT Filed: Sep. 21, 2017

(86) PCT No.: PCT/AU2017/051027
§ 371 (c)(1),
(2) Date: Mar. 18, 2019

(87) PCT Pub. No.: WO2018/053588
PCT Pub. Date: Mar. 29, 2018

(65) Prior Publication Data
US 2019/0225588 A1   Jul. 25, 2019
US 2020/0255384 A9   Aug. 13, 2020

Related U.S. Application Data

(63) Continuation of application No. PCT/AU2017/051027, filed on Sep. 21, 2017.

(30) Foreign Application Priority Data

Sep. 21, 2016 (AU) .................. 2016903804

(51) Int. Cl.
| C07D 233/64 | (2006.01) |
| C07D 241/04 | (2006.01) |
| A61P 9/00 | (2006.01) |
| A61P 13/12 | (2006.01) |
| A61P 11/00 | (2006.01) |
| C07D 233/90 | (2006.01) |
| C07D 401/06 | (2006.01) |
| C07D 401/04 | (2006.01) |
| C07D 401/12 | (2006.01) |
| C07D 403/04 | (2006.01) |
| C07D 417/04 | (2006.01) |
| C07D 413/04 | (2006.01) |
| C07D 413/06 | (2006.01) |
| C07D 403/06 | (2006.01) |
| C07D 407/04 | (2006.01) |
| C07D 417/06 | (2006.01) |
| C07D 407/06 | (2006.01) |
| C07D 409/06 | (2006.01) |
| C07D 409/04 | (2006.01) |
| A61P 1/16 | (2006.01) |
| A61P 9/12 | (2006.01) |

(52) U.S. Cl.
CPC .............. *C07D 233/64* (2013.01); *A61P 1/16* (2018.01); *A61P 9/00* (2018.01); *A61P 9/12* (2018.01); *A61P 11/00* (2018.01); *A61P 13/12* (2018.01); *C07D 233/90* (2013.01); *C07D 241/04* (2013.01); *C07D 401/04* (2013.01); *C07D 401/06* (2013.01); *C07D 401/12* (2013.01); *C07D 403/04* (2013.01); *C07D 403/06* (2013.01); *C07D 407/04* (2013.01); *C07D 407/06* (2013.01); *C07D 409/04* (2013.01); *C07D 409/06* (2013.01); *C07D 413/04* (2013.01); *C07D 413/06* (2013.01); *C07D 417/04* (2013.01); *C07D 417/06* (2013.01)

(58) Field of Classification Search
CPC .................................................... C07D 233/64
See application file for complete search history.

(56) References Cited

U.S. PATENT DOCUMENTS

| 5,492,912 A | 2/1996 | Godfroid et al. |
| 2011/0092703 A1 | 4/2011 | Sakuma et al. |
| 2011/0130382 A1 | 6/2011 | Wang et al. |

FOREIGN PATENT DOCUMENTS

| EP | 1 661 898 A1 | 5/2006 |
| FR | 2759698 A1 | 2/1997 |
| JP | 2001-294572 A | 10/2001 |
| WO | WO95/25443 | * 3/1995 |
| WO | WO 1995/025443 A1 | 9/1995 |
| WO | WO 2003/015784 | 2/2003 |
| WO | WO 2007/006688 A1 | 1/2007 |
| WO | WO2007/094513 | * 8/2007 |
| WO | WO 2007/094513 A2 | 8/2007 |
| WO | WO 2008/154241 A1 | 12/2008 |
| WO | WO 2009/021868 A2 | 2/2009 |
| WO | WO2009021868 | * 2/2009 |
| WO | WO 2012/064631 A1 | 5/2012 |
| WO | WO 2014/00533 A1 | 6/2014 |
| WO | WO 2016/105448 A1 | 6/2016 |

OTHER PUBLICATIONS

CAS Registry No. 1269070-79-2 entered Mar. 21, 2011.
CAS Registry No. 1269086-34-1 entered Mar. 21, 2011.
CAS Registry No. 1269240-72-3 entered Mar. 21, 2011.
CAS Registry No. 1269245-54-6 entered Mar. 21, 2011.
International Search Report issued in International Application No. PCT/AU2014/051027 dated Jan. 5, 2018.
Xi et al., "Regio-controlled Synthesis of N-Substituted Imidazoles," *Tetrahedron Letters* 46:7315-7319 (2005).
Supplementary Partial European Search Report dated Aug. 13, 2019 in European Patent Appln. No. 17851990.6.

(Continued)

*Primary Examiner* — Paul V Ward
(74) *Attorney, Agent, or Firm* — Arnold & Porter Kaye Scholer

(57) ABSTRACT

The present invention relates to novel compounds and their use in the prophylactic and/or therapeutic treatment of hypertension and/or fibrosis.

13 Claims, 7 Drawing Sheets

(56) References Cited

OTHER PUBLICATIONS

CAS Registry No. 1432059-68-1 entered May 23, 2013.
CAS Registry No. 1432056-94-4 entered May 23, 2013.
CAS Registry No. 1394470-81-5 entered May 23, 2013.
CAS Registry No. 1394469-05-6 entered May 23, 2013.
CAS Registry No. 1378176-21-6 entered May 23, 2013.
Holl et al., "Homologous piperazine-Alcanols: chiral pool synthesis and pharmacological evaluation," *Med. Chem. Commun.* 3:673-679 (2012).
European Search Report dated Jan. 22, 2020 in European Appln. No. 19212378.4.

* cited by examiner

COMPOSITIONS FOR THE TREATMENT OF HYPERTENSION AND/OR FIBROSIS

FIELD OF THE INVENTION

The present application claims priority from Australian Provisional Patent Application No. 2016903804 (filed 21 Sep. 2016), the contents of which are incorporated in their entirety herein.

The present invention relates to novel compounds and their use in the prophylactic and/or therapeutic treatment of cardiovascular disease, and in particular the treatment of prehypertension, hypertension and/or fibrotic conditions.

The invention has been developed primarily for the prophylactic and/or therapeutic treatment of cardiovascular disease and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Hypertension (high blood pressure) affects 26% of the adult population worldwide with an incidence of 30-33% in western countries. The world wide incidence of hypertension is expected to reach 29% by 2025 as a consequence of the westernisation of India and China. Current studies indicate that fewer than 20% of patients with hypertension attain their recommended blood pressure (BP) target and that to achieve these targets >75% of patients require therapy with multiple antihypertensive agents. Prehypertension (slightly elevated blood pressure) affects 31% of adults in the US and may develop into hypertension if not treated.

Hypertension and prehypertension are a major factor in the development of blood vessel damage in a variety of organs, resulting in the replacement of normal functional tissue by scar tissue or fibrosis. Some of the current antihypertensive agents are able to slow the progression of the replacement of functional tissue by fibrosis, but none have been shown to reverse existing fibrosis and restore normal tissue architecture. There is thus a need for agents which have the efficacy to reduce BP significantly and thus enable a larger proportion of patients to attain BP target with single agent therapy and/or to reverse existing fibrosis and/or restore normal tissue architecture.

It is an object of the present invention to overcome or ameliorate at least one of the disadvantages of the prior art, or to provide a useful alternative.

SUMMARY OF THE INVENTION

Surprisingly, the present inventors have found that certain compounds have blood pressure lowering and/or anti-fibrotic effects. These effects may be seen in intravenous and/or oral dosing studies.

According to one aspect, the present invention provides a compound of the formulae:

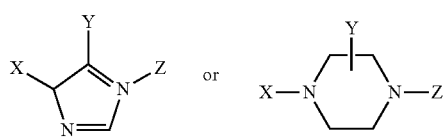

wherein:

X is selected from the group consisting of:

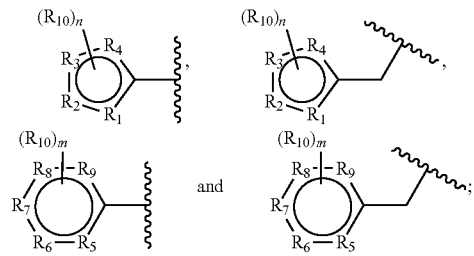

$R_1$ to $R_9$ are independently C, N, O or S;

$R_{10}$ is independently selected from $C_{1-6}$alkyl, halo, $C_{0-6}$alkyl carboxylic acid, amino, hydroxy and $C_{1-6}$alkoxy;

Y is A, $CH_2$-A or CH=A;

A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl;

Z is selected from the group consisting of:

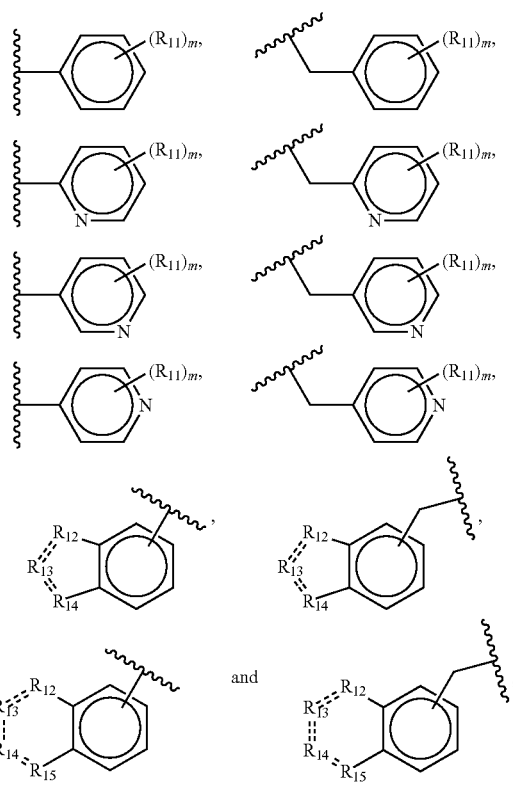

$R_{11}$ is independently selected from halo, alkyl, hydroxy, amino and substituted amino;

$R_{12}$, $R_{14}$ and $R_{15}$ are independently C, CH, $CH_2$, O, N, NH or S;

$R_{13}$ is C, CH, CH$_2$, N, NH, C—CF$_3$, CH—CF$_3$ or C=O;
m is 0, 1, 2, 3, 4 or 5; and
n is 0, 1, 2, 3 or 4,
or a stereoisomer or pharmaceutically acceptable salt thereof.

In one embodiment, $R_{10}$ is independently selected from —CH$_3$, —C(O)OH, —F, —NH$_2$, —OH and —OCH$_3$.

In one embodiment, $R_5$ to $R_9$ are independently C or N.

In one embodiment, the C$_{0-6}$alkyl carboxylic acid is carboxylic acid.

In one embodiment, the saturated, partly saturated or unsaturated 5- or 6-membered heterocyclyl contains one or more of N, S or O, optionally substituted with one or more oxo, C$_{1-6}$alkyl, amino, hydroxyl or halo substituents.

In one embodiment, the saturated, partly saturated or unsaturated 5- or 6-membered heterocyclyl is selected from pyrrolyl, pyrazolyl, imidazolyl, triazolyl, imidazolidinyl, pyrrolidinyl, pyrrolidinylidene, dihydropyrrolyl, isoxazolyl dihydrooxazolyl, isoxazolidinyl, oxazolidinyl and oxazolyl, optionally substituted with one or more oxo, C$_{1-6}$alkyl, amino, hydroxyl or halo substituents.

In one embodiment, the C$_{1-6}$alkoxyl amine is aminooxymethyl.

In one embodiment, the C$_{1-6}$alkyl amine is optionally substituted with one or more of C$_{1-6}$alkyl, C$_{1-6}$halo alkyl, hydroxyl or halo, preferably mono-, di- or tri-substituted halo alkyl, most preferably tri-fluoro methane.

In one embodiment, the C$_{1-6}$alkyl hydroxyl is methyl hydroxyl or propan-2-ol.

In one embodiment, the C$_{0-6}$alkyl bicyclic heterocyclyl is selected from indolyl, isoindolyl, insolinyl and isoindolinyl, optionally substituted with one or more oxo, preferably dioxo.

In one embodiment, the C$_{1-6}$alkoxyl bicyclic heterocyclyl is selected indolyl, isoindolyl, insolinyl and isoindolinyl, optionally substituted with one or more oxo, and wherein the C$_{1-6}$alkoxyl is methoxy or ethoxy.

In one embodiment, A is selected from:

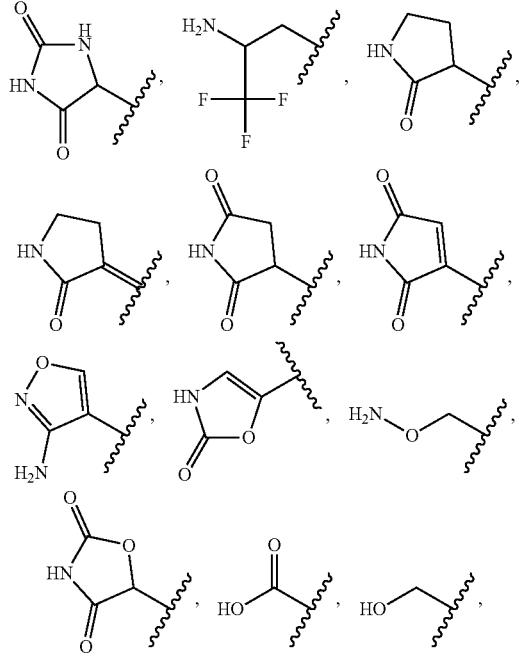

-continued

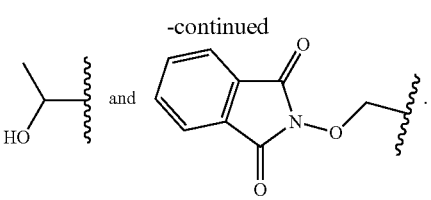

In one embodiment, $R_{11}$ is halo selected from the group consisting of F, Cl, Br and I.

In one embodiment, $R_{11}$ is substituted amino of the formula —NHR$_{16}$ and wherein:

$R_{16}$ is selected from —CN, —SO$_2$(R$_{17}$)$_a$R$_{18}$ and —CO(R$_{17}$)$_a$R$_{18}$,
a is 0 or 1,
$R_{17}$ is selected from —NH— and —O—, and
$R_{18}$ is selected from —H, —CH$_3$, —CH$_2$CH$_3$, —CH$_2$OH and —CH$_2$CH$_2$OH.

In one embodiment, $R_{11}$ is substituted amino selected from the group consisting of —NHSO$_2$CH$_3$, —NHCOH, —NHCONHCH$_3$, —NHCONHCH$_2$CH$_3$, —NHSO$_2$NHCH$_3$, —NHSO$_2$NHCH$_2$CH$_3$, —NHCOCH$_3$, —NHCOOCH$_3$, —NHCOOCH$_2$CH$_2$OH, —NHCONH$_2$ and —NHCN.

In one embodiment, $R_{11}$ is alkyl selected from the group consisting of methyl, ethyl, propyl, butyl and pentyl.

In one embodiment, the compound is selected from the group consisting of:

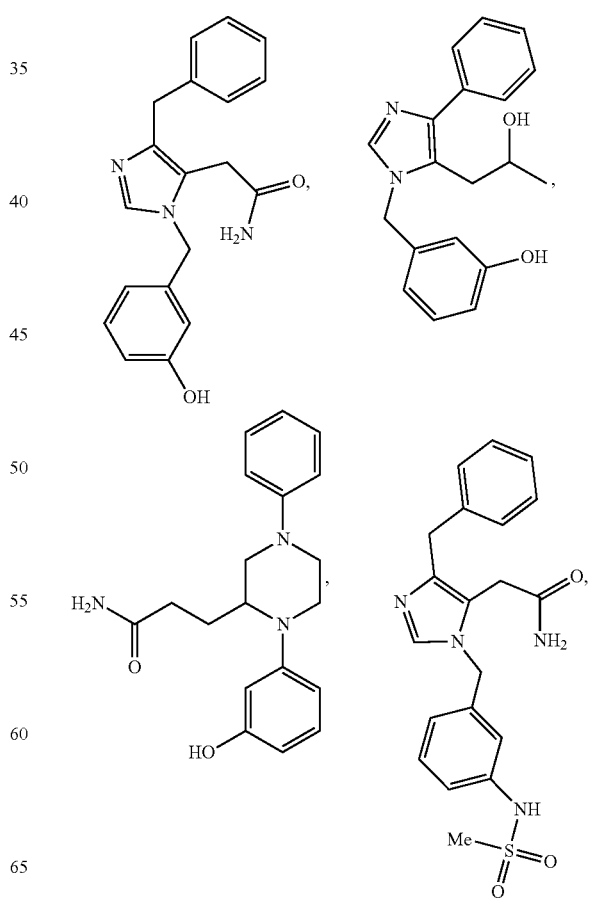

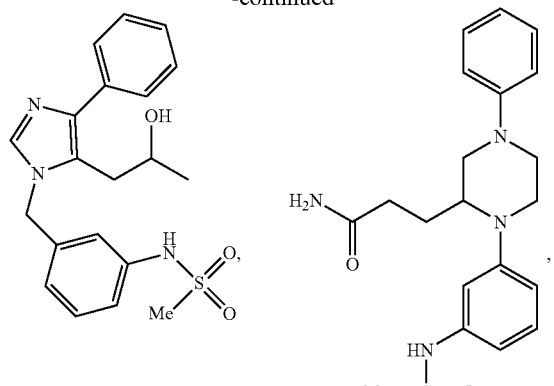
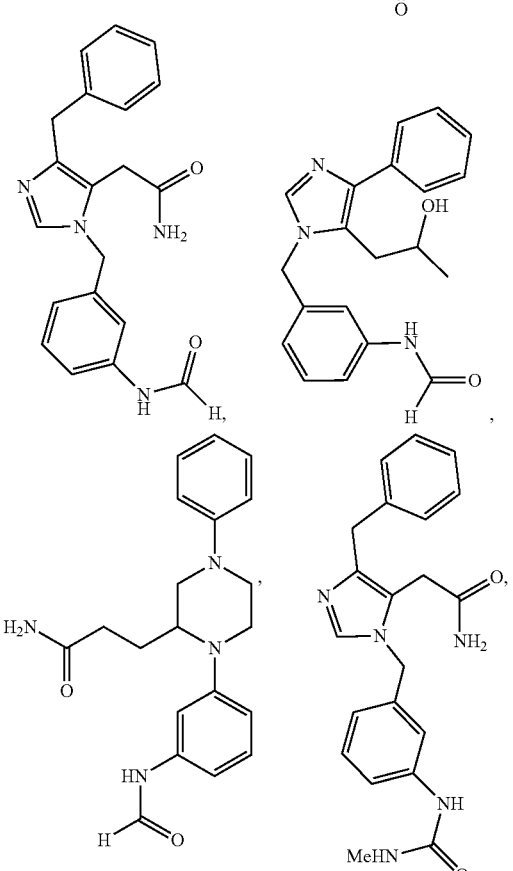
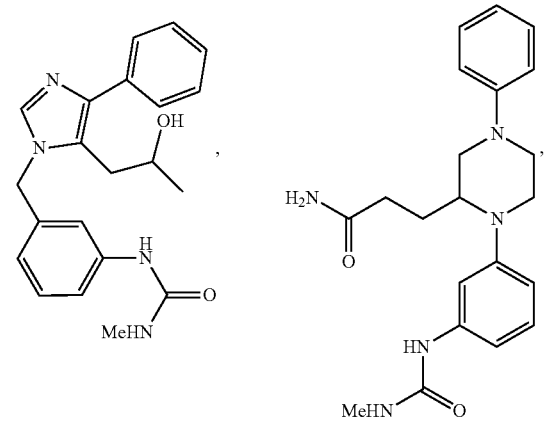
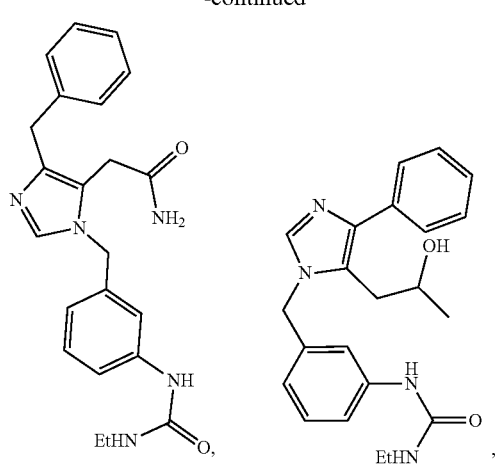
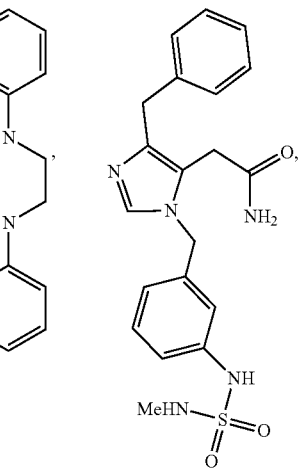
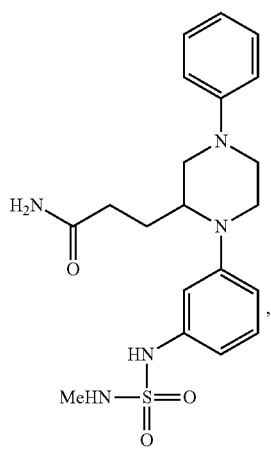

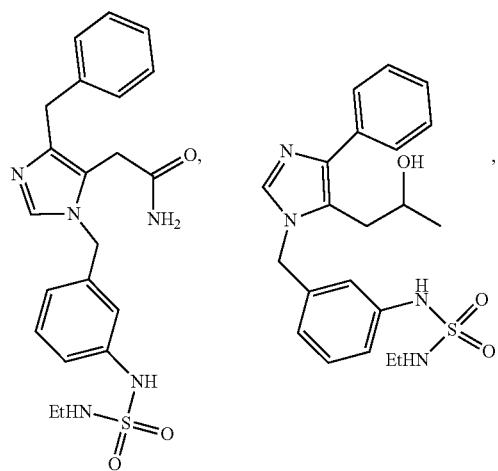
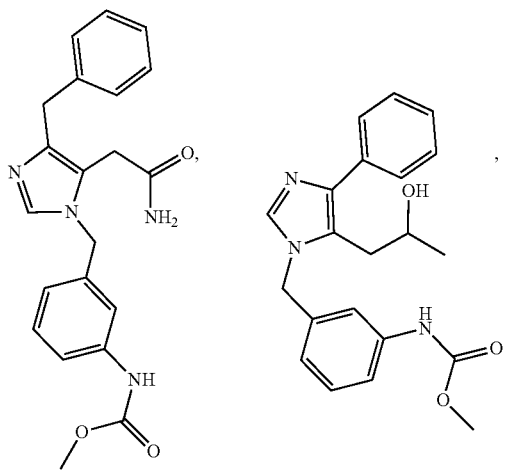
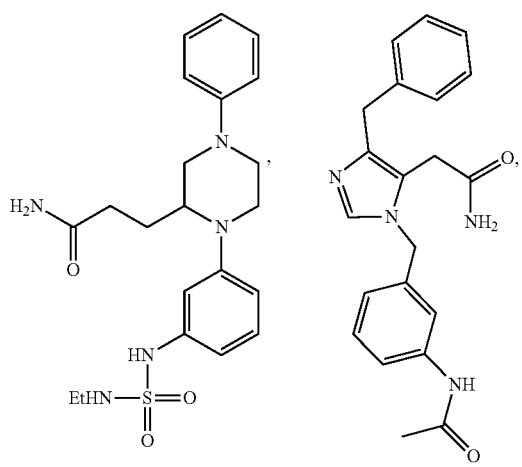
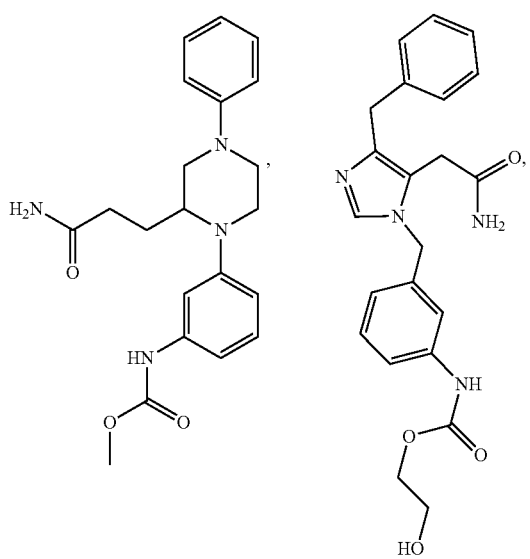
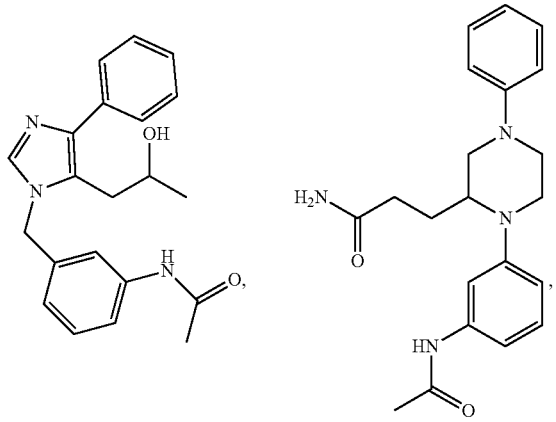
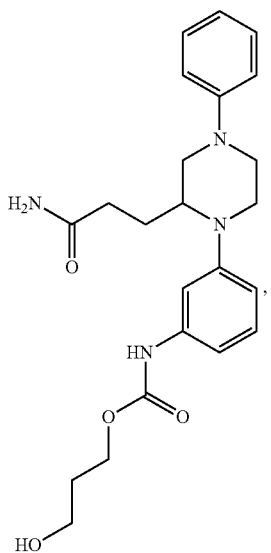

-continued
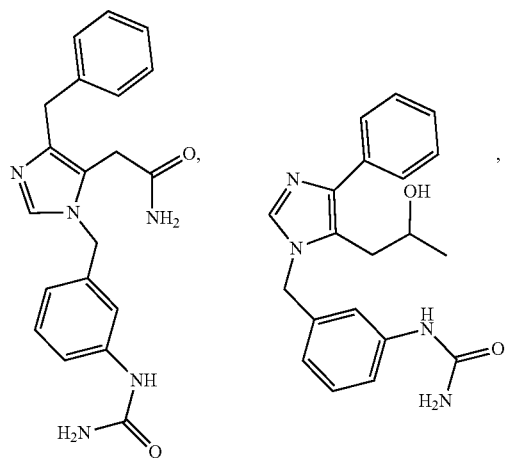
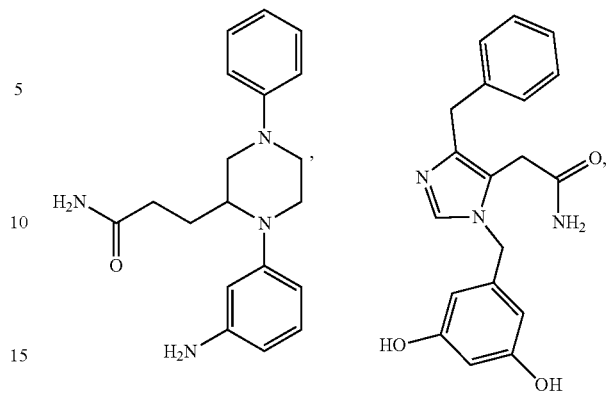

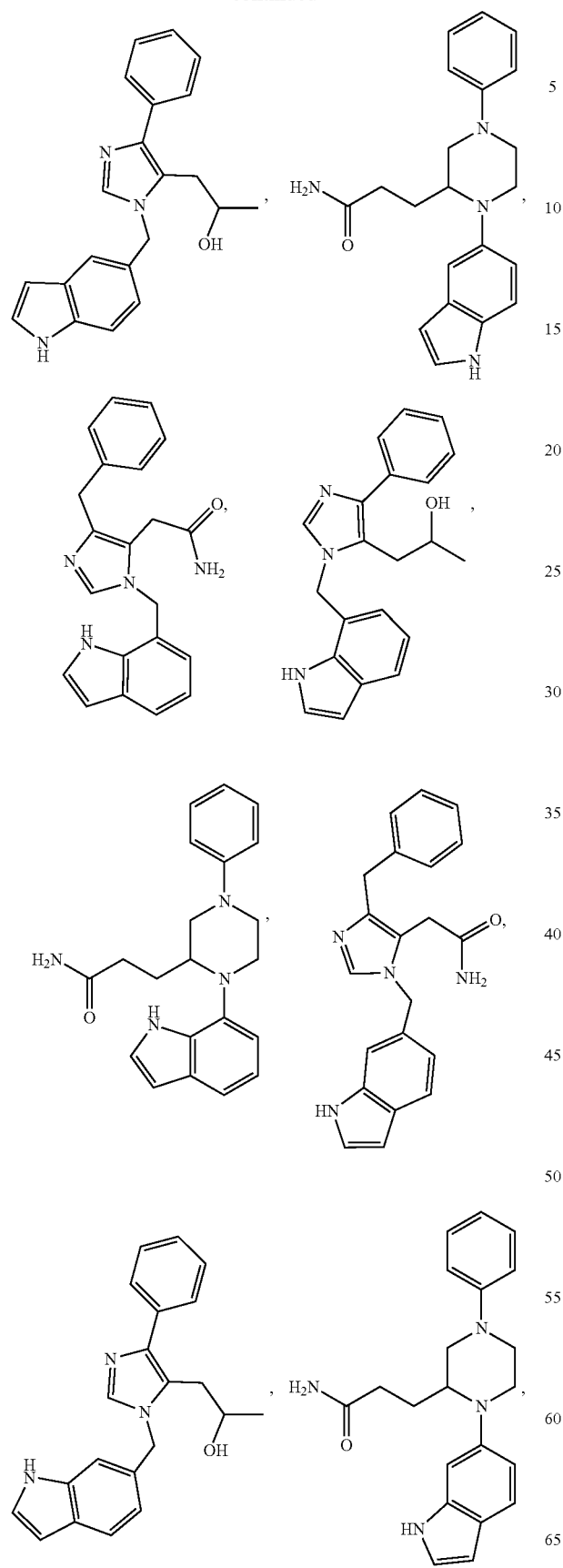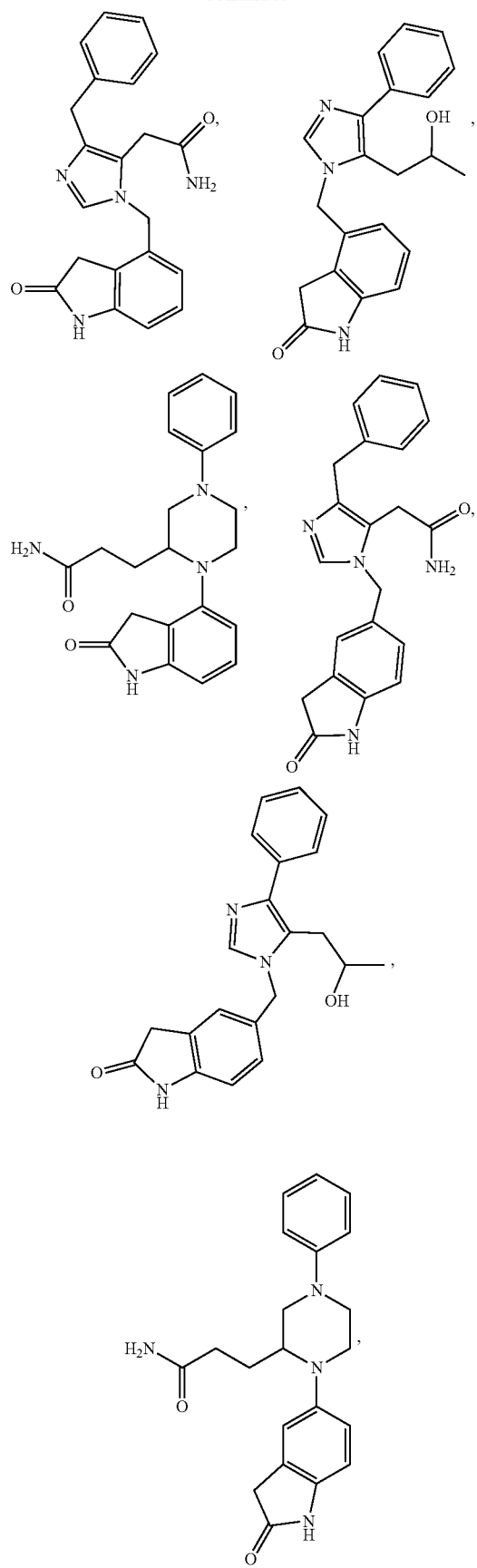

13
-continued
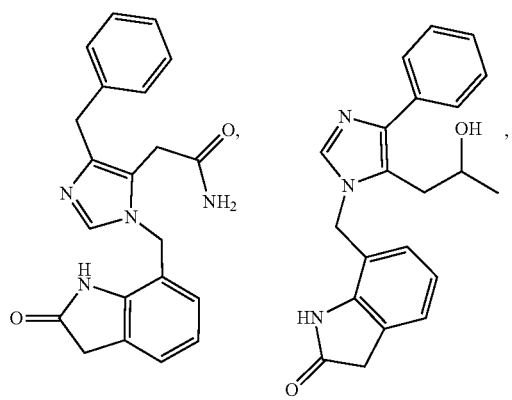
14
-continued
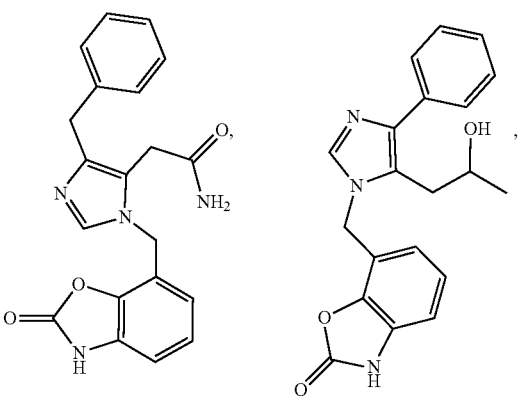
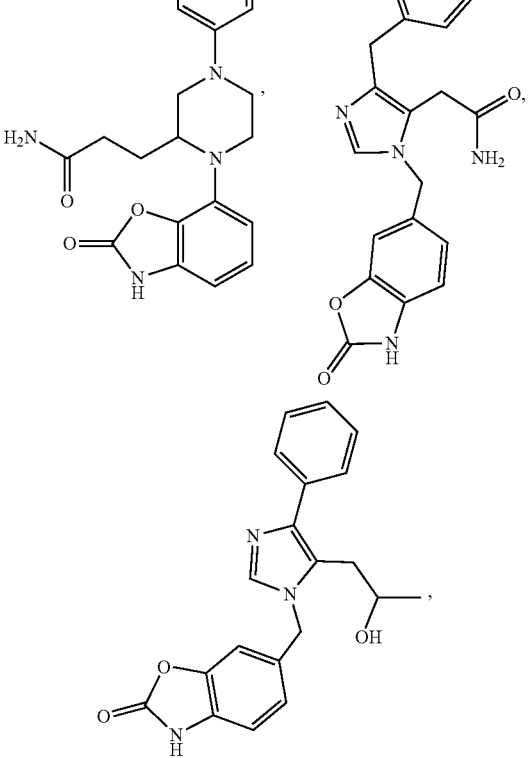
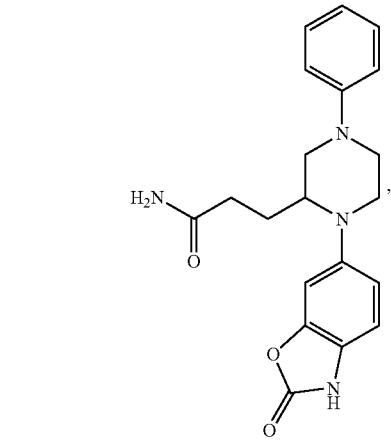

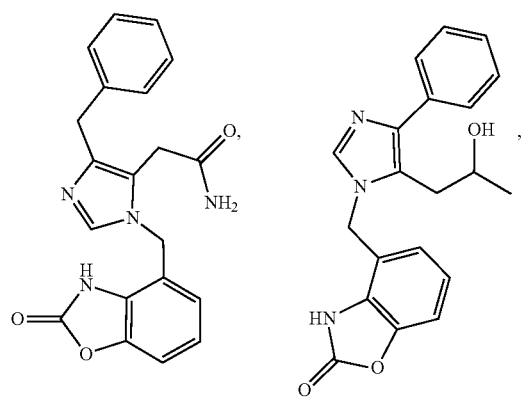
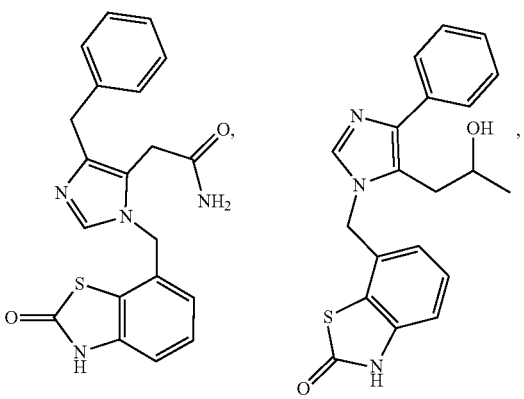
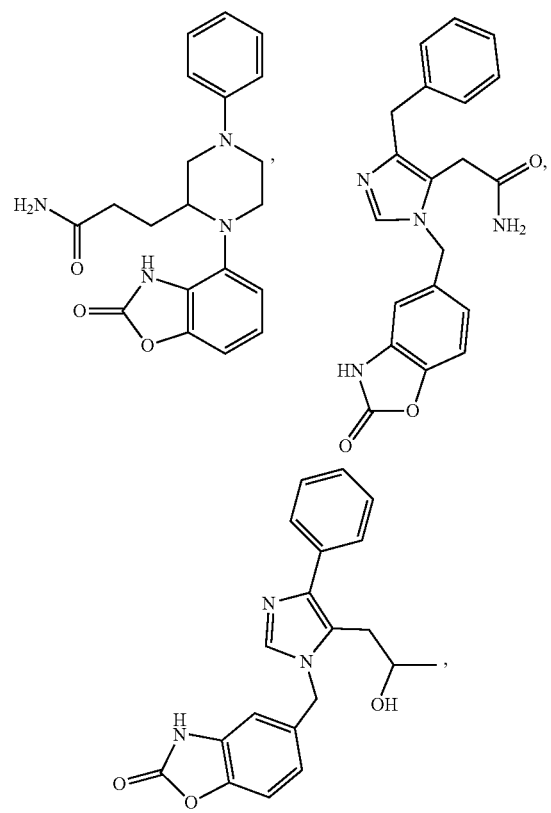
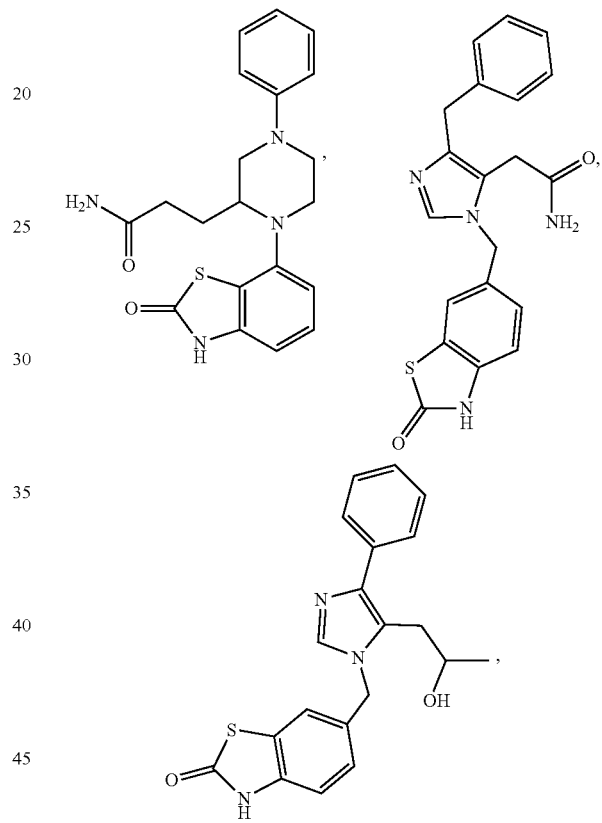
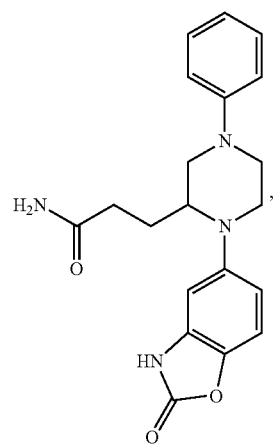
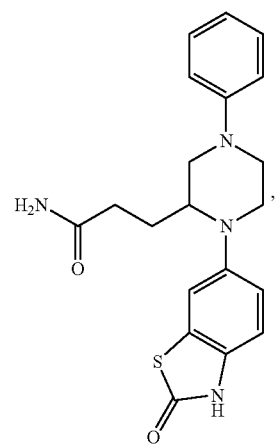

-continued
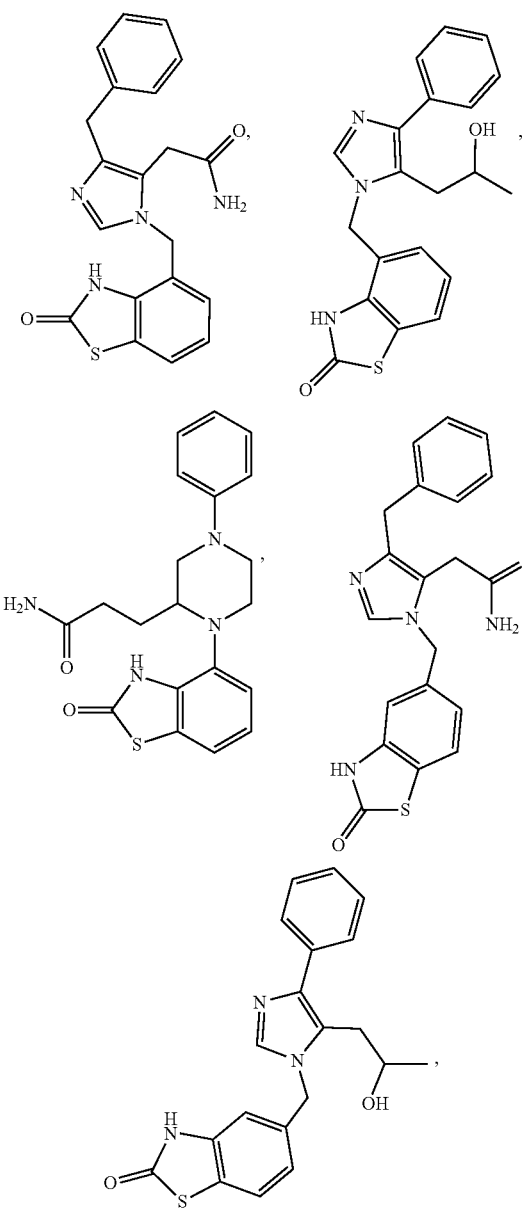
-continued
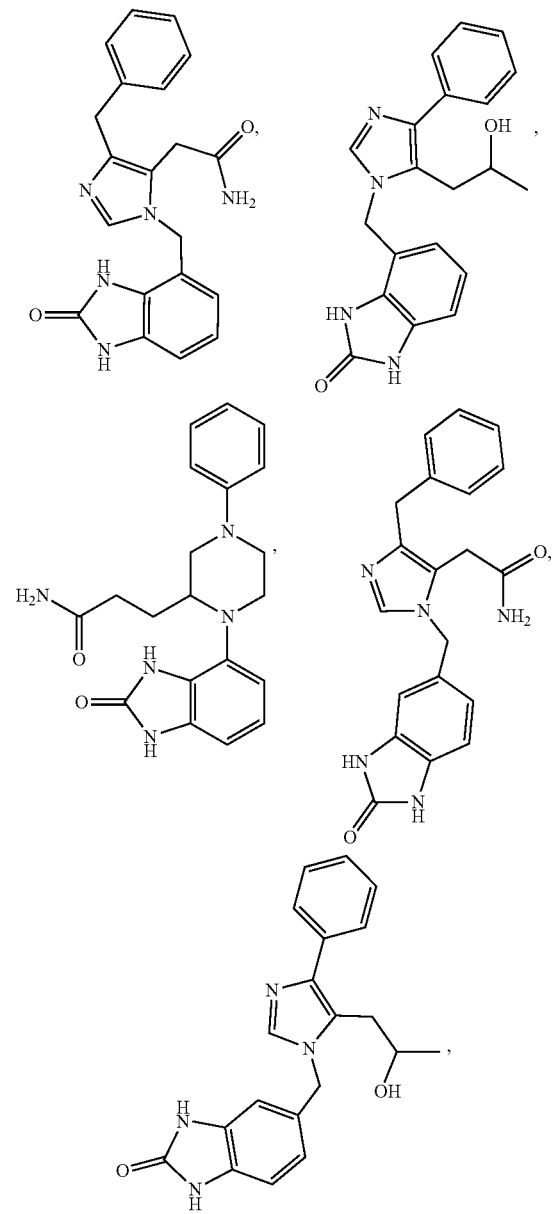
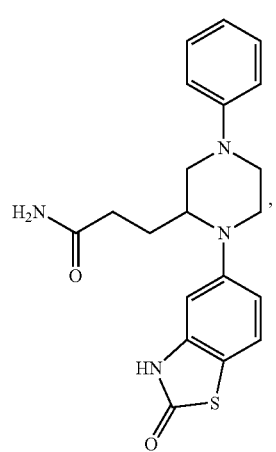

19
-continued
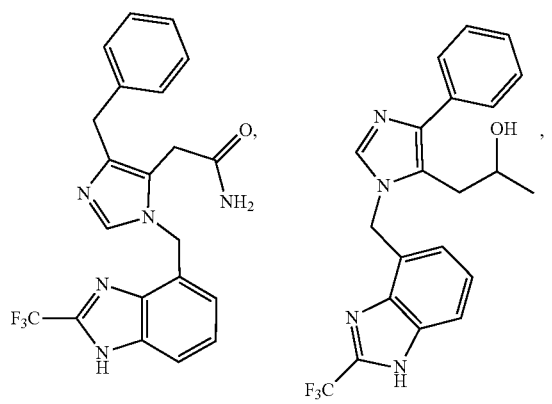
20
-continued
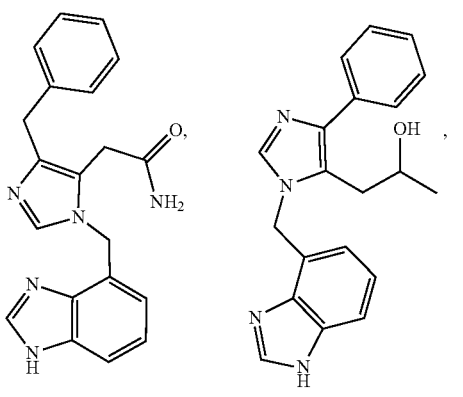
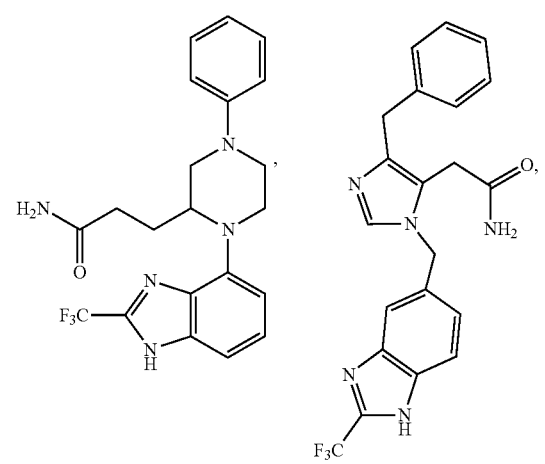
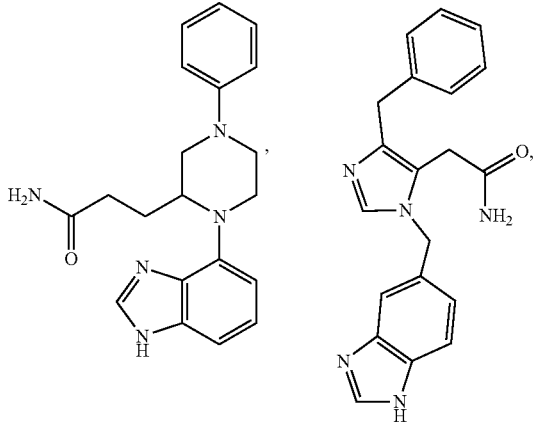
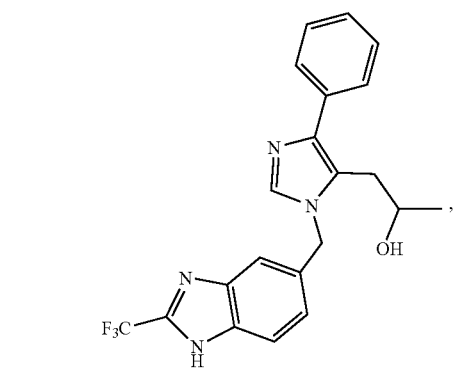
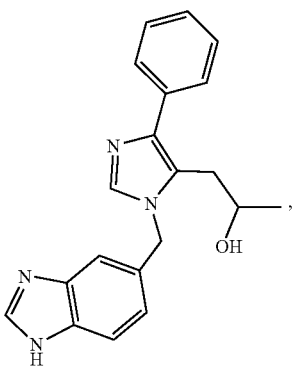
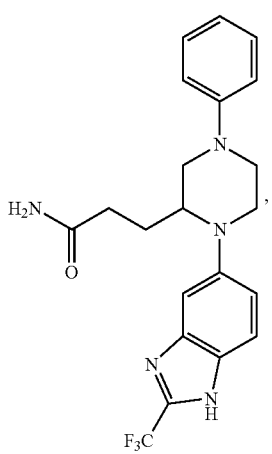

21
-continued
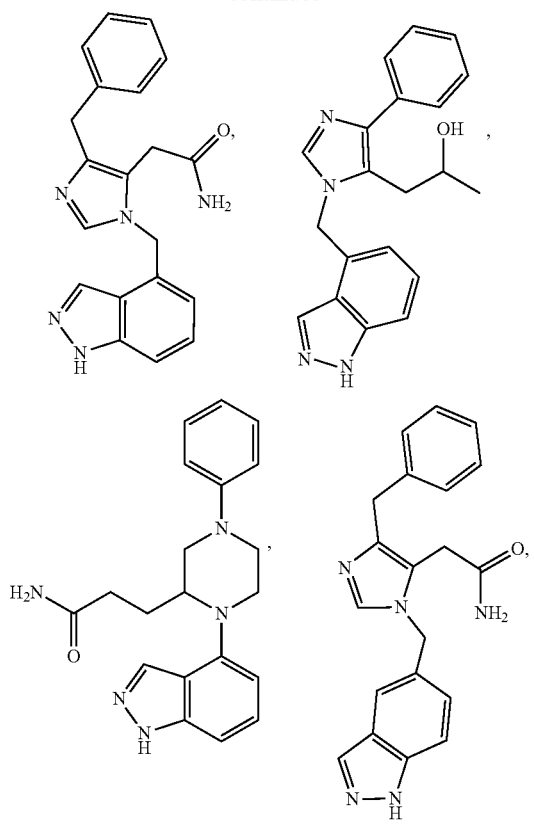
22
-continued
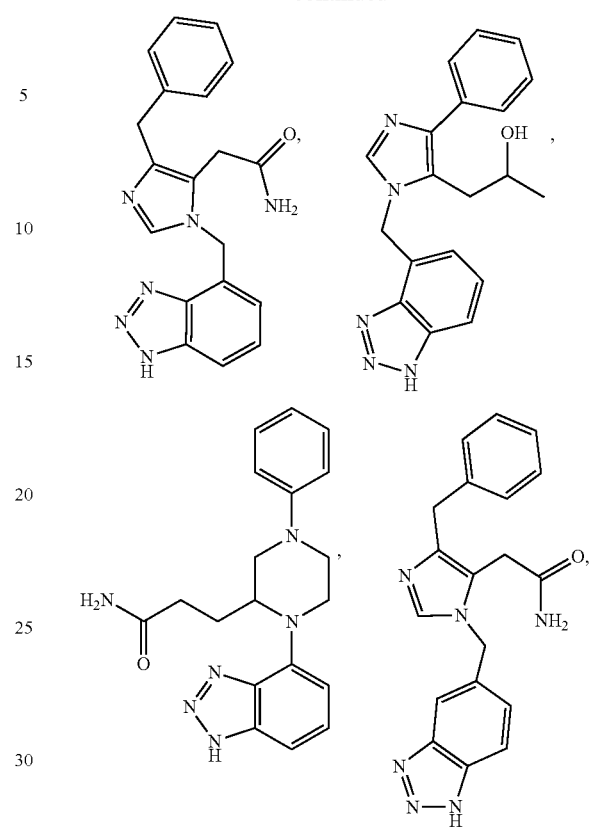
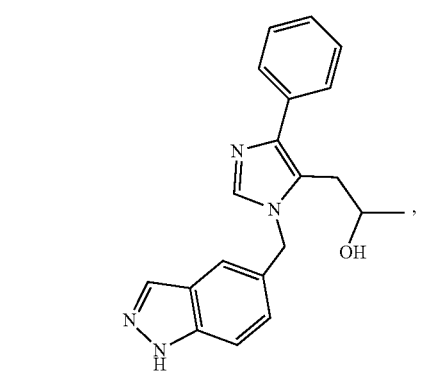
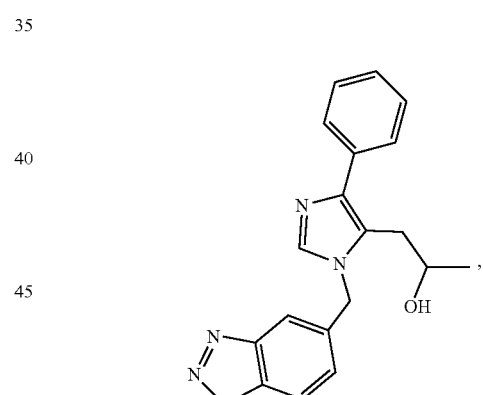
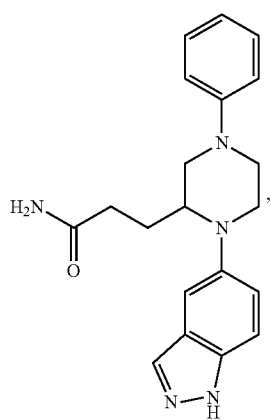
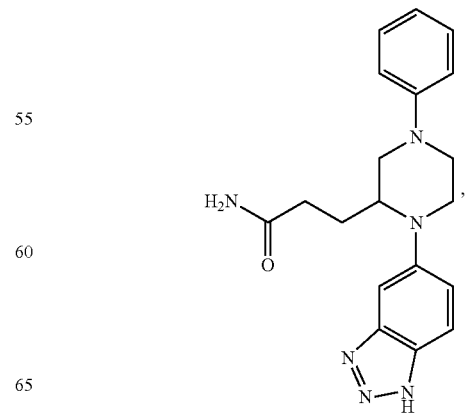

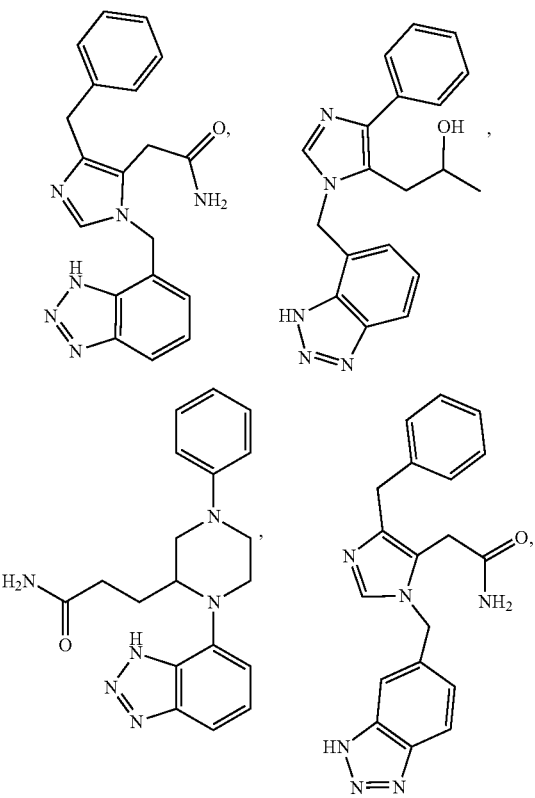
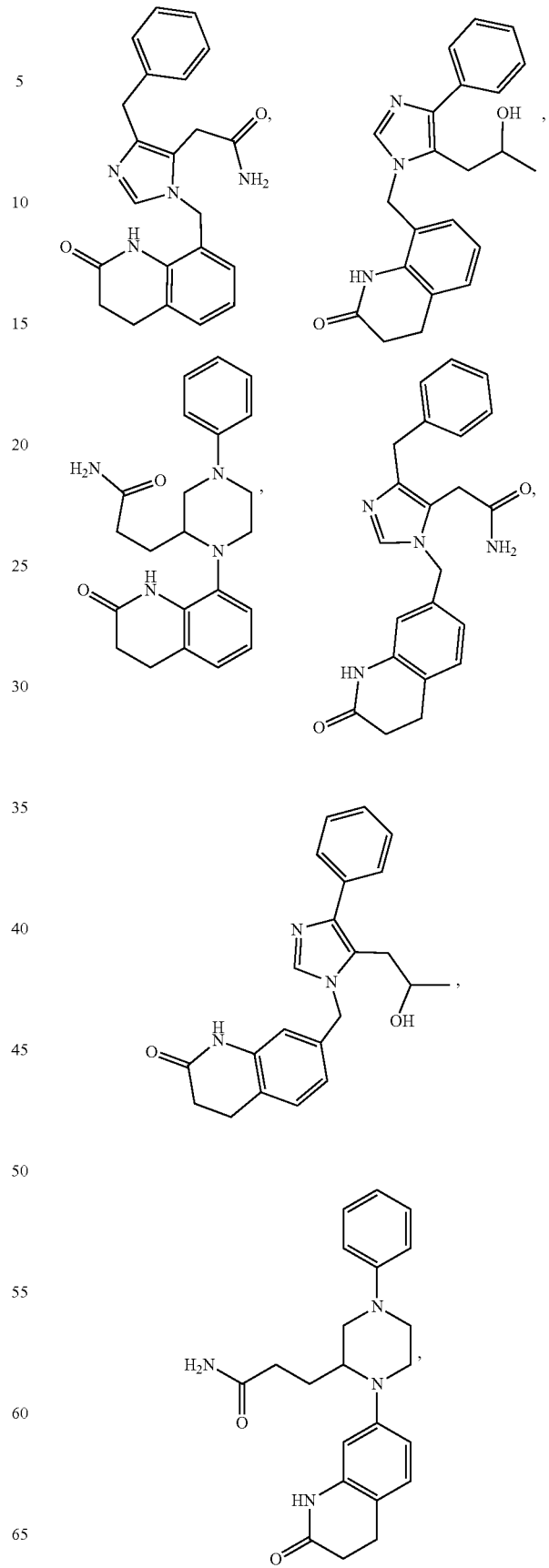

25
-continued
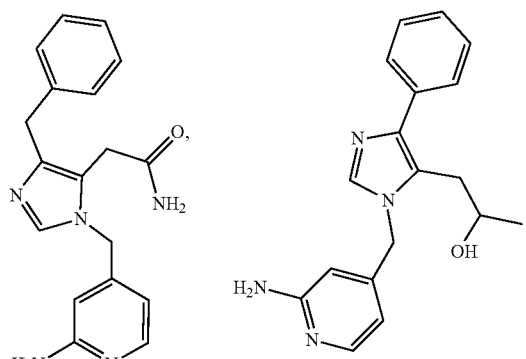
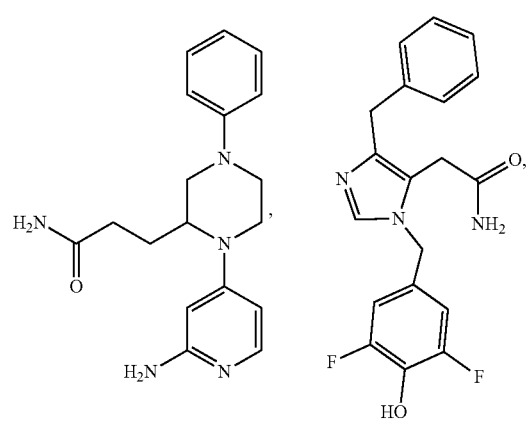
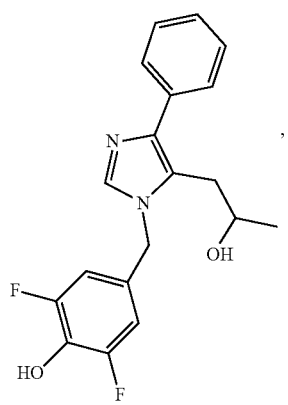
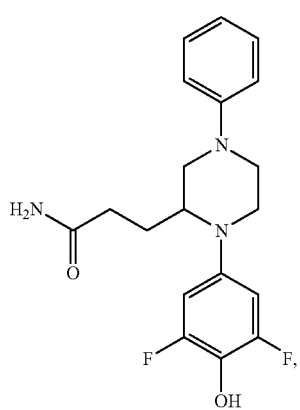
26
-continued
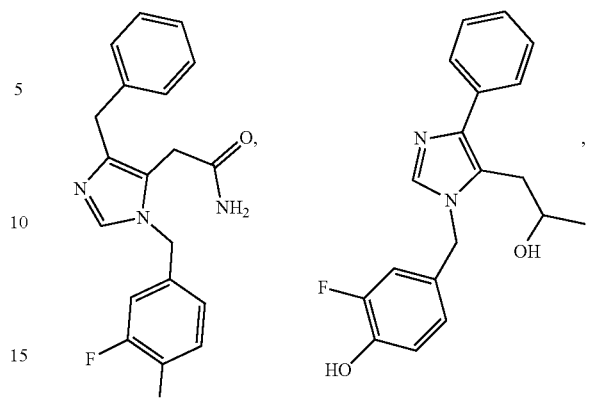
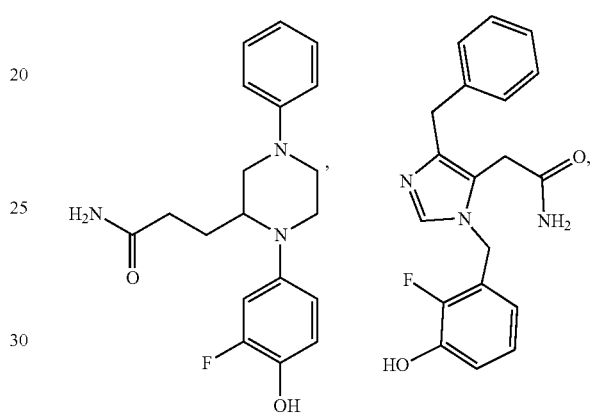
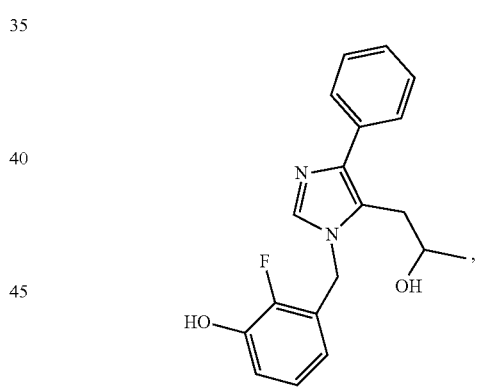
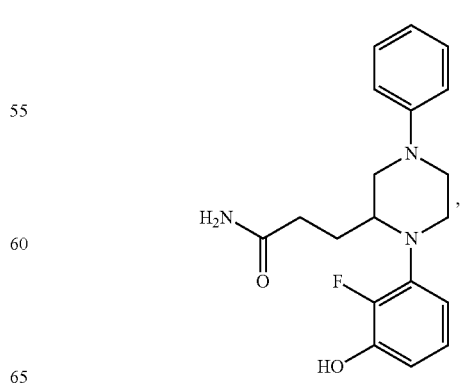

27
-continued
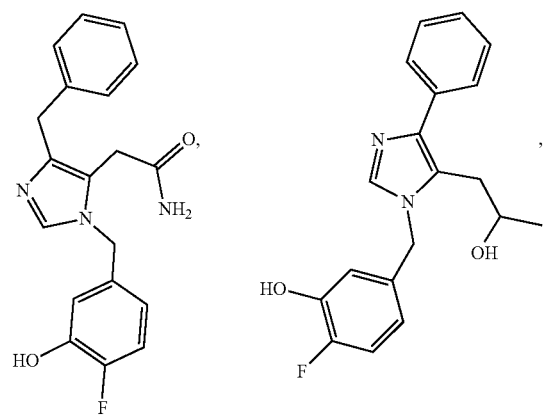
28
-continued
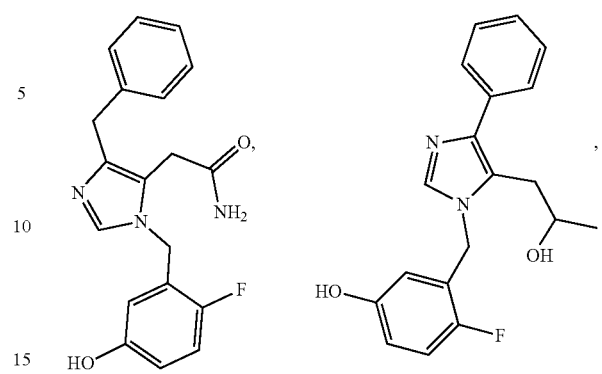
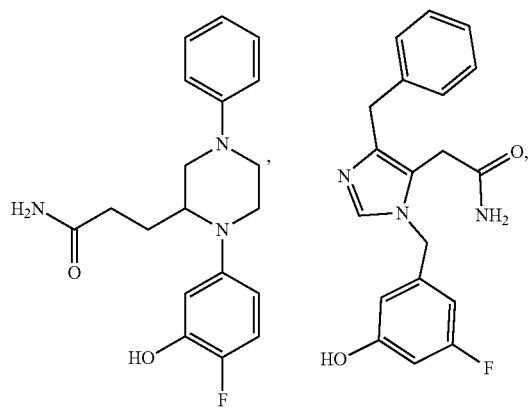
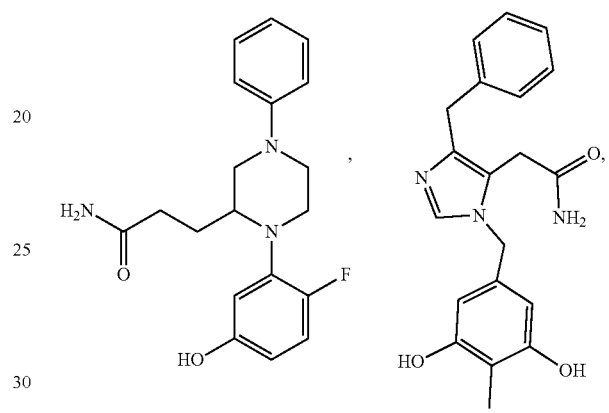
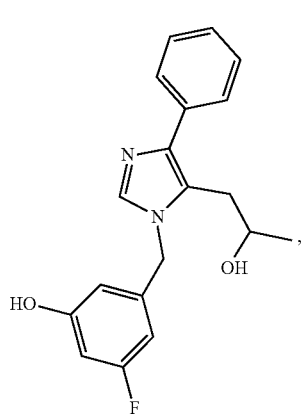
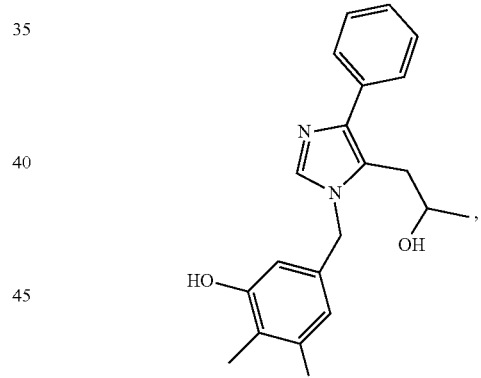
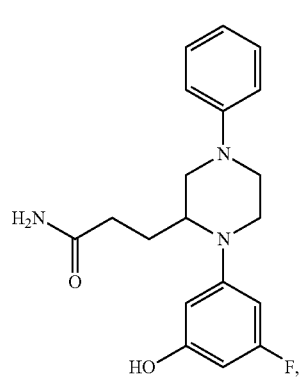
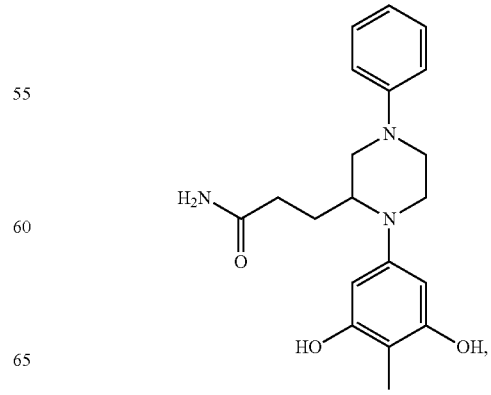

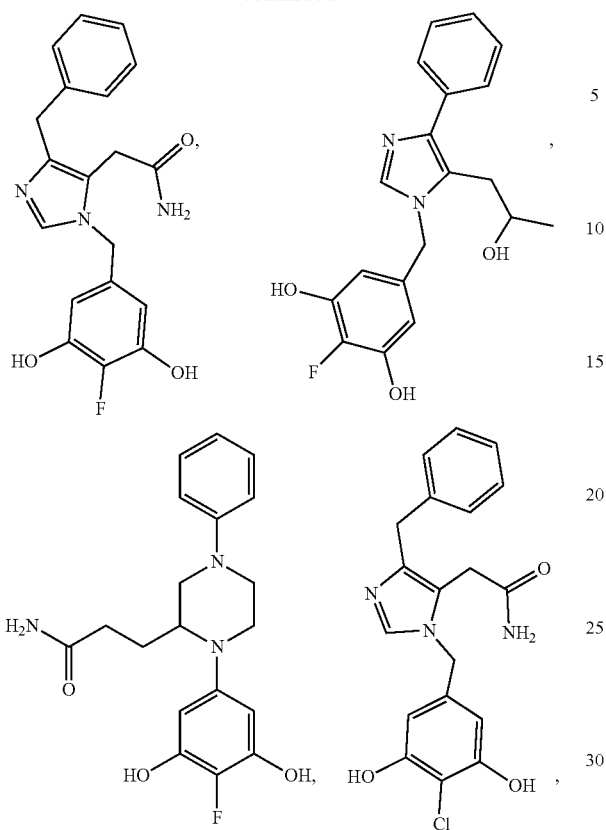
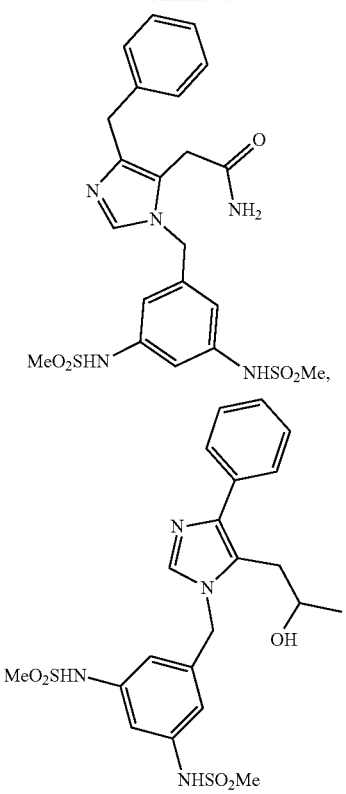
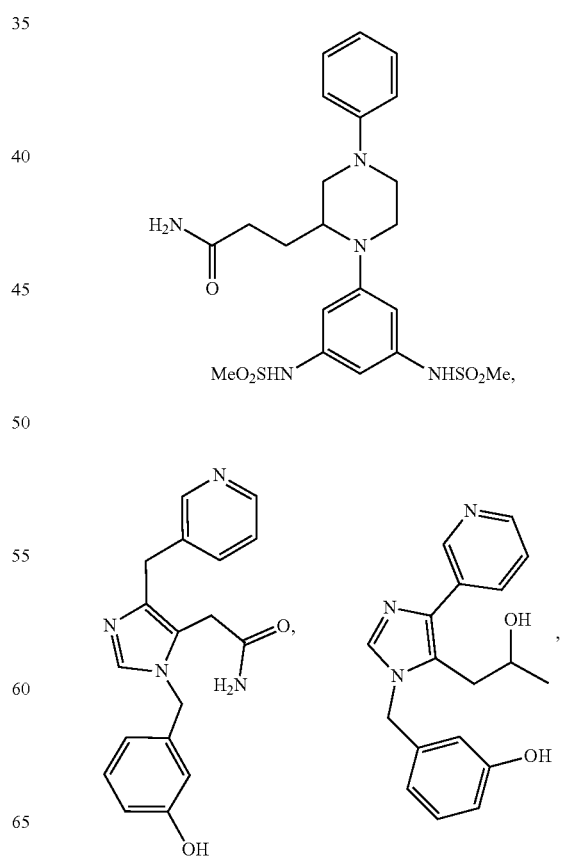

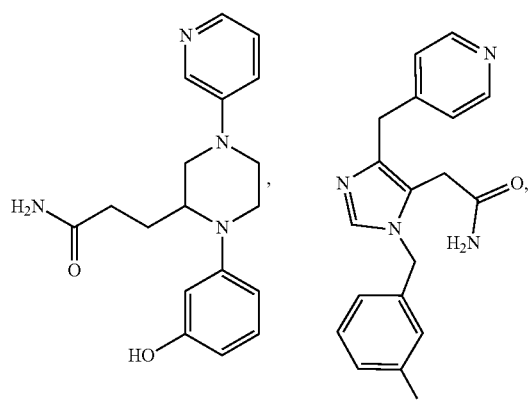
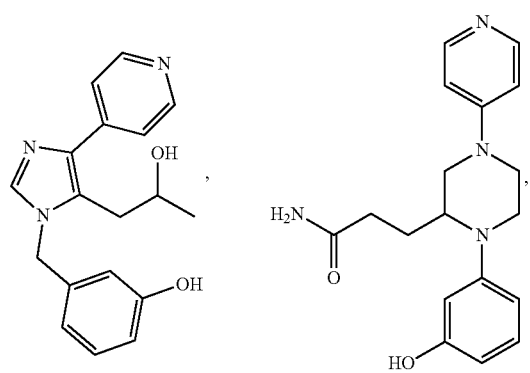
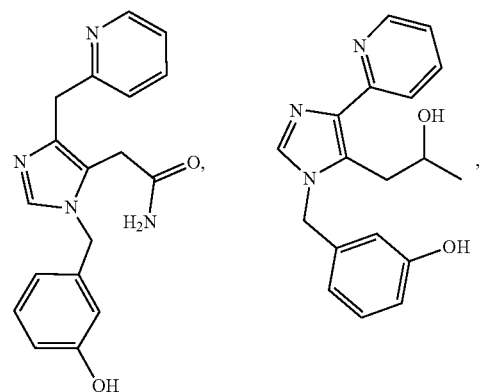
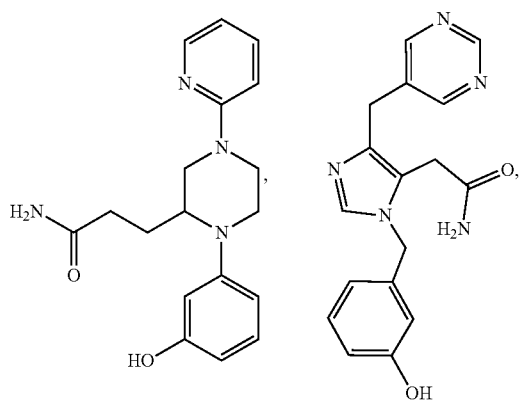
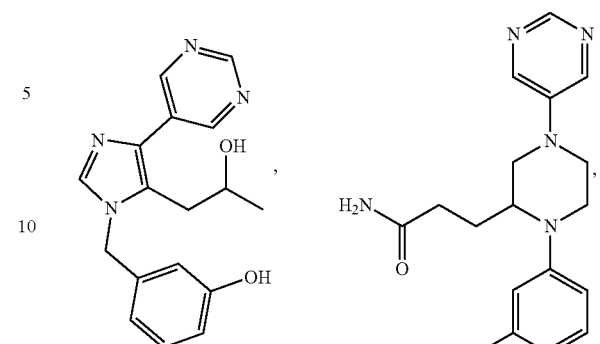
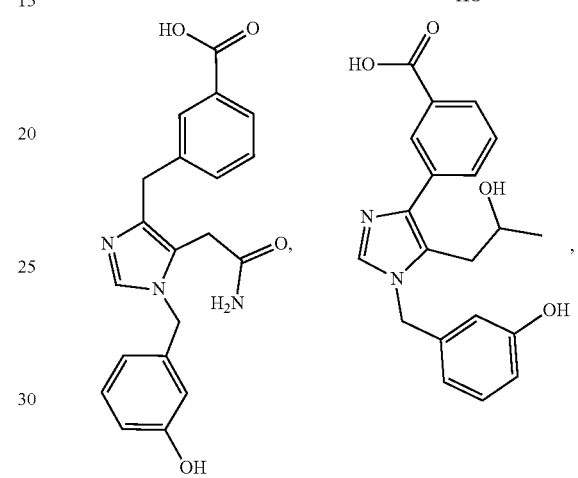
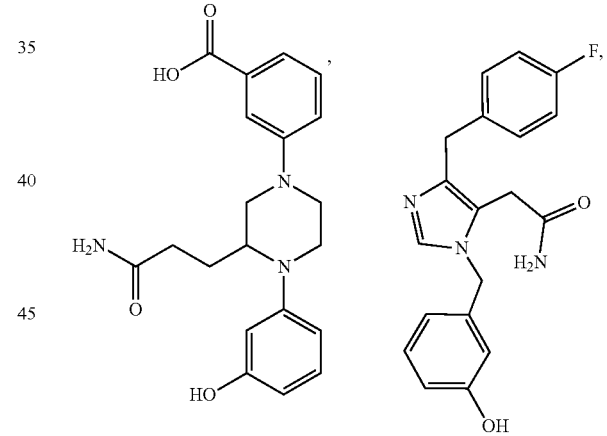
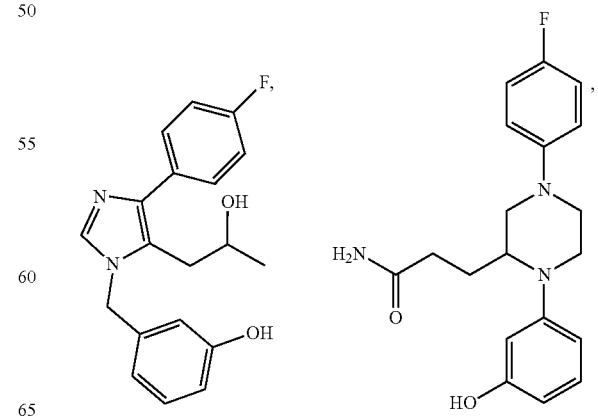

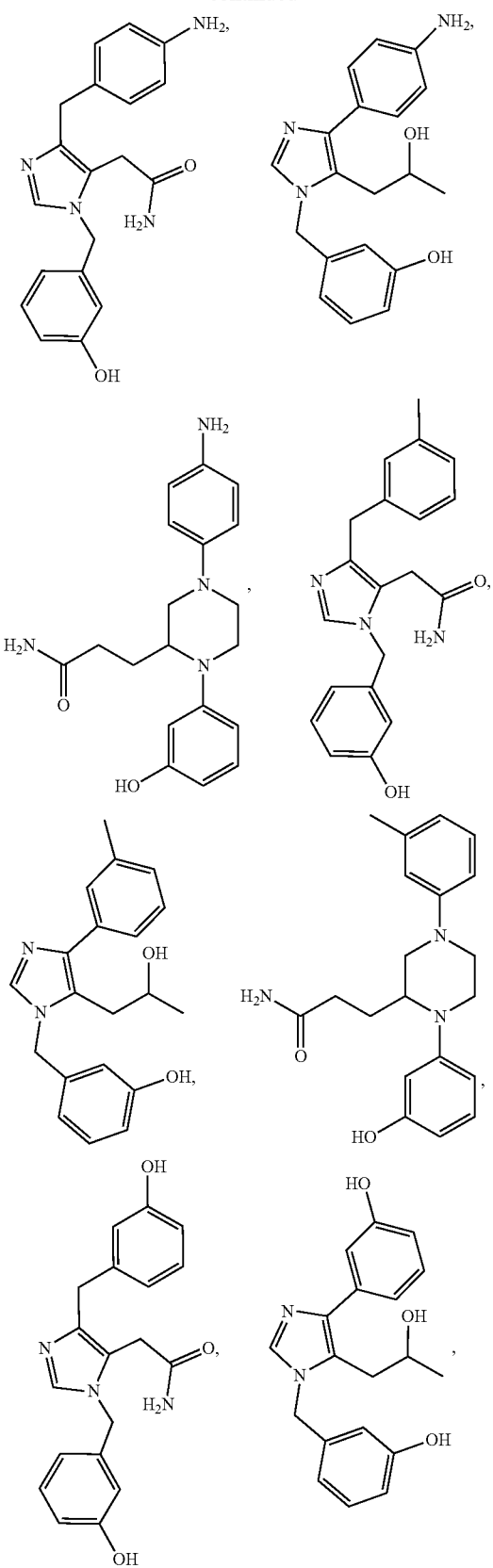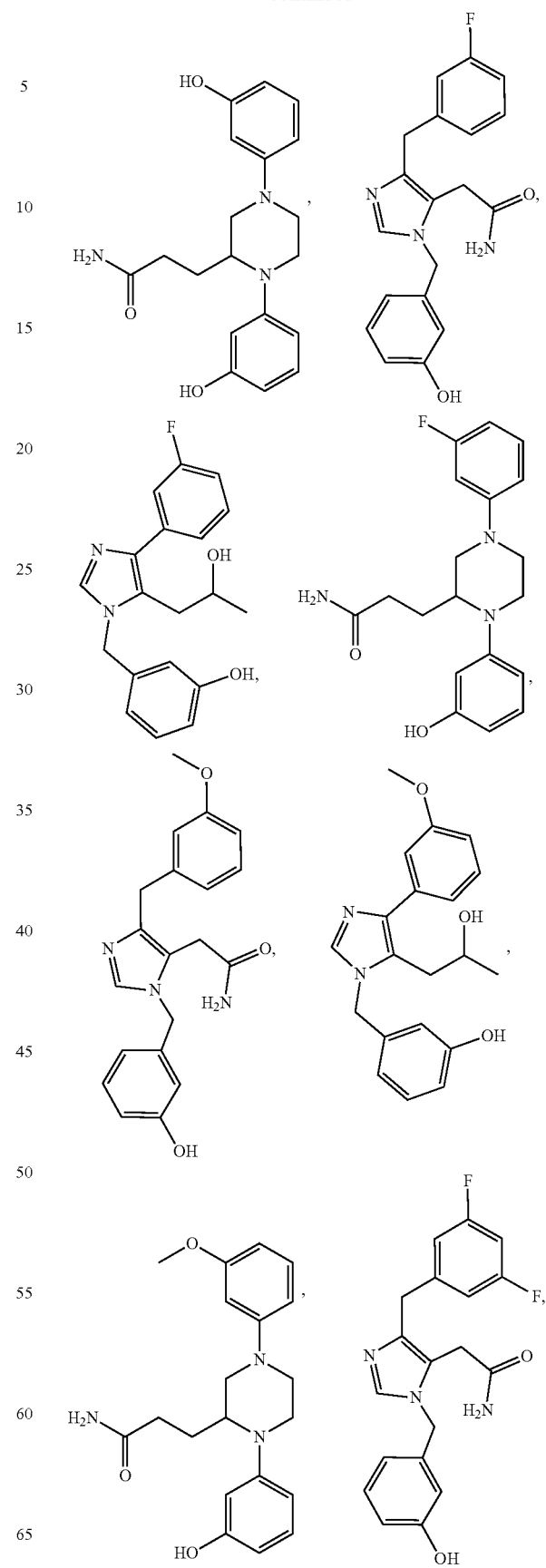

35
-continued
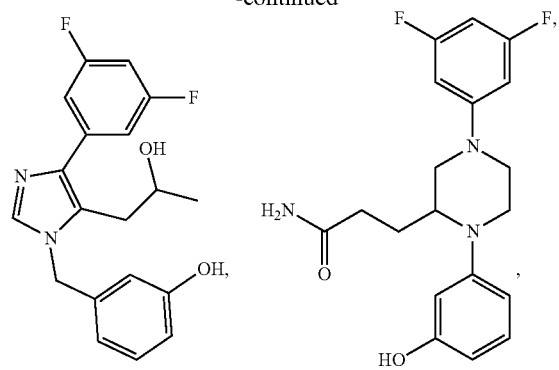
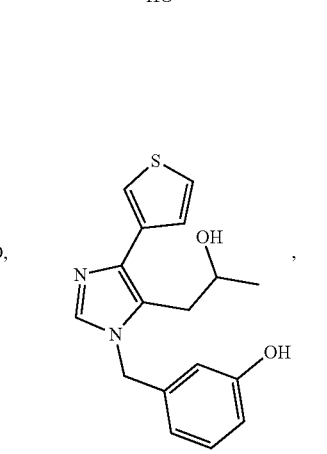
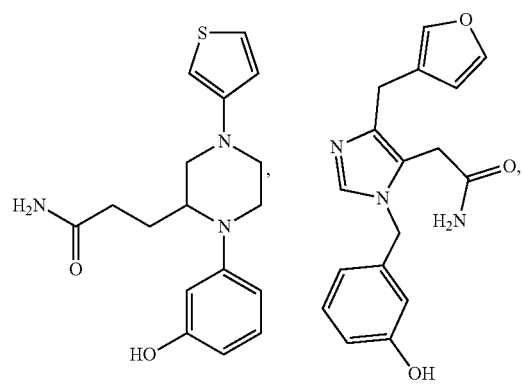
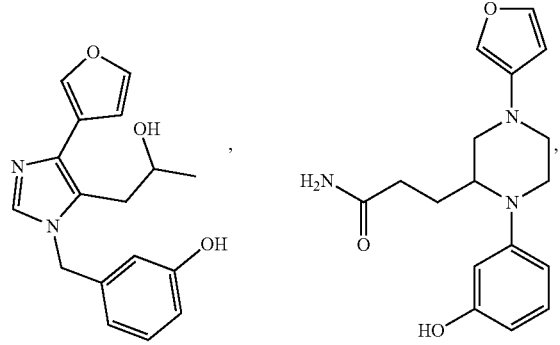
36
-continued
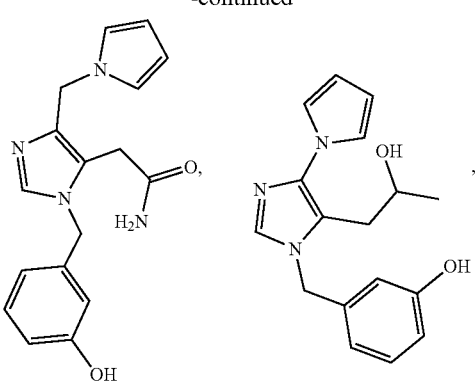
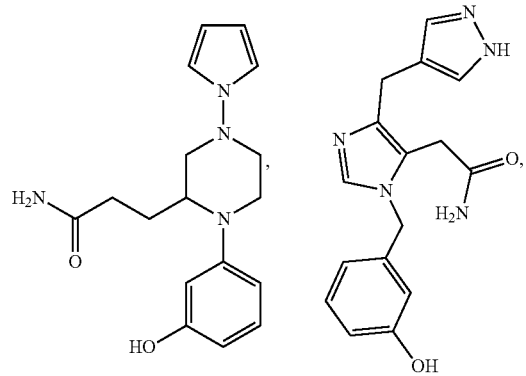
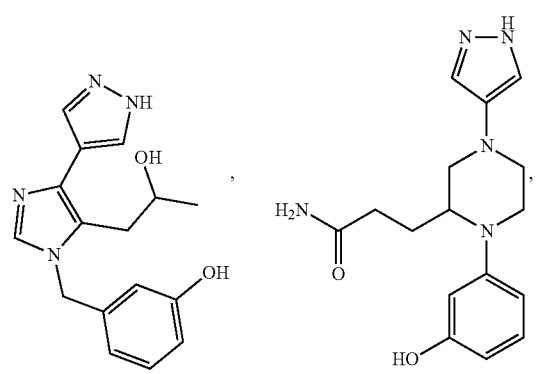
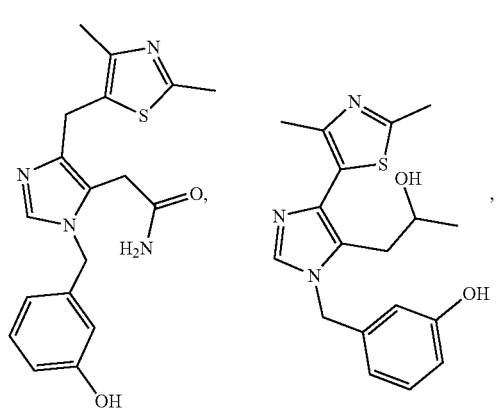

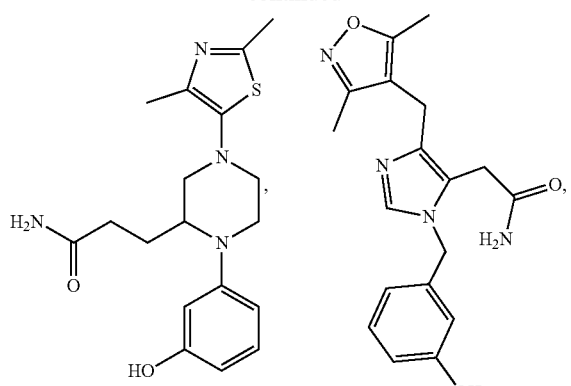
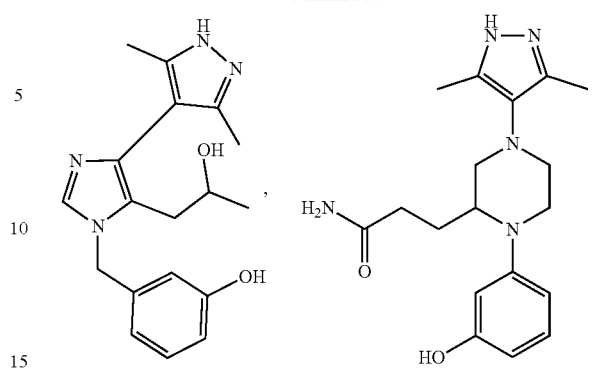

-continued
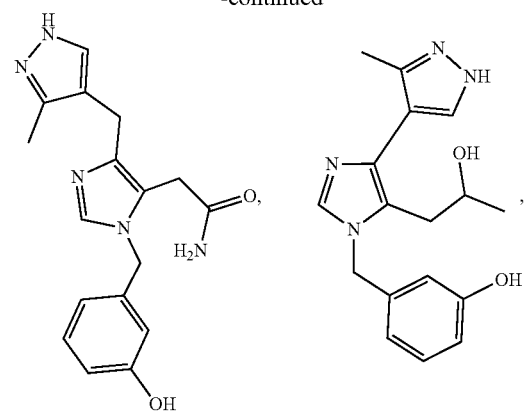
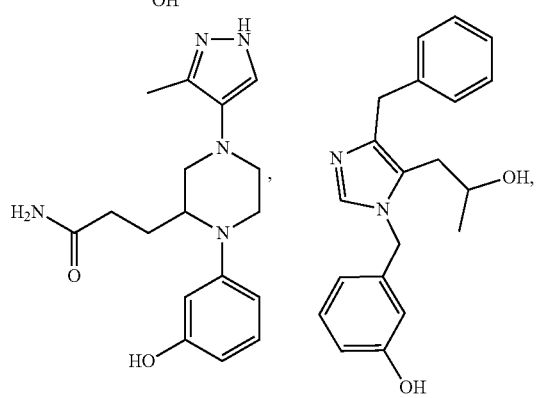
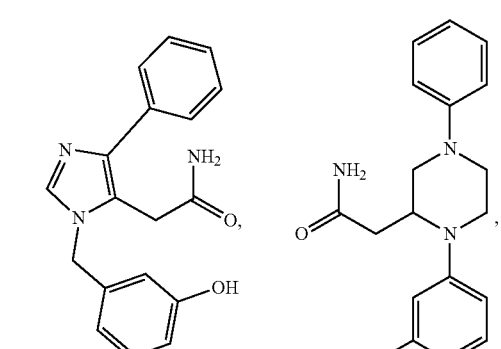
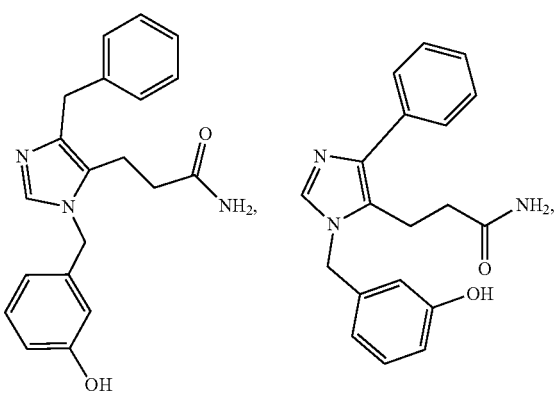
-continued
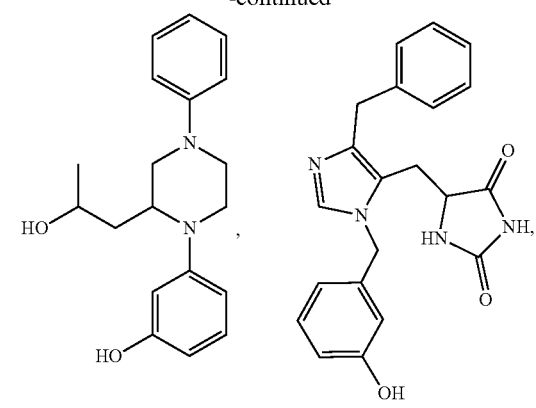
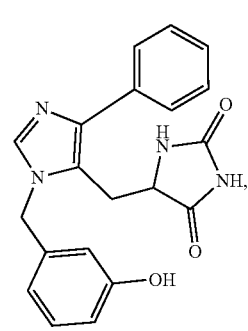
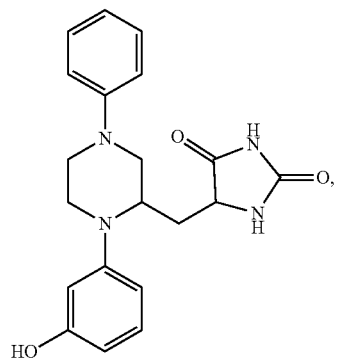
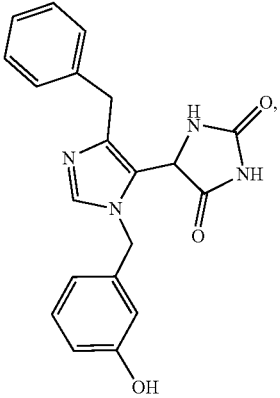

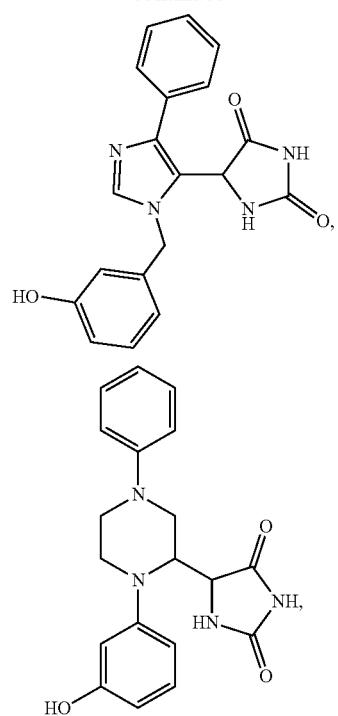
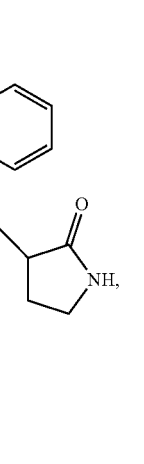
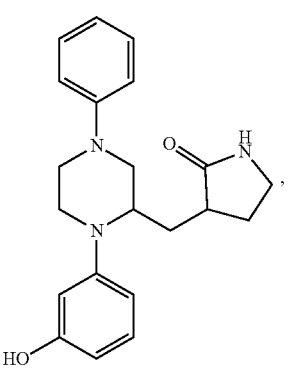
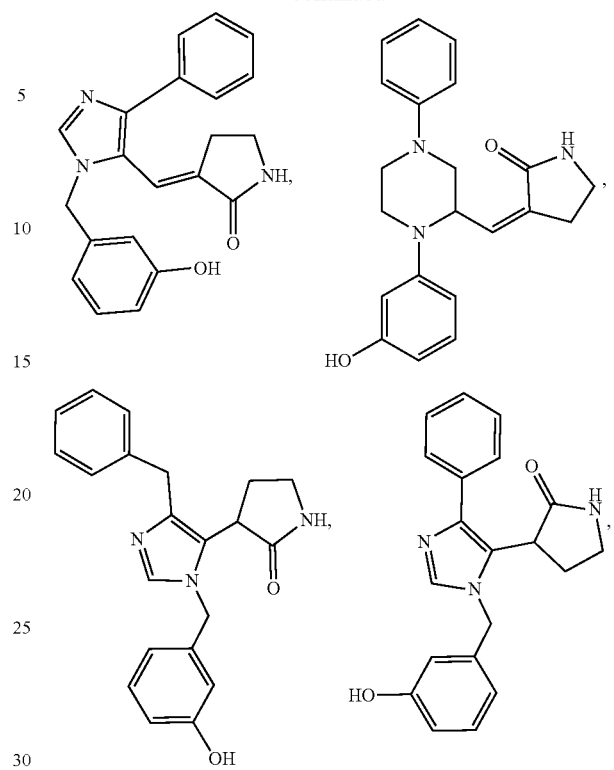
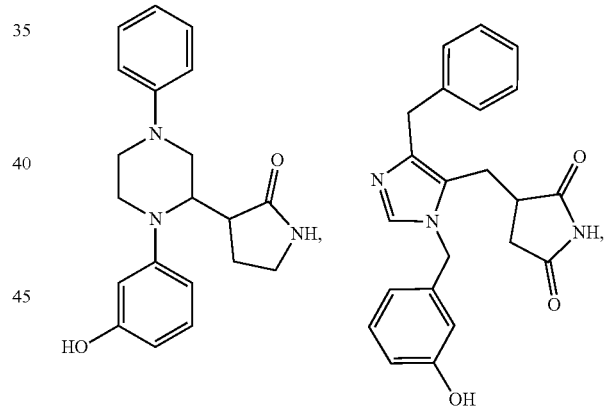
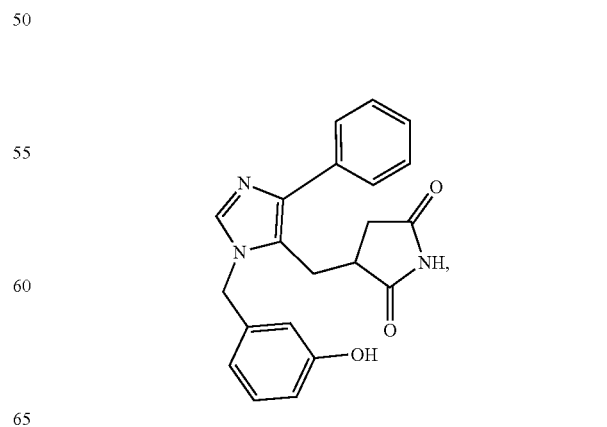

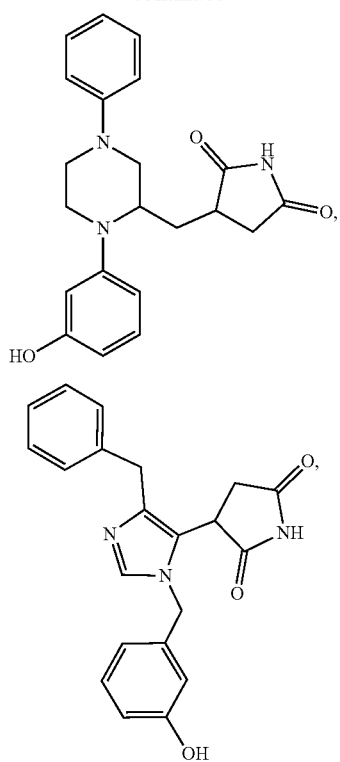
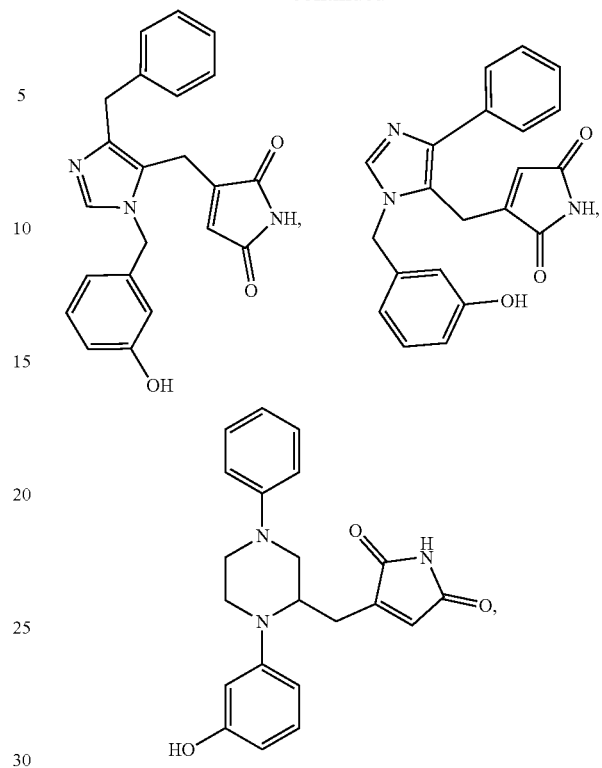
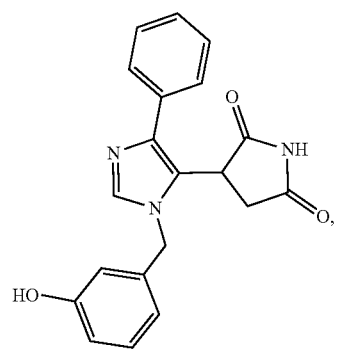
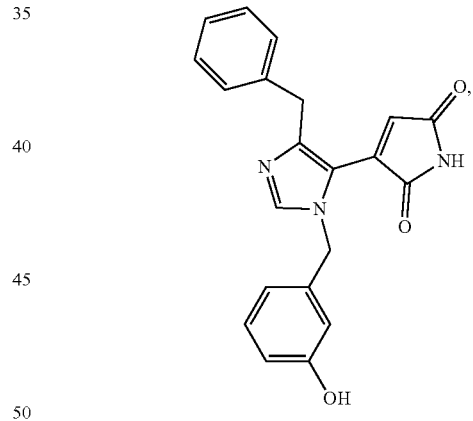
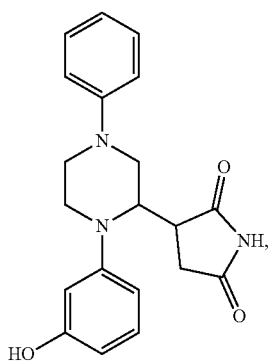
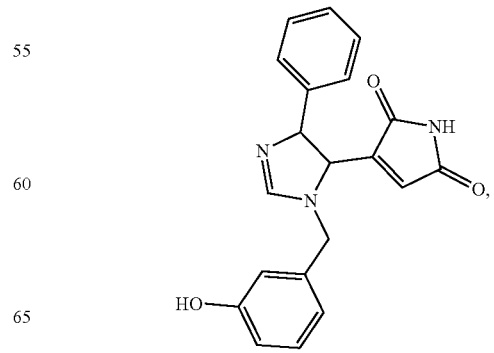

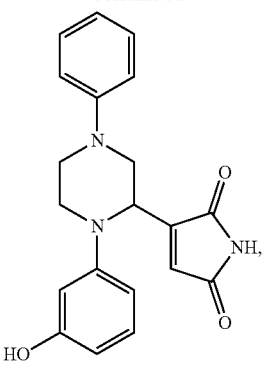
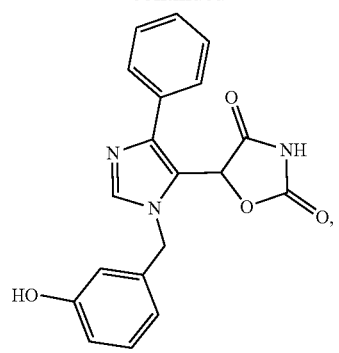
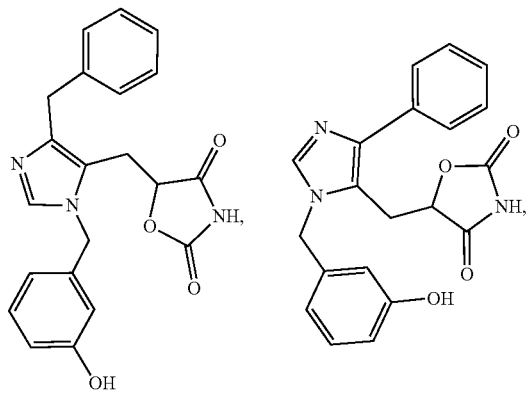
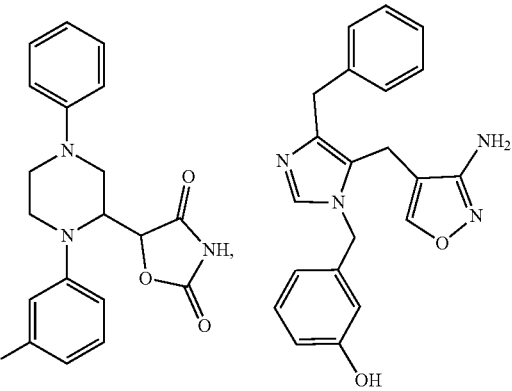
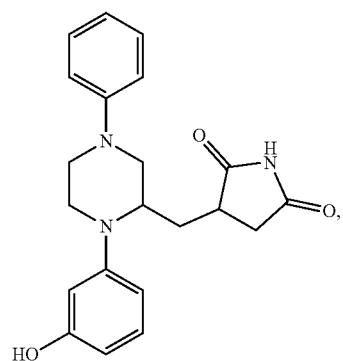
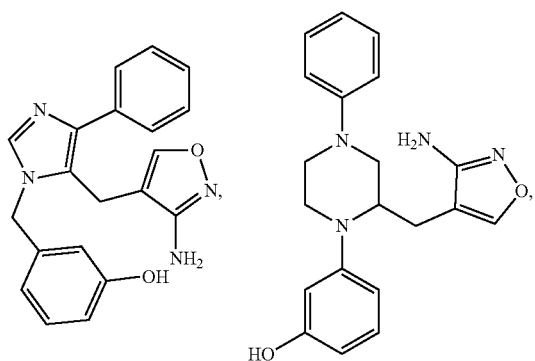
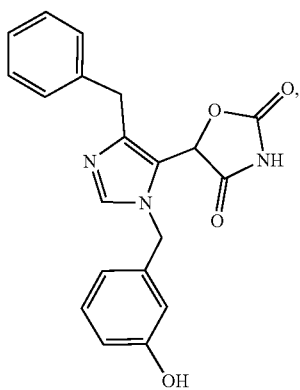
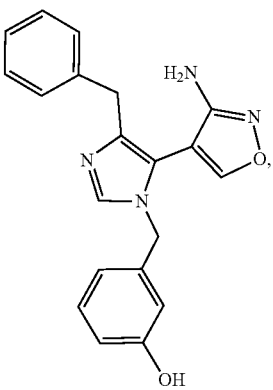

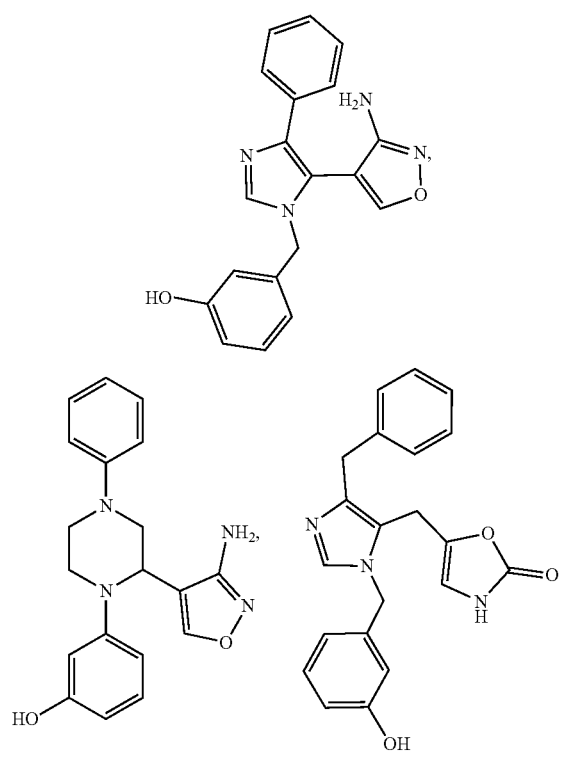
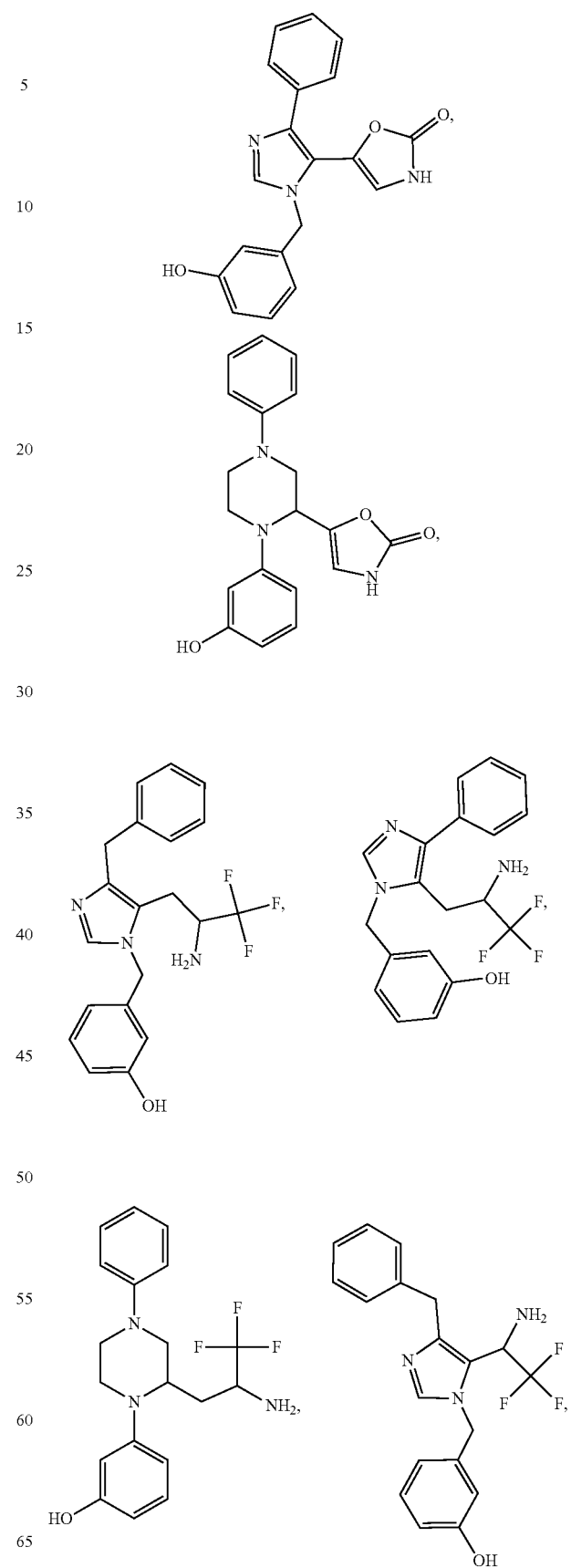

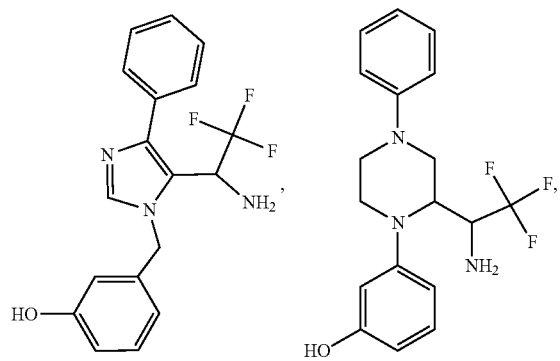
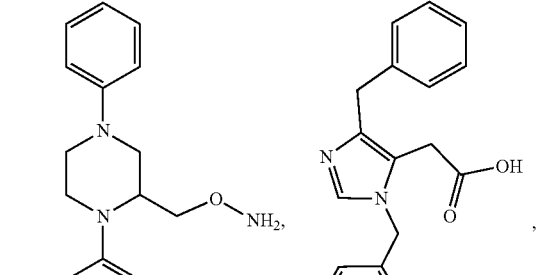
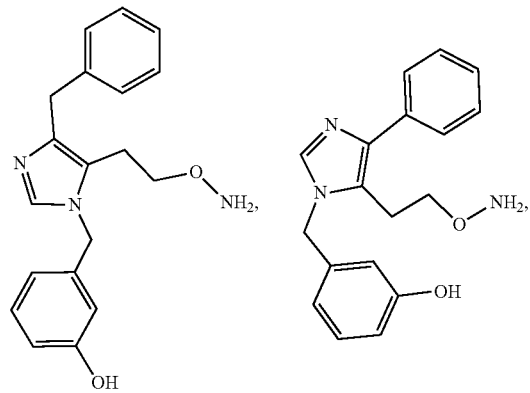
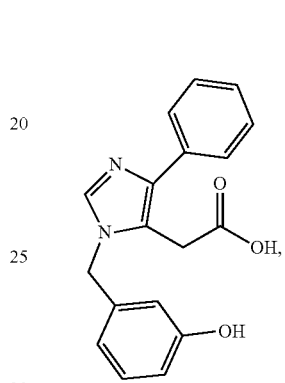
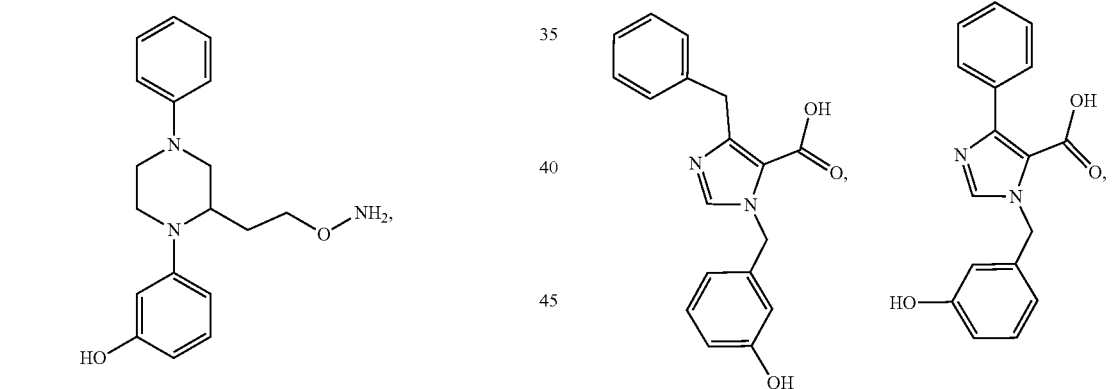
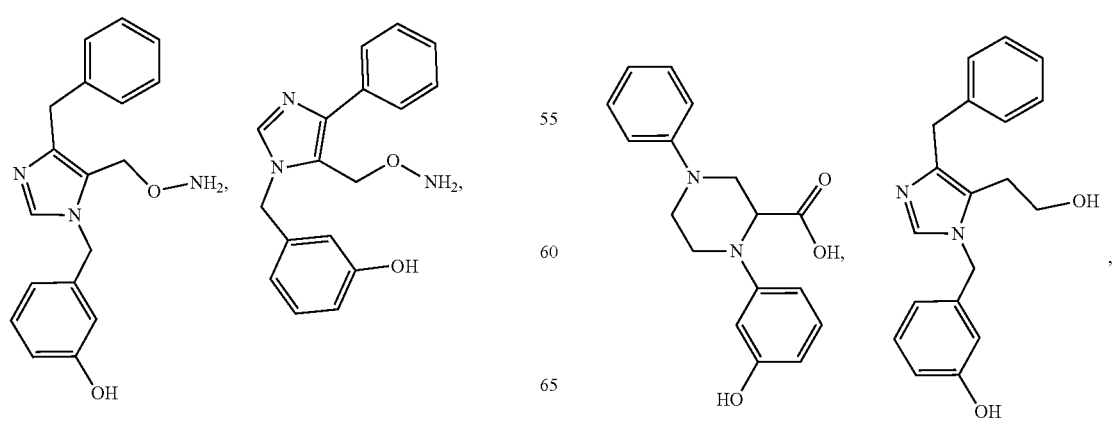

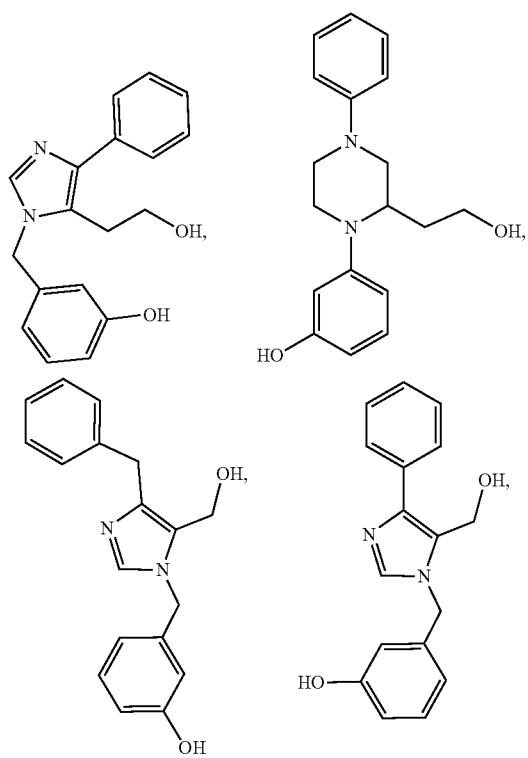
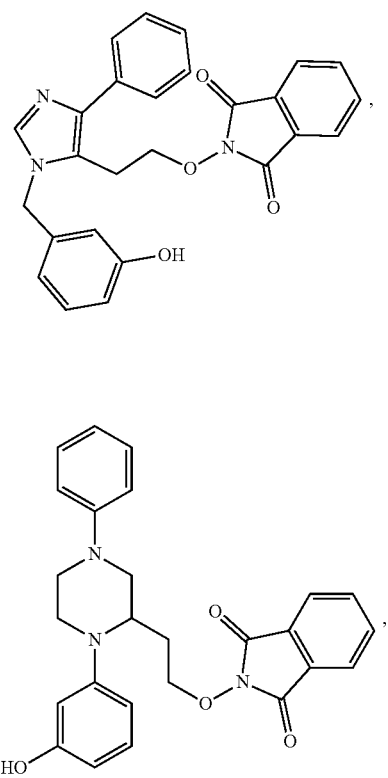
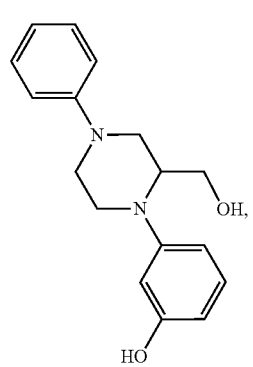
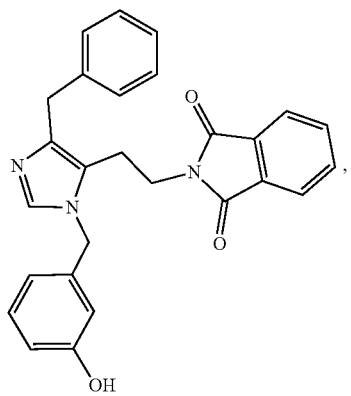
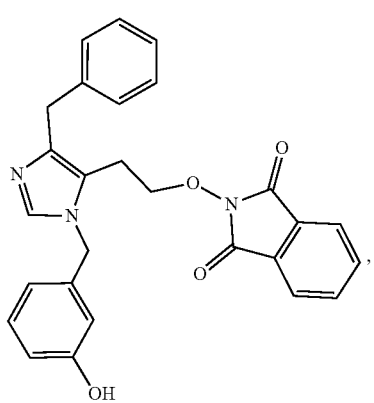
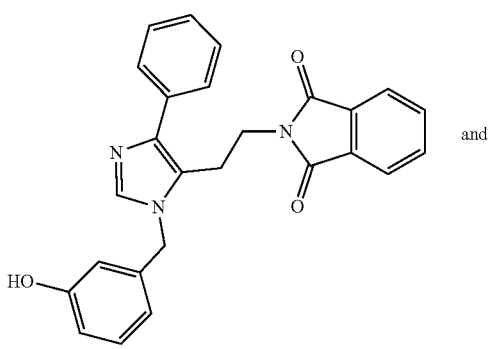

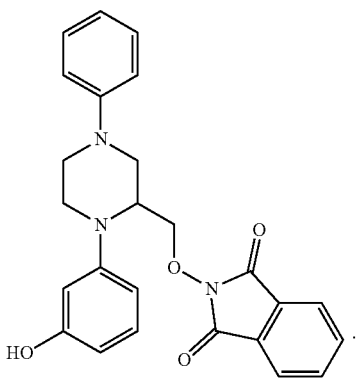

In one embodiment, the compound is selected from:

VB0002

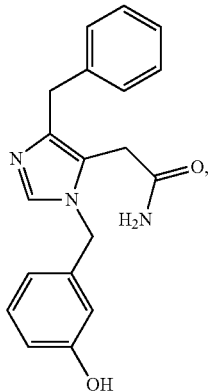

VB0003

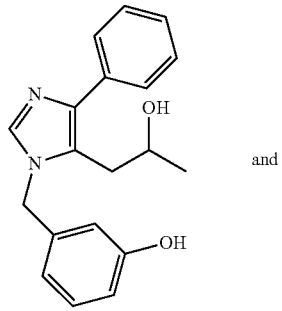

and

VB0005

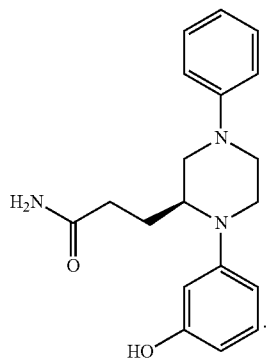 [SMILES: NC(=O)CC[C@H]1CN(c2ccccc2)CCN1c1cccc(O)c1]

According to another aspect, the present invention relates to a pharmaceutical composition comprising a compound of the present invention and a pharmaceutically acceptable excipient.

According to another aspect, the present invention relates to a method for the therapeutic treatment of hypertension or prehypertension in a subject comprising administering to the subject a compound according to the present invention.

According to another aspect, the present invention relates to a method for the therapeutic treatment of fibrosis in a subject comprising administering to the subject a compound according to the present invention.

According to another aspect, the present invention relates to a method for the prophylactic treatment of fibrosis in a subject comprising administering to the subject a compound according to the present invention.

According to another aspect, the present invention relates to a method for the therapeutic treatment of hypertension and fibrosis in a subject comprising administering to the subject a compound according to the present invention.

According to another aspect, the present invention relates to a method for the therapeutic treatment of prehypertension and fibrosis in a subject comprising administering to the subject a compound according to the present invention.

According to another aspect, the present invention relates to a compound of the present invention for use in the therapeutic treatment of hypertension or prehypertension.

According to another aspect, the present invention relates to a compound of the present invention for use in the therapeutic treatment of fibrosis.

According to another aspect, the present invention relates to a compound of the present invention for use in the prophylactic treatment of fibrosis.

According to another aspect, the present invention relates to a compound of the present invention for use in the therapeutic treatment of hypertension and fibrosis.

According to another aspect, the present invention relates to a compound of the present invention for use in the therapeutic treatment of prehypertension and fibrosis.

According to another aspect, the present invention relates to use of a compound of the present invention for the manufacture of a medicament for the therapeutic treatment of hypertension or prehypertension.

According to another aspect, the present invention relates to use of a compound of the present invention for the manufacture of a medicament for the therapeutic treatment of fibrosis.

According to another aspect, the present invention relates to use of a compound of the present invention for the manufacture of a medicament for the prophylactic treatment of fibrosis.

According to another aspect, the present invention relates to use of a compound of the present invention for the manufacture of a medicament for the therapeutic treatment of hypertension and fibrosis.

According to another aspect, the present invention relates to use of a compound of the present invention for the manufacture of a medicament for the therapeutic treatment of prehypertension and fibrosis.

In one embodiment, the fibrosis is myocardial fibrosis.
In one embodiment, the fibrosis is kidney fibrosis.
In one embodiment, the fibrosis is liver fibrosis.
In one embodiment, the fibrosis is lung fibrosis.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DETAILED DESCRIPTION OF THE INVENTION

Figure 1:
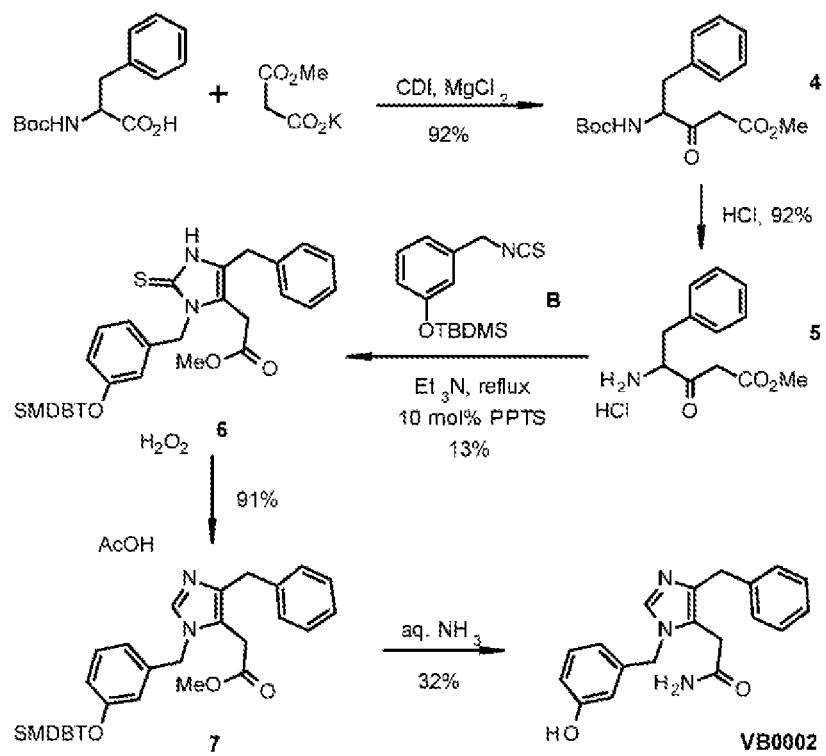
FIG. 1: Synthesis of 2-[4-Benzyl-1-(3-hydroxybenzyl)-1H-imidazol-5-yl]acetamide (VB0002).

The present invention relates to certain compounds that show blood pressure lowering and anti-fibrotic effects in oral dosing studies in an experimental animal model. With respect to anti-fibrotic activity, the compounds of the present invention are effective in preventing fibrosis, slowing down progression of established fibrosis and/or reducing the degree (reversal) of established fibrosis. These are important findings with respect to the range and severity of conditions which can be treated with the compounds of the present invention.

The compounds of the present invention are represented by the formulae:

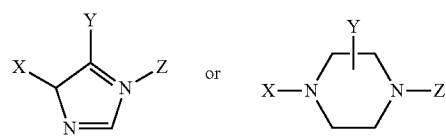

wherein:
X is selected from the group consisting of:

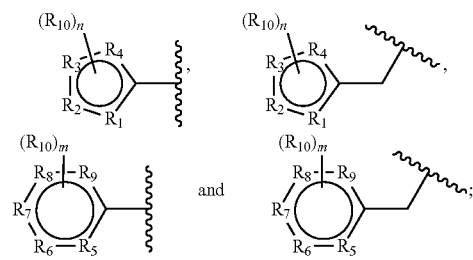

$R_1$ to $R_9$ are independently C, N, O or S;
$R_{10}$ is independently selected from $C_{1-6}$alkyl, halo, $C_{0-6}$alkyl carboxylic acid, amino, hydroxy and $C_{1-6}$alkoxy;
Y is A, $CH_2$-A or CH=A;
A is selected from optionally substituted saturated, partly saturated or unsaturated 5- or 6-membered heterocyclyl; optionally substituted $C_{1-6}$alkoxyl amine; optionally substituted $C_{1-6}$alkyl amine; optionally substituted $C_{0-6}$alkyl carboxylic acid; optionally substituted $C_{1-6}$alkyl hydroxyl; optionally substituted saturated or unsaturated $C_{0-6}$alkyl bicyclic heterocyclyl; and optionally substituted saturated or unsaturated $C_{1-6}$alkoxyl bicyclic heterocyclyl;
Z is selected from the group consisting of:

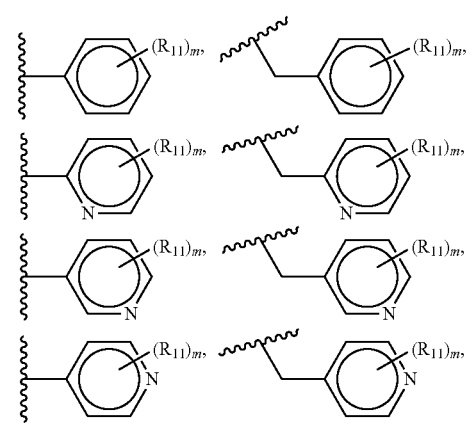

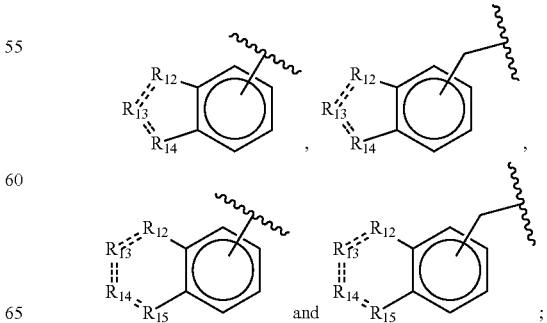

$R_{11}$ is independently selected from halo, alkyl, hydroxy, amino and substituted amino;

$R_{12}$, $R_{14}$ and $R_{15}$ are independently C, CH, CH$_2$, O, N, NH or S;

$R_{13}$ is C, CH, CH$_2$, N, NH, C—CF$_3$, CH—CF$_3$ or C=O;

m is 0, 1, 2, 3, 4 or 5; and n is 0, 1, 2, 3 or 4, or a stereoisomer or pharmaceutically acceptable salt thereof.

The following compounds are specific, but non-limiting, examples of the compounds of the present invention:

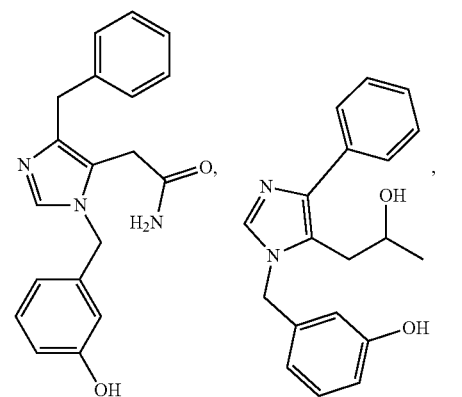

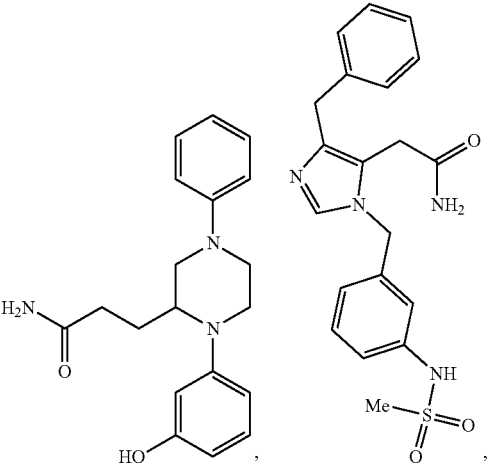

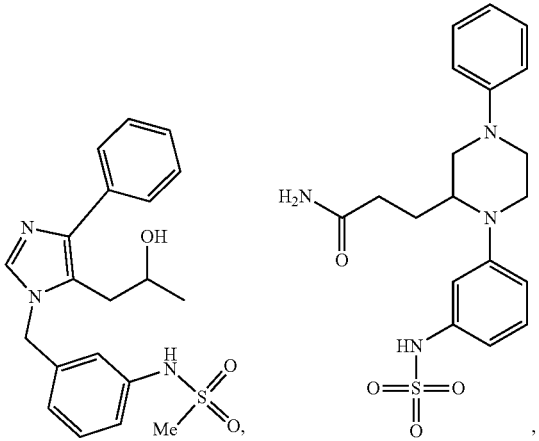

-continued

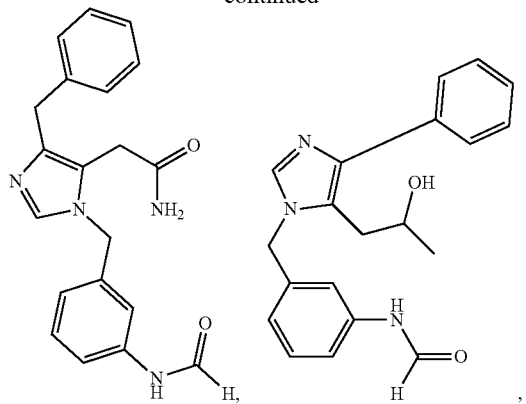

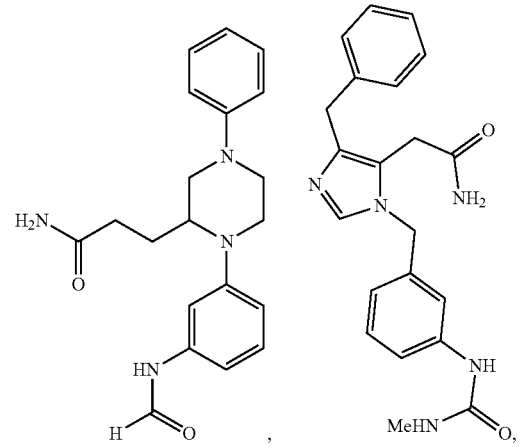

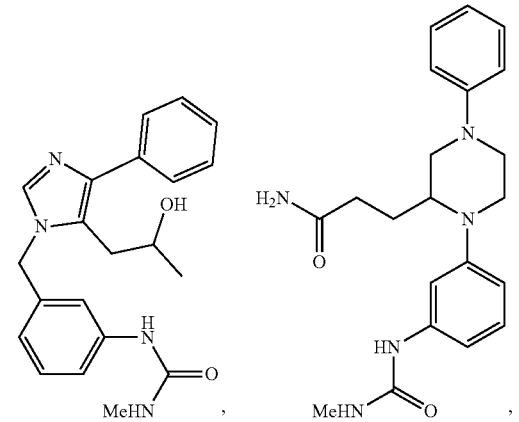

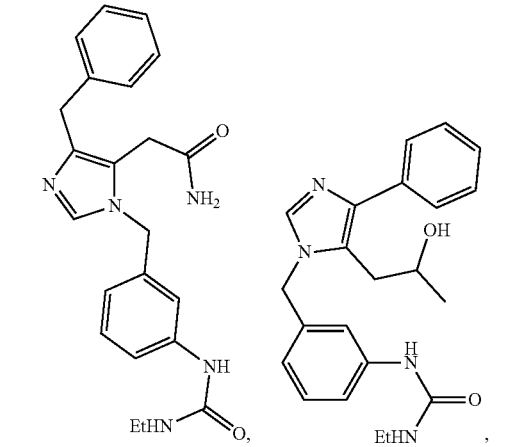

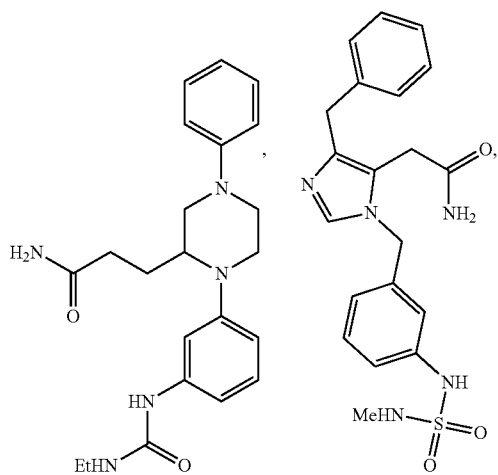
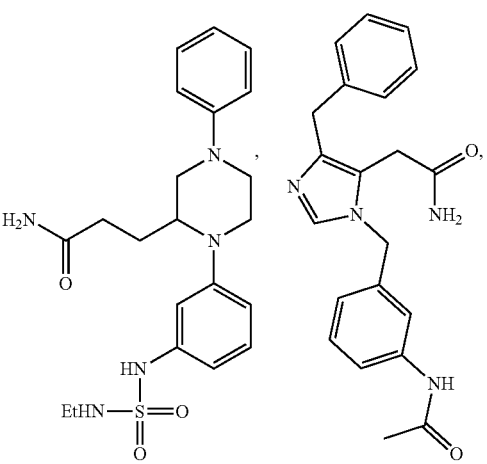
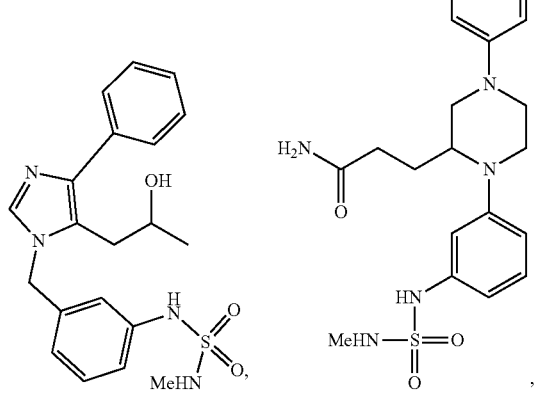
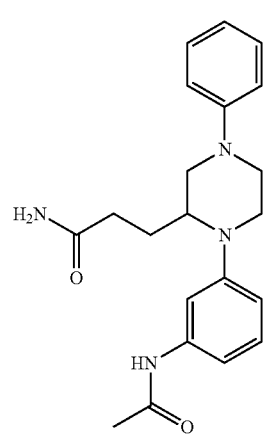
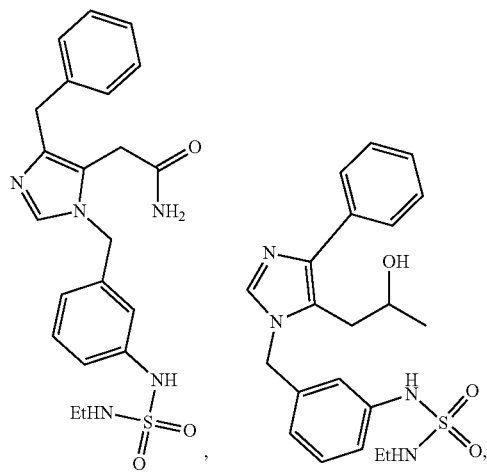
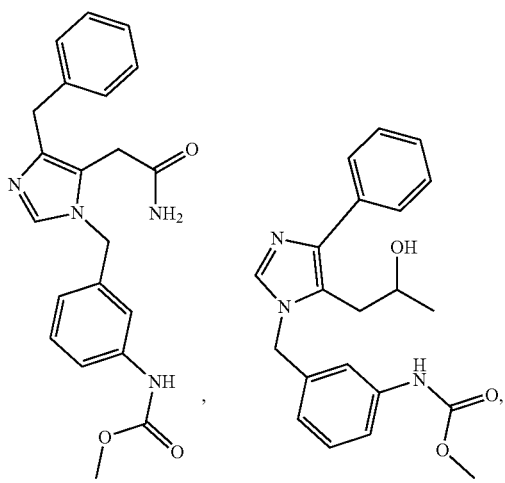

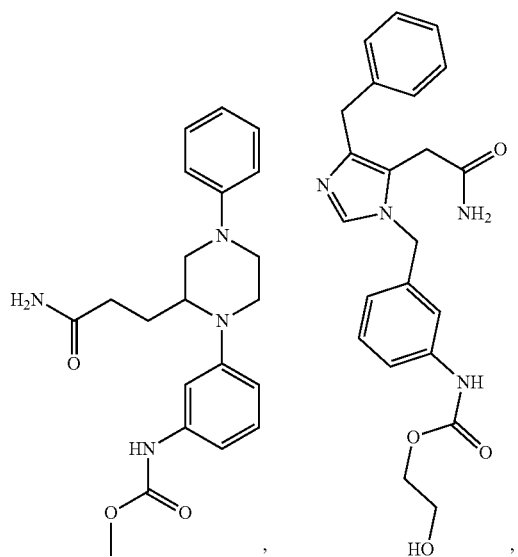
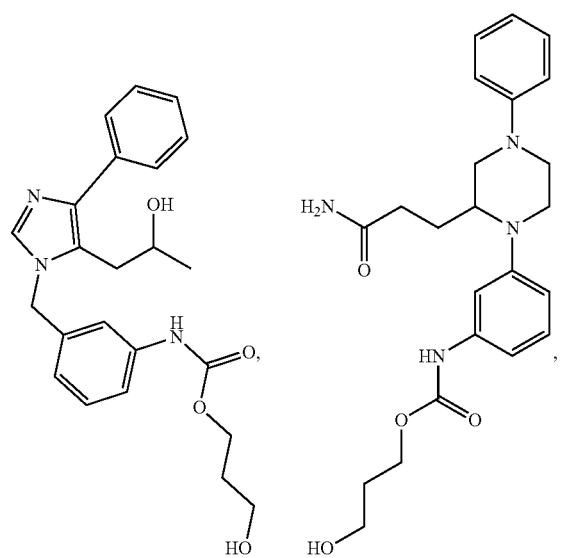
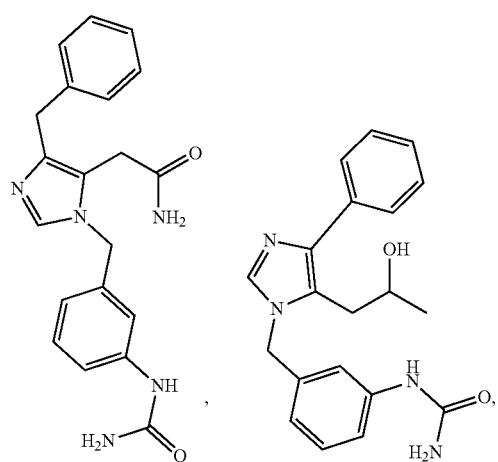
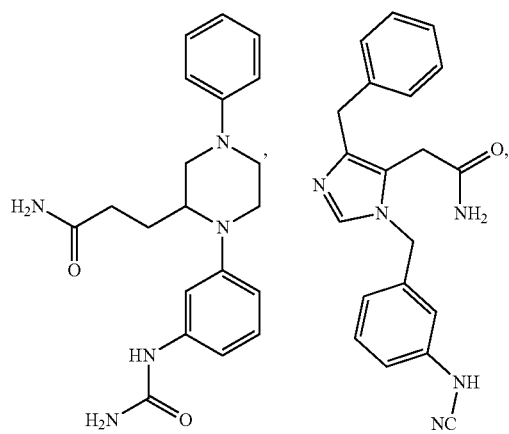
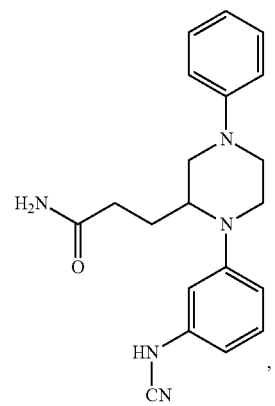
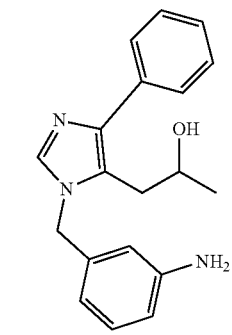
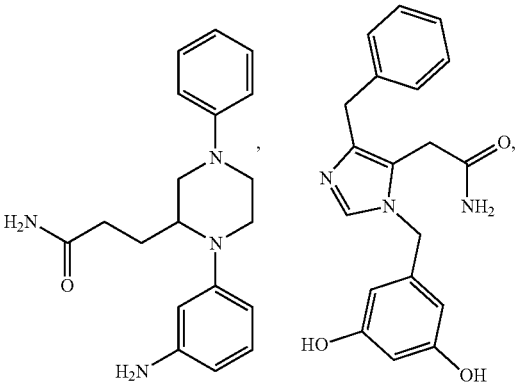

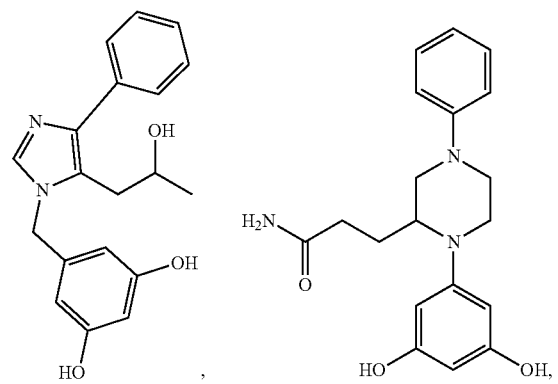
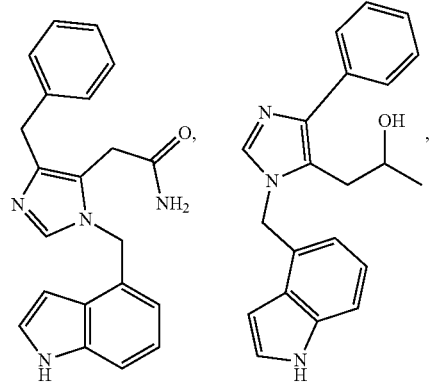
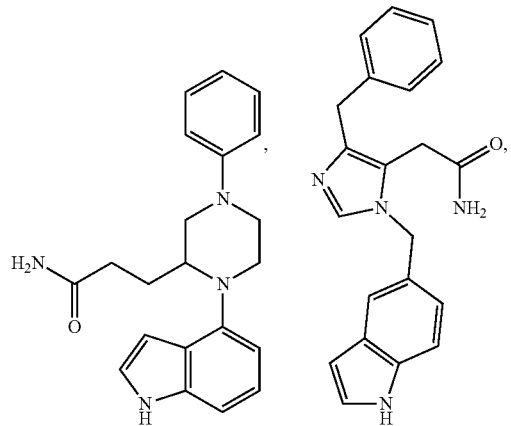
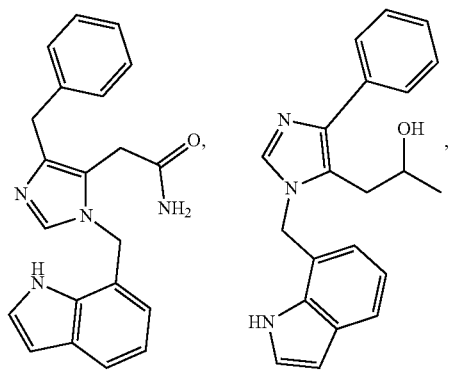
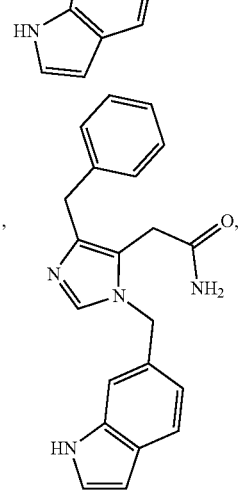
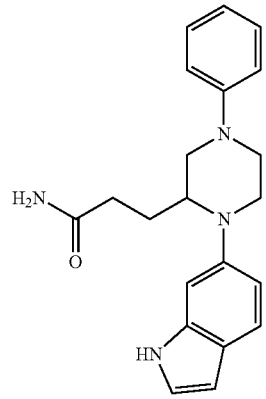
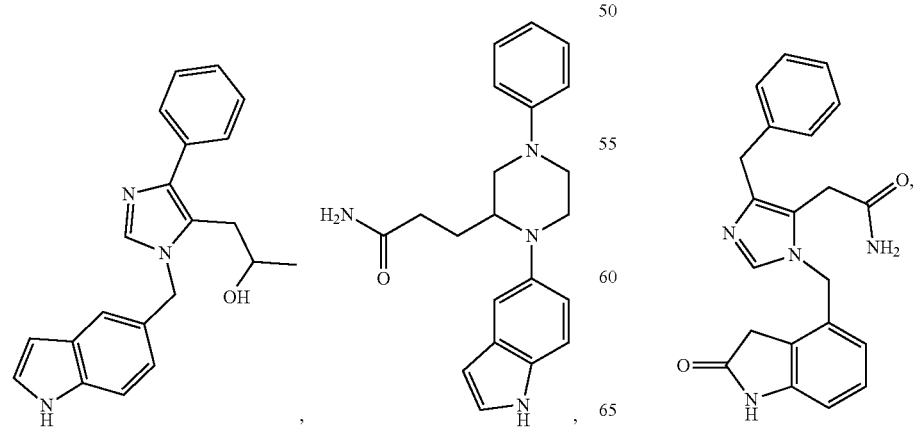
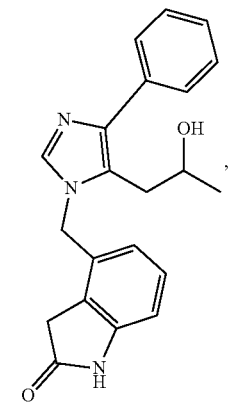

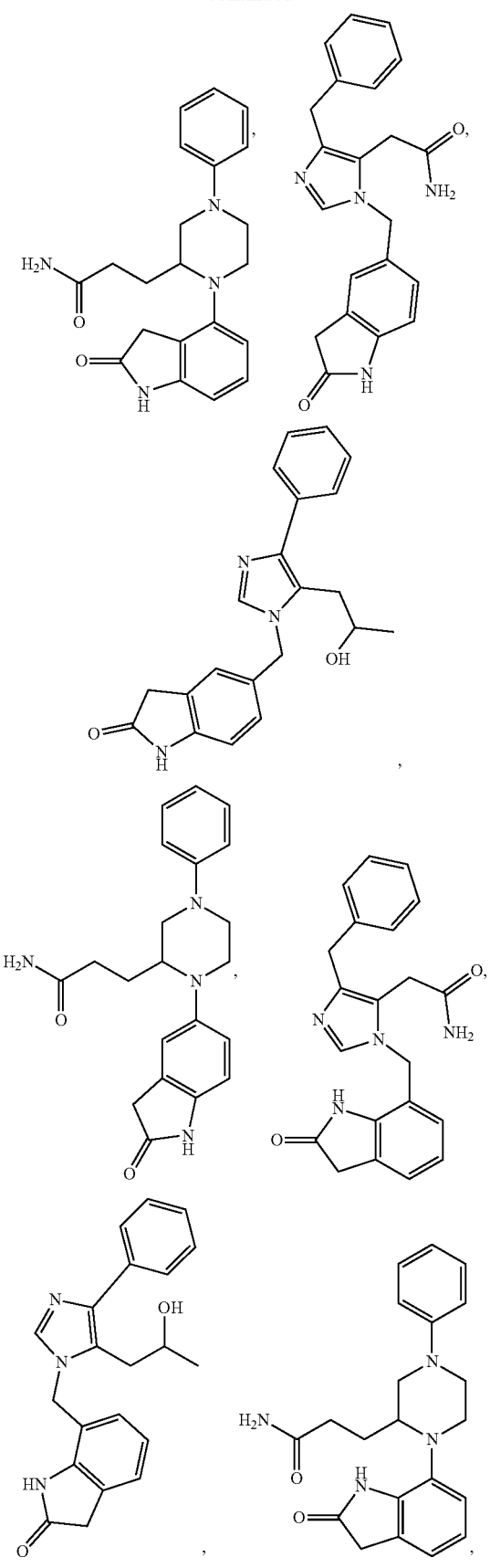
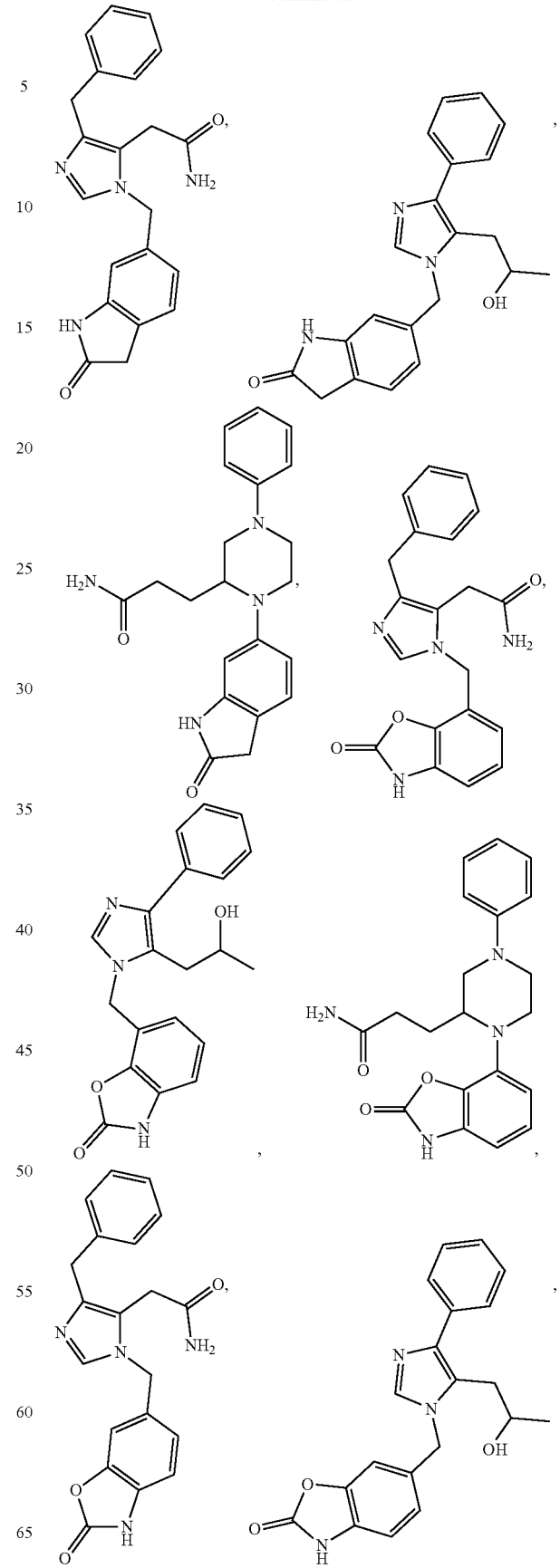

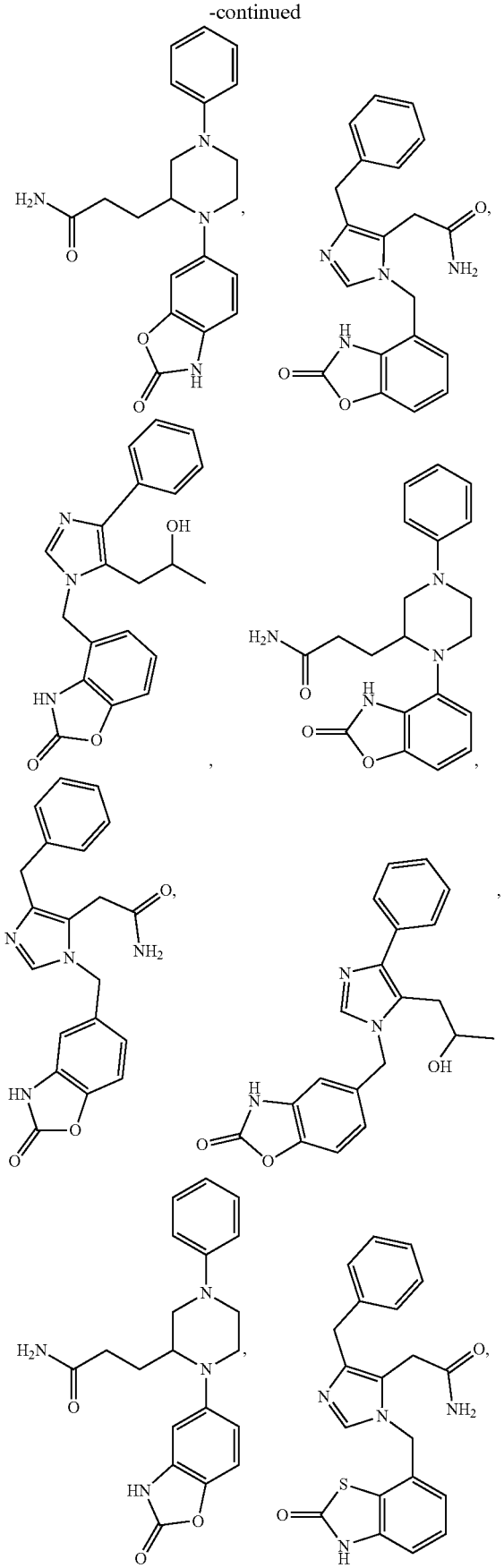
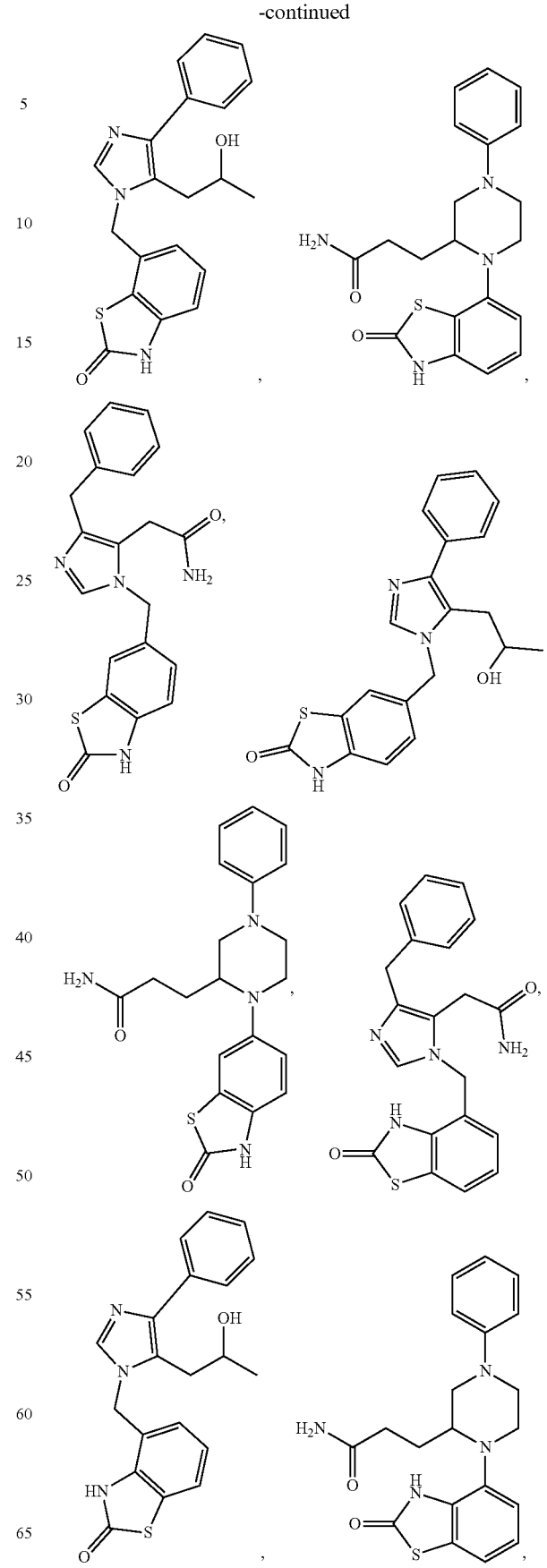

-continued
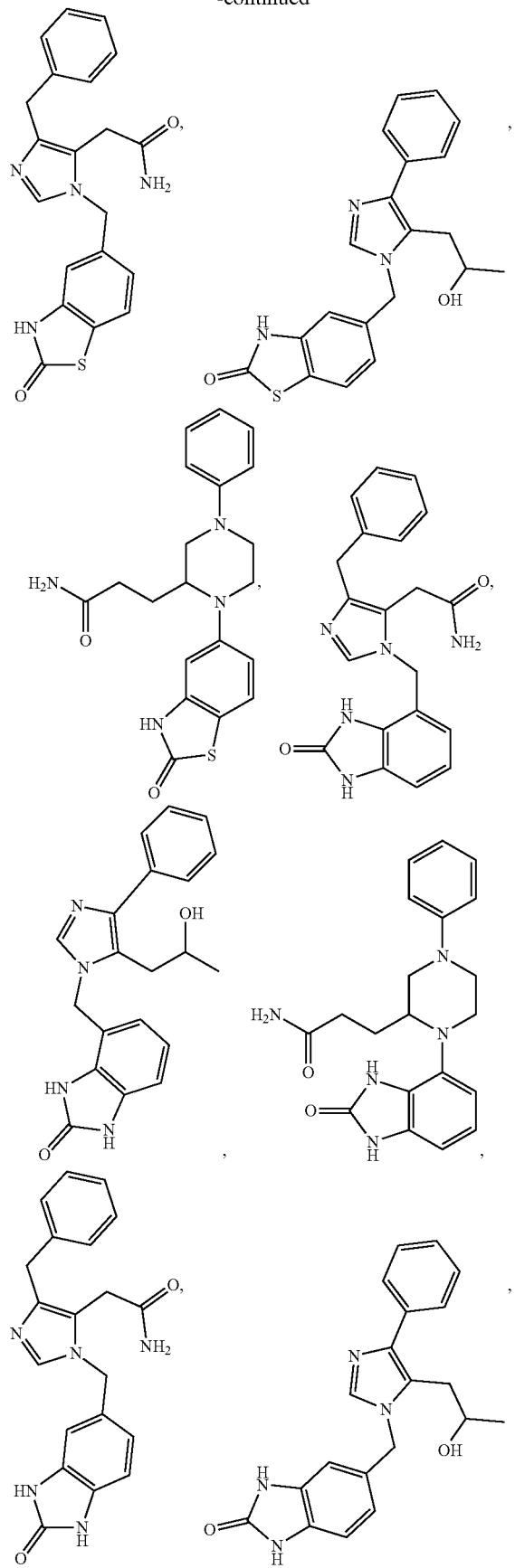
-continued
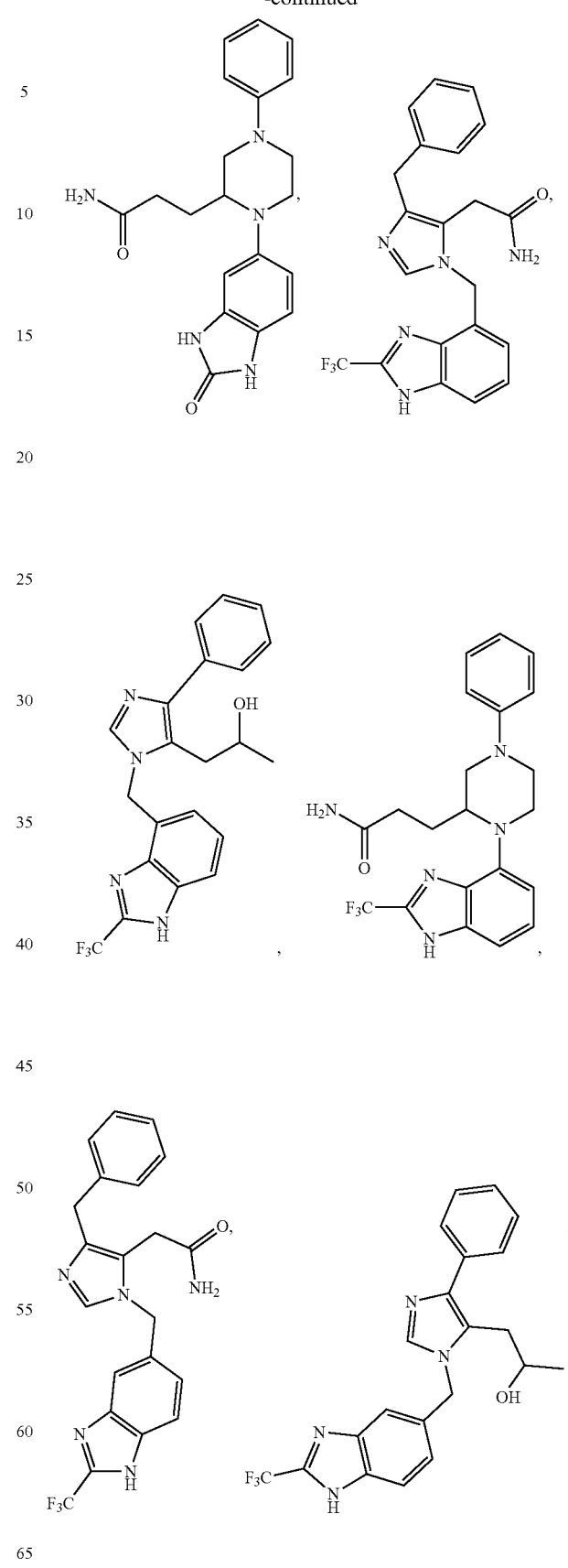

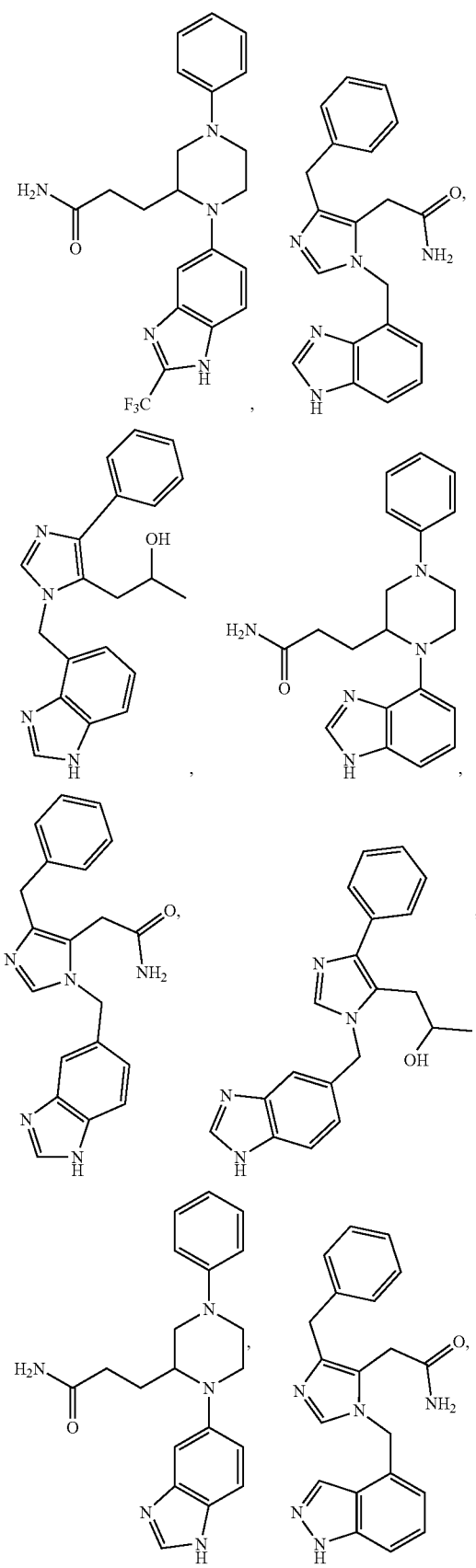
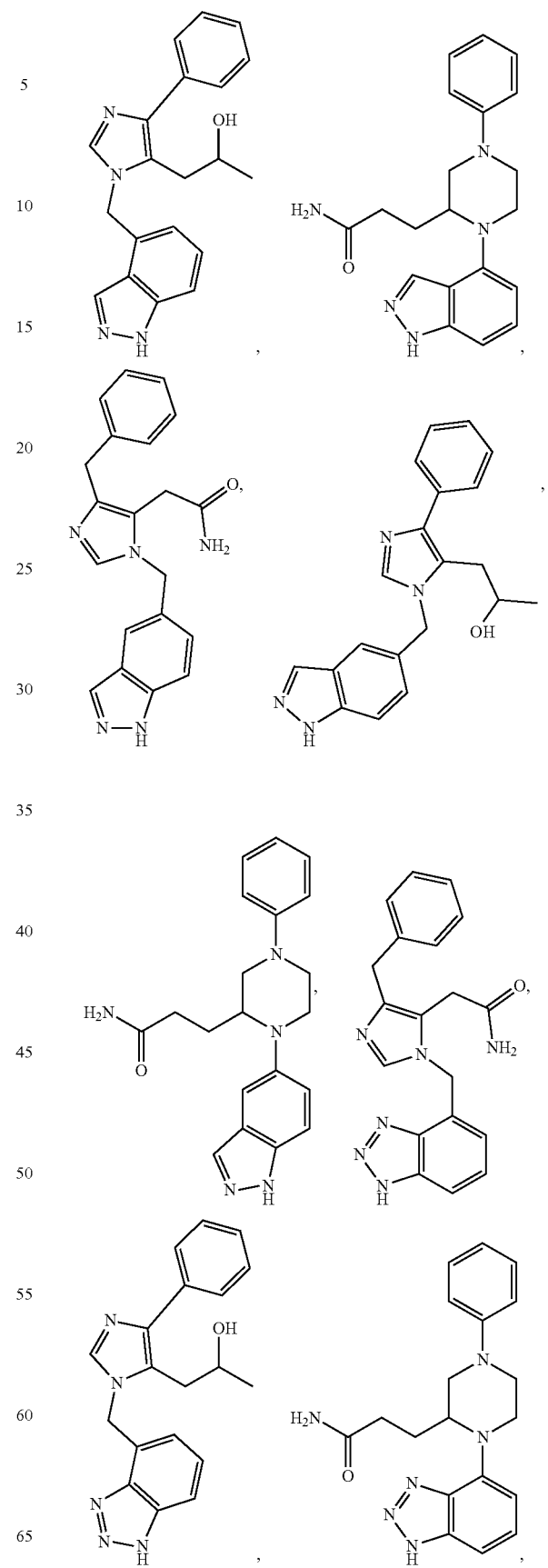

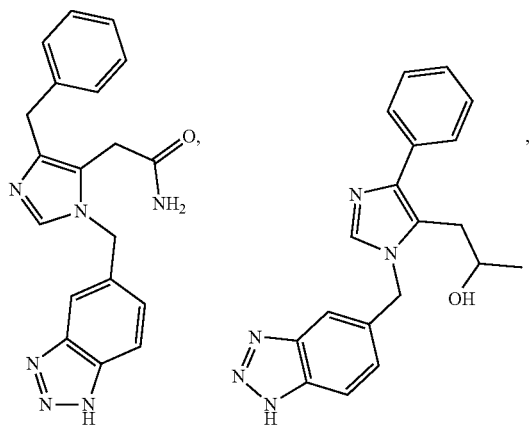
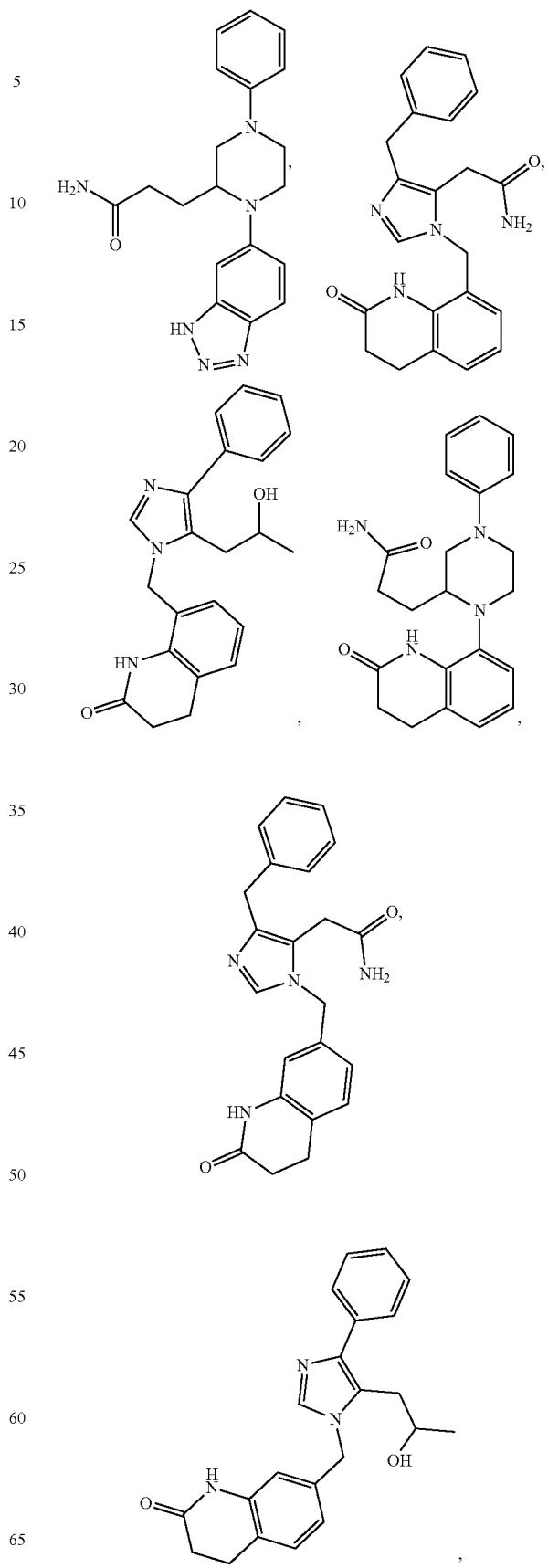

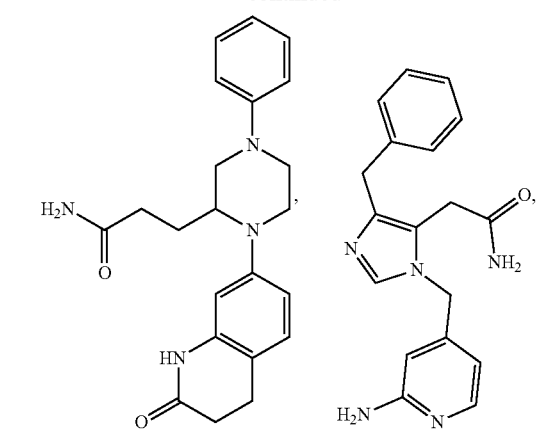
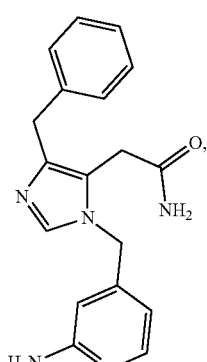
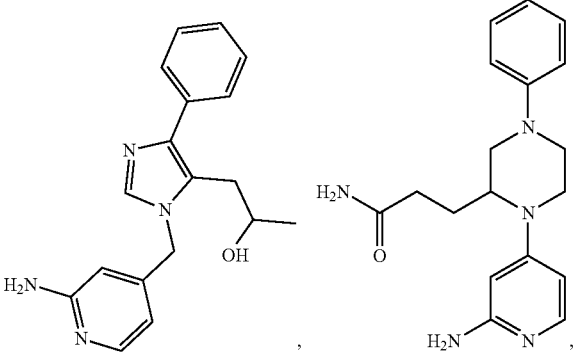
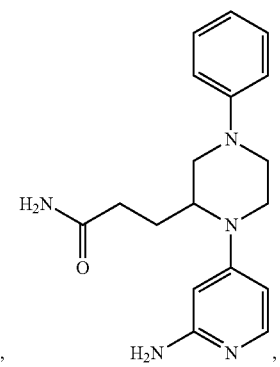
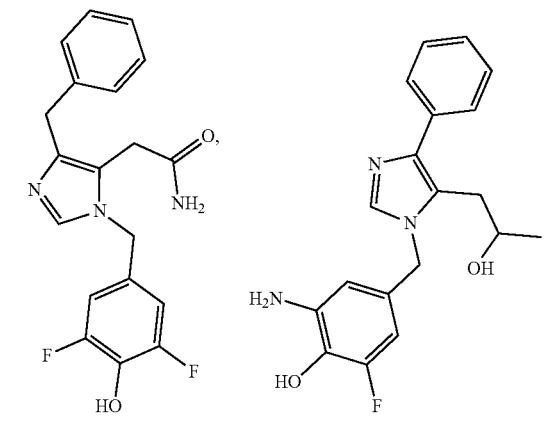
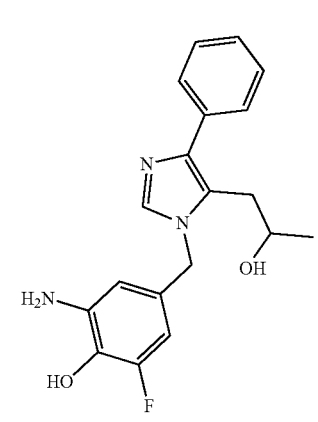
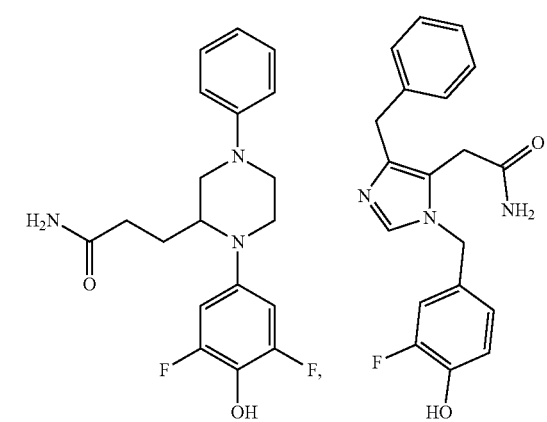
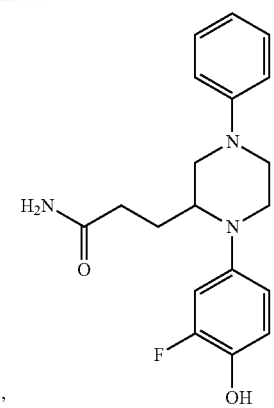
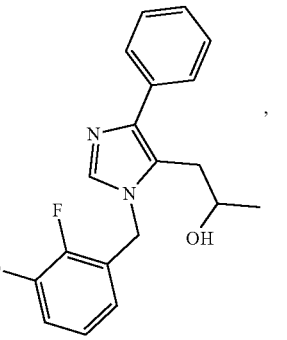
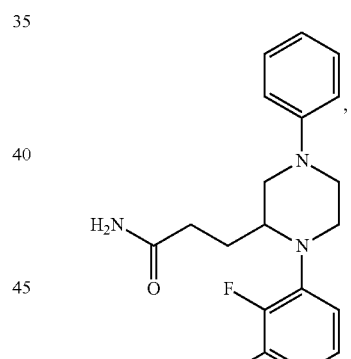
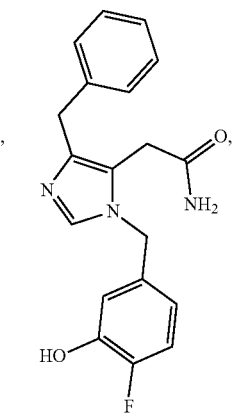
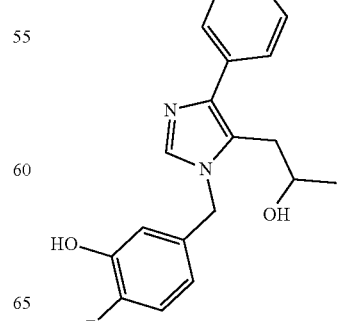
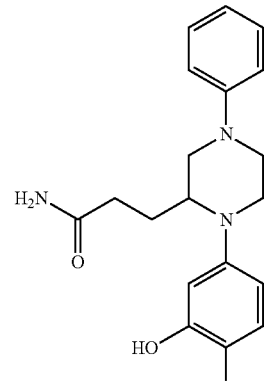

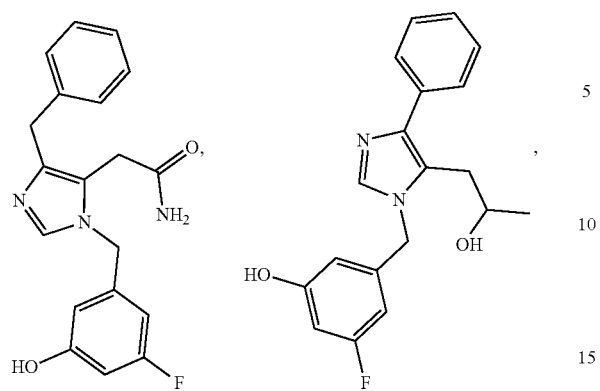
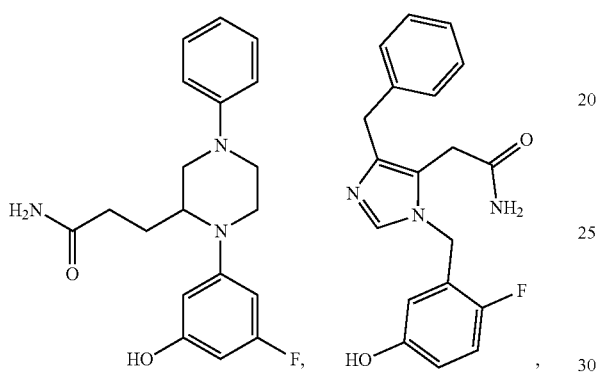
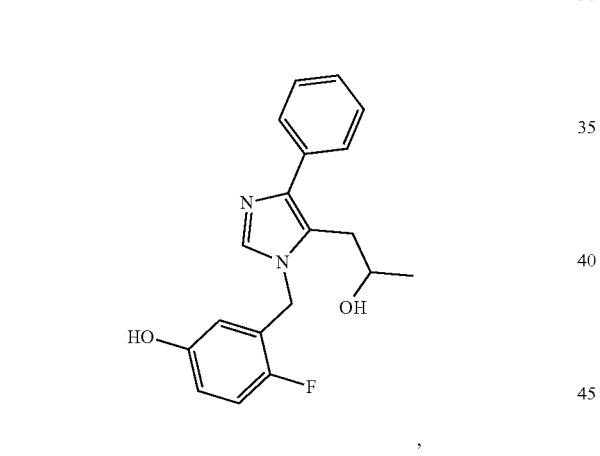
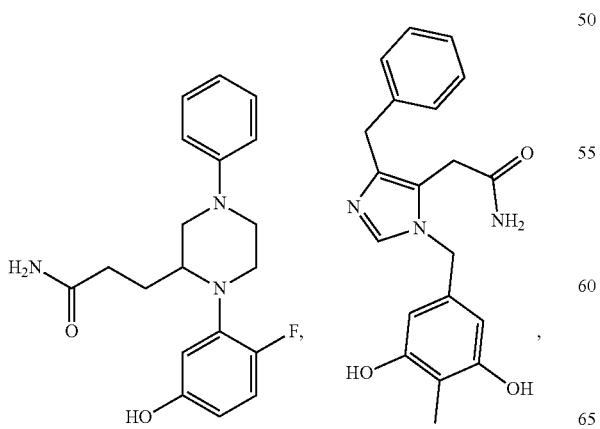
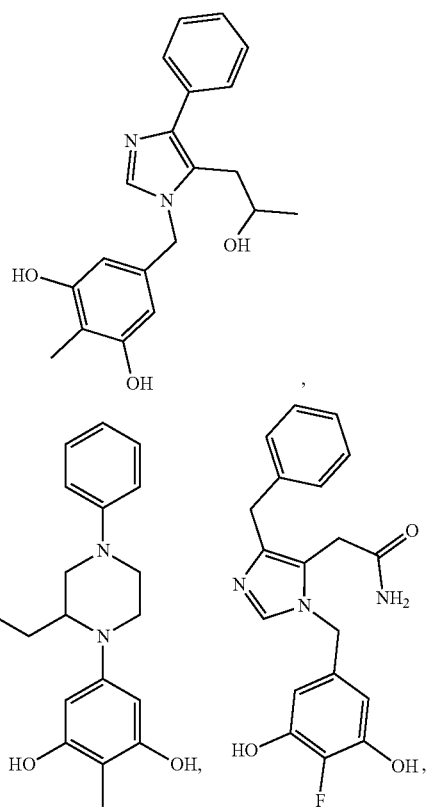
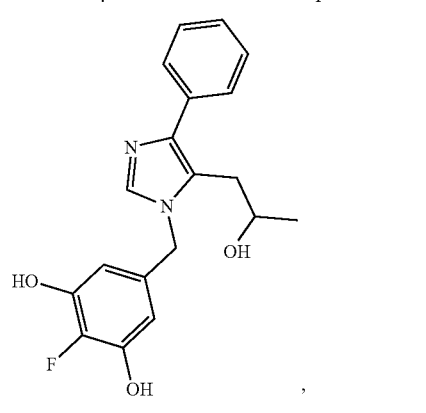
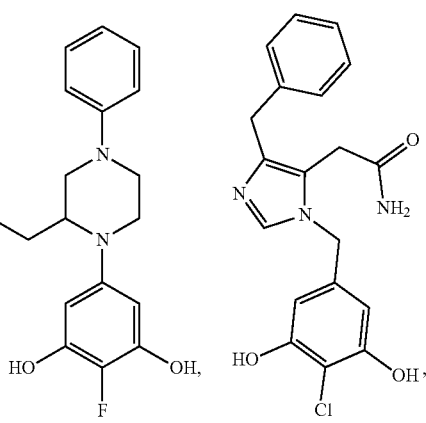

79
-continued
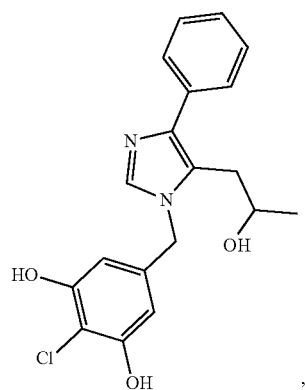
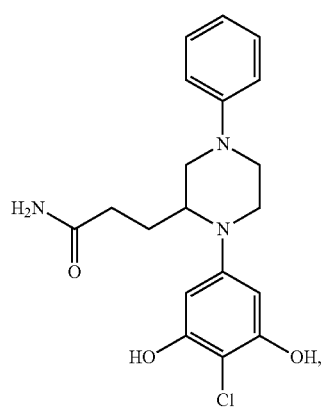
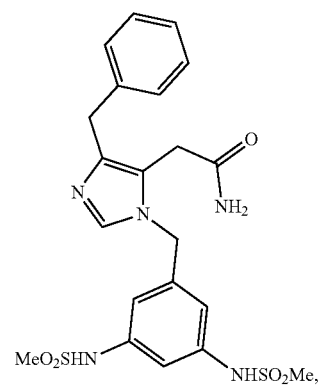
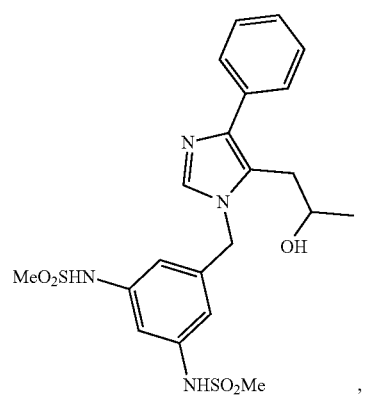
80
-continued
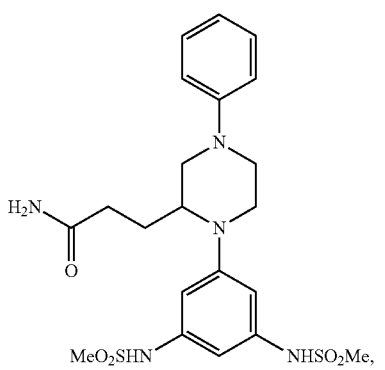
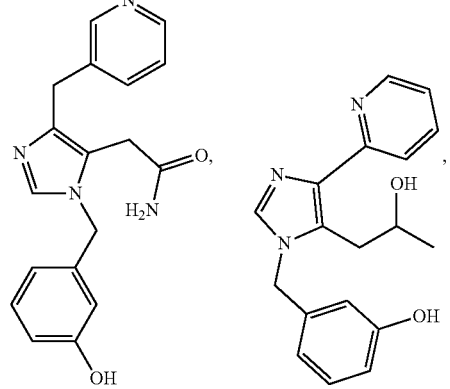
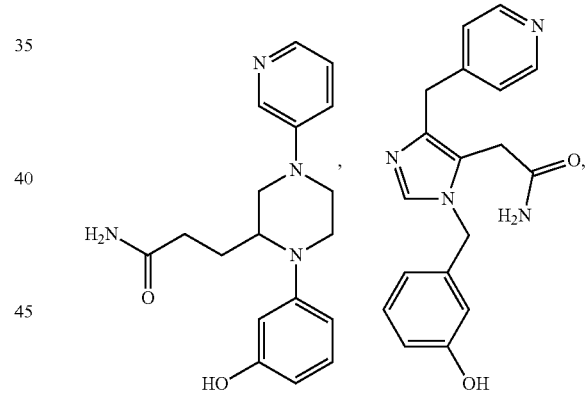
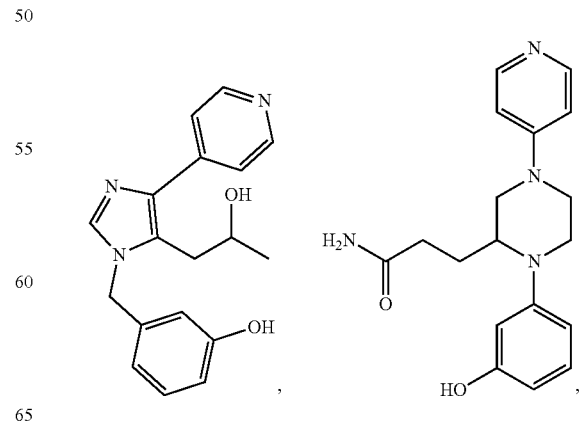

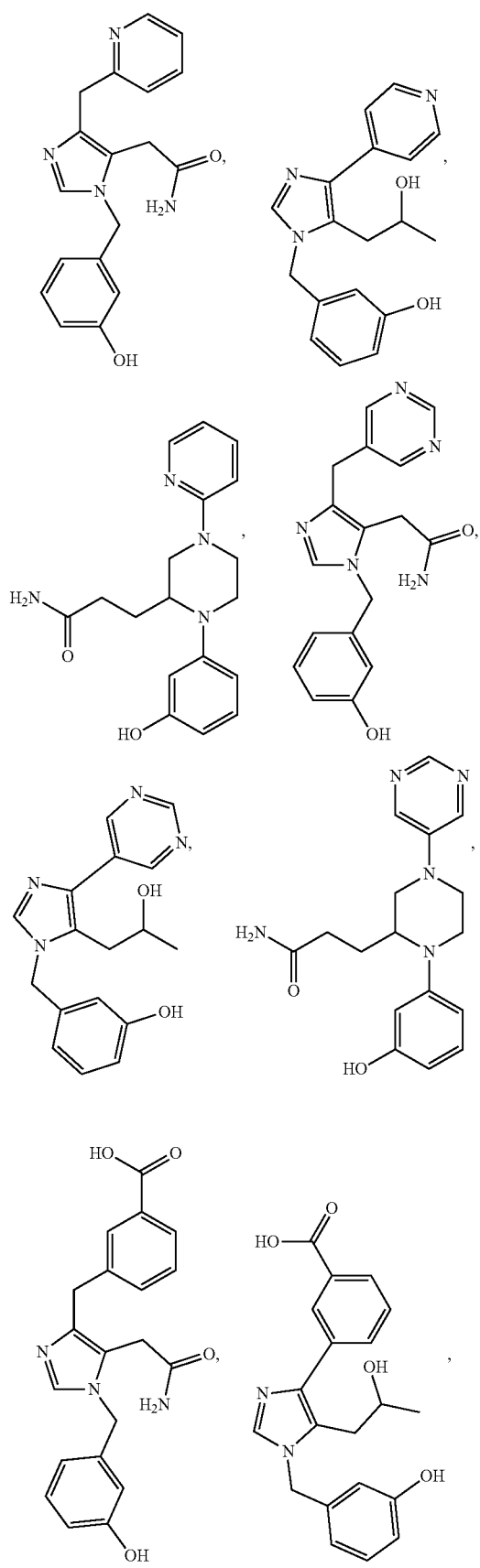
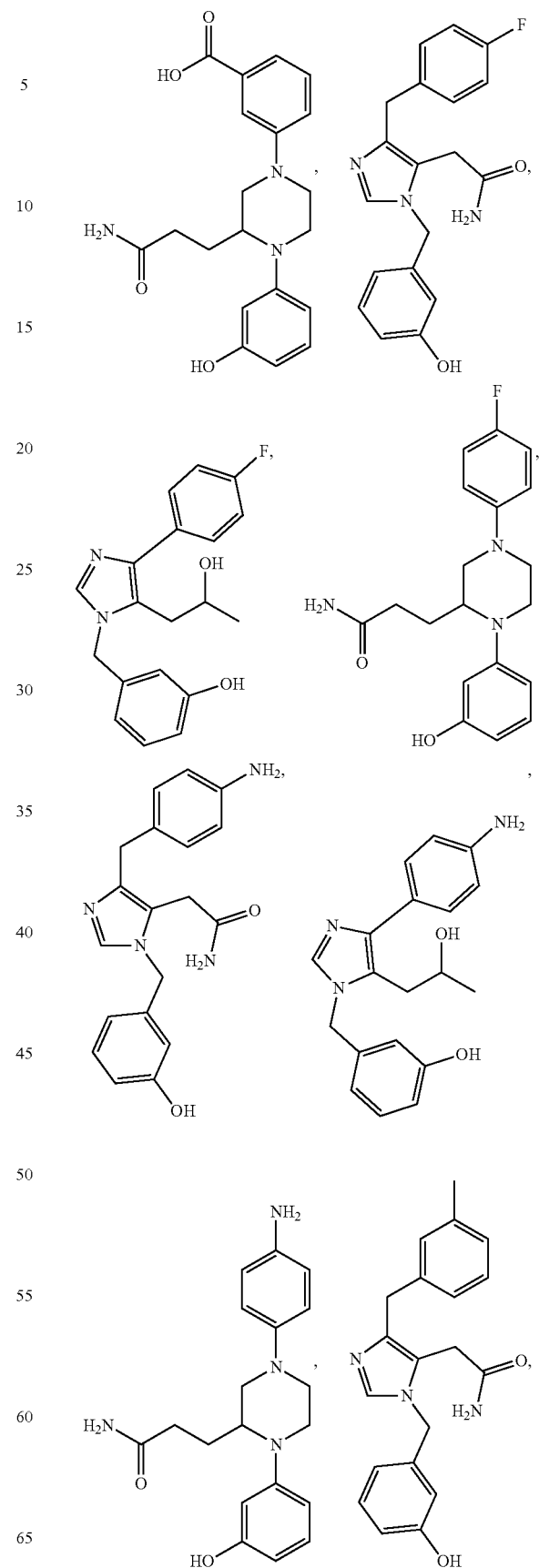

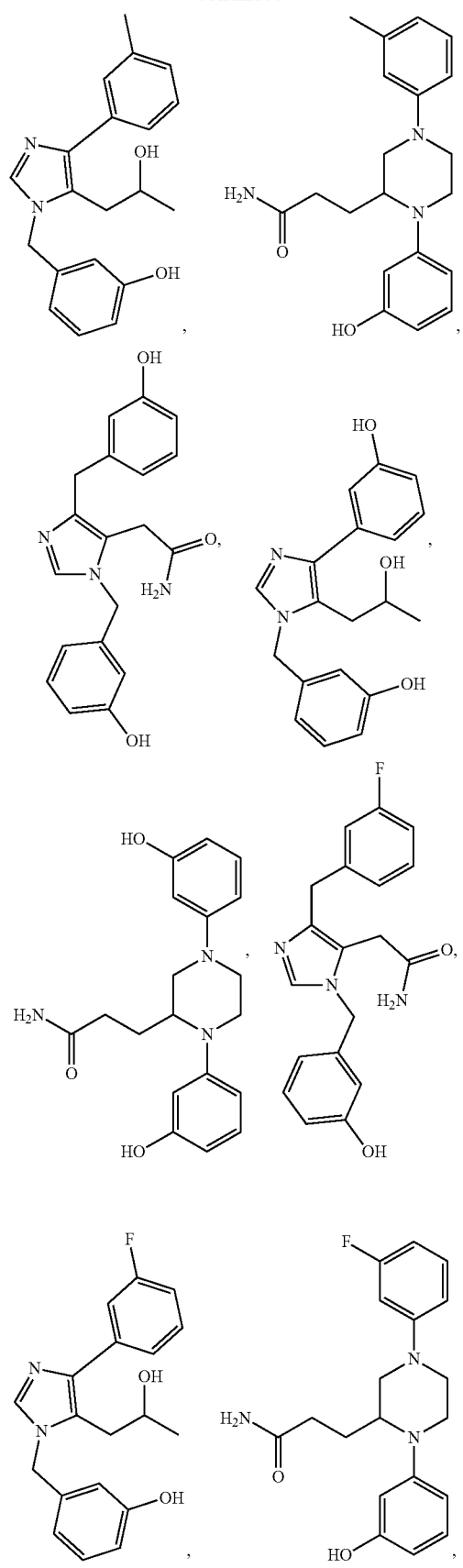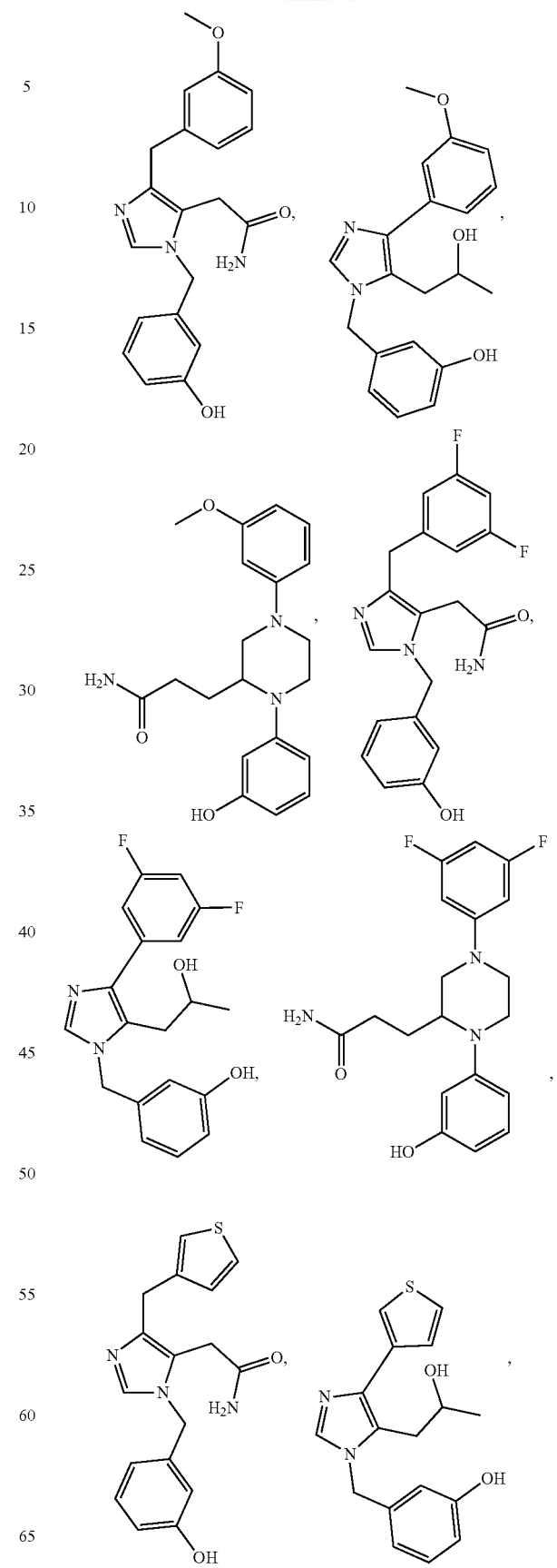

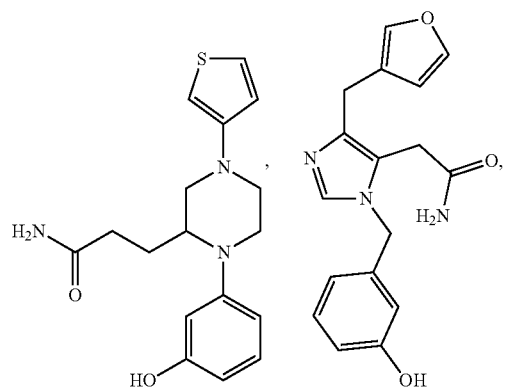
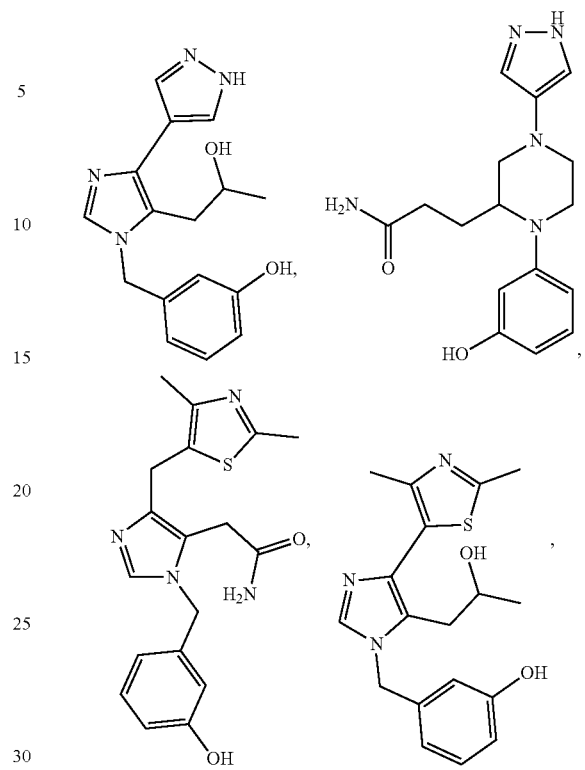
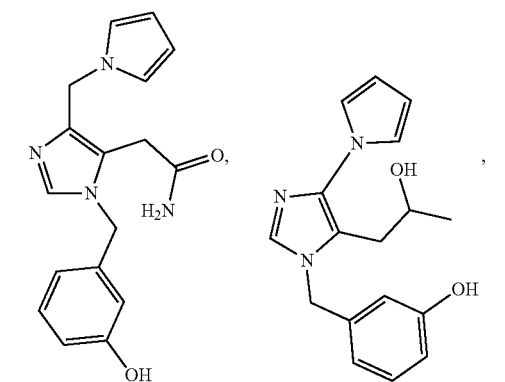
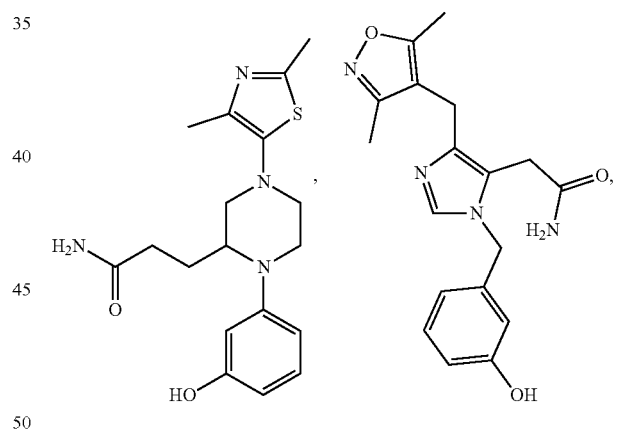
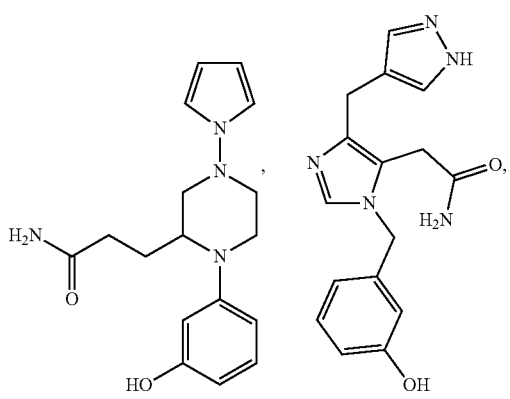
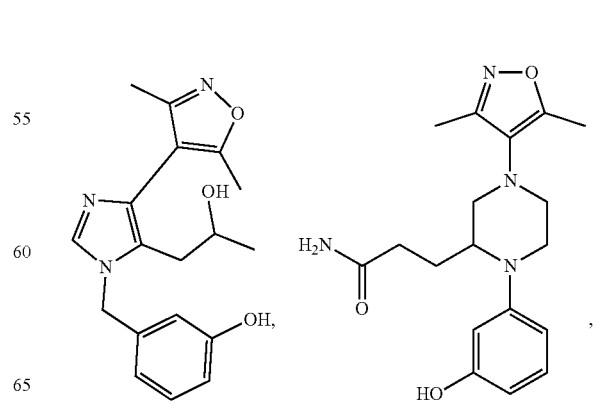

87
-continued
88
-continued
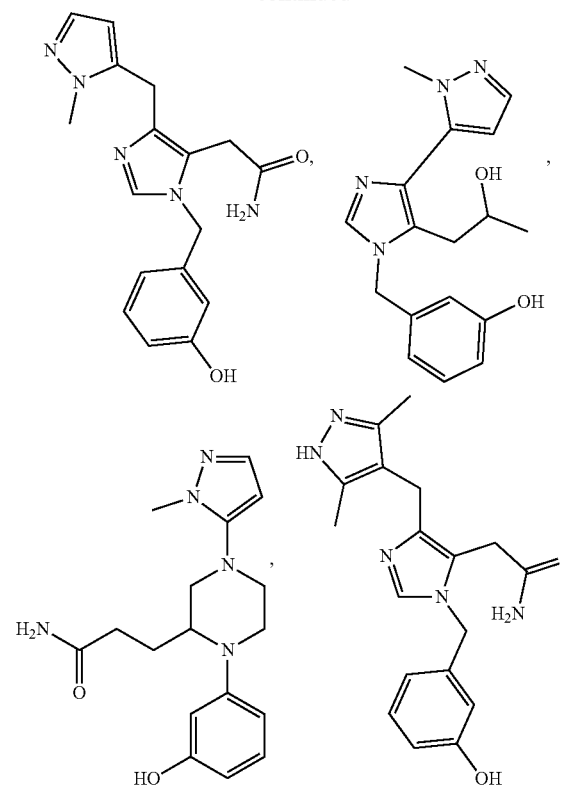
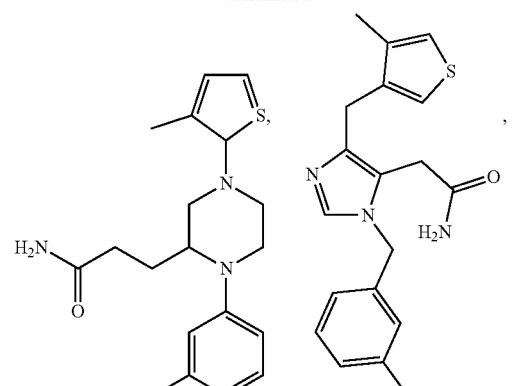
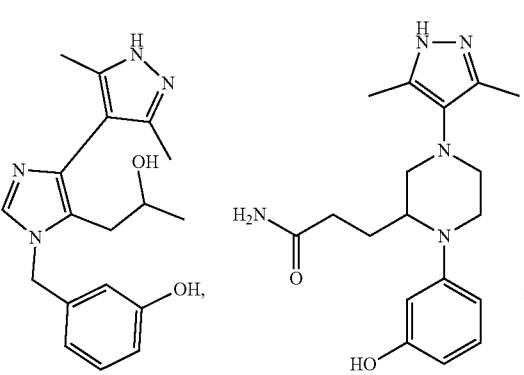
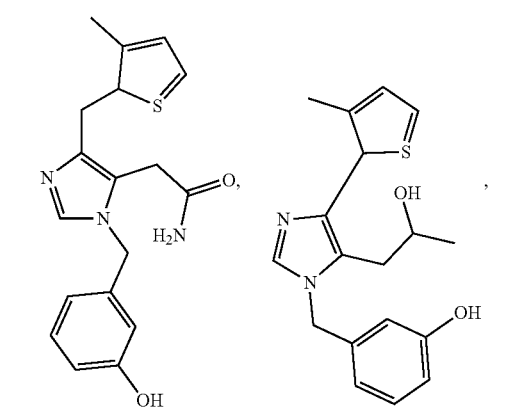

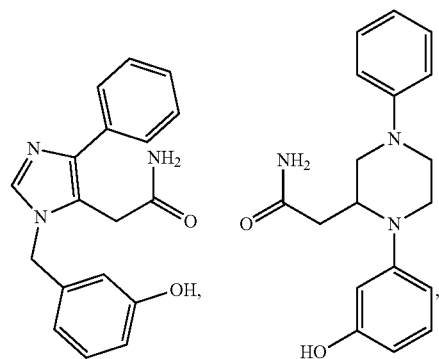
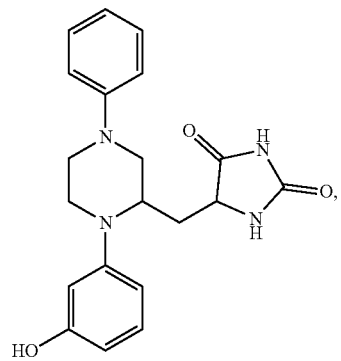
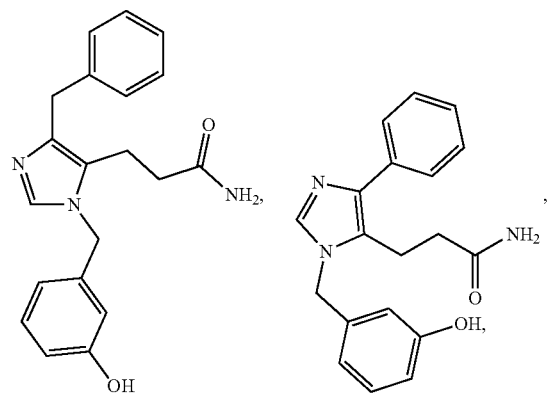
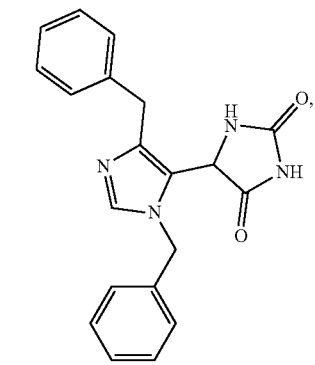
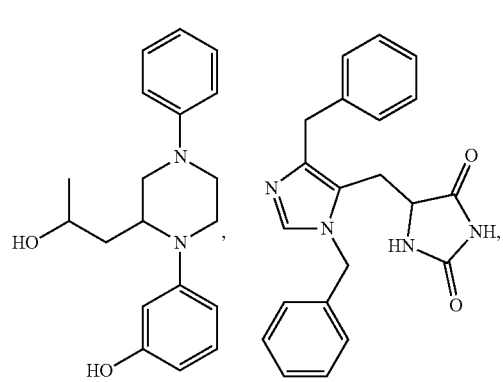
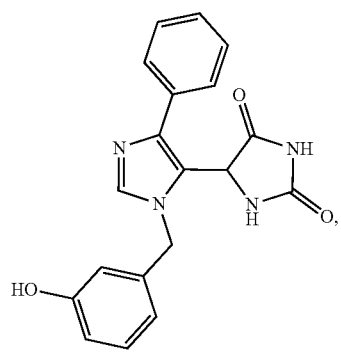
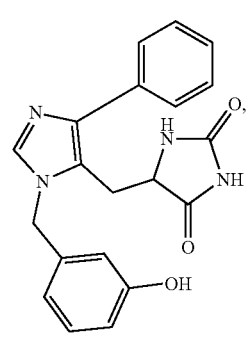
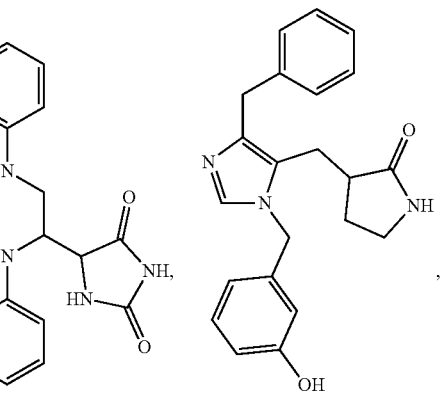

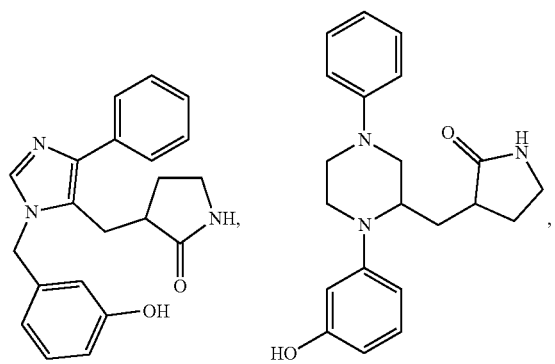
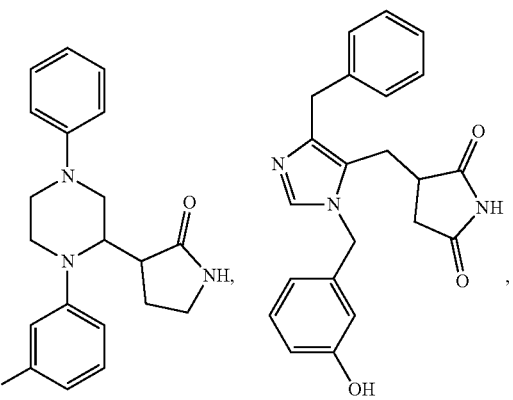
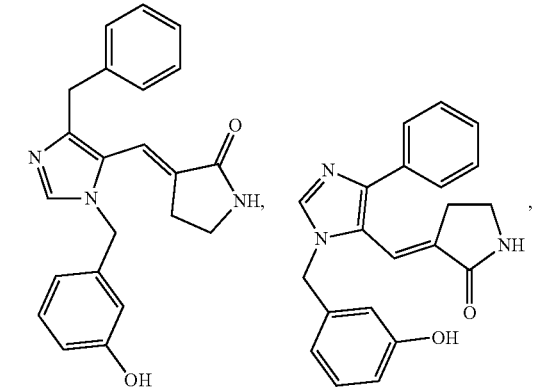
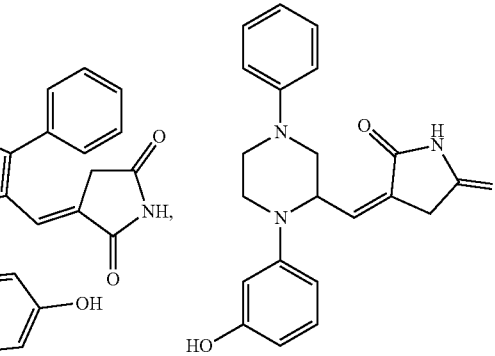
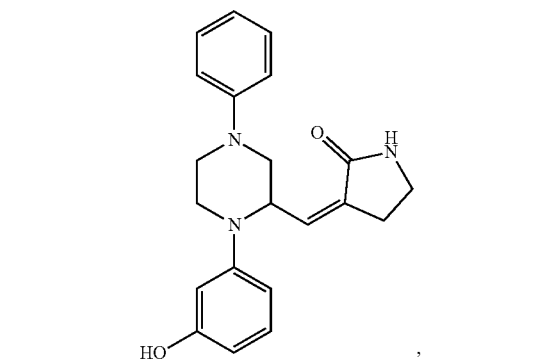
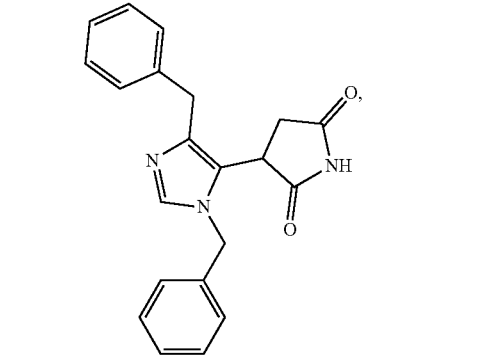
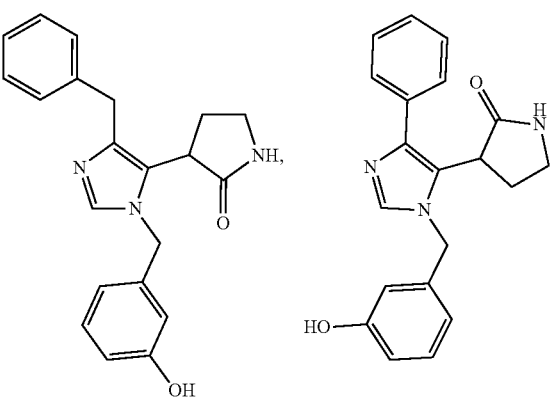
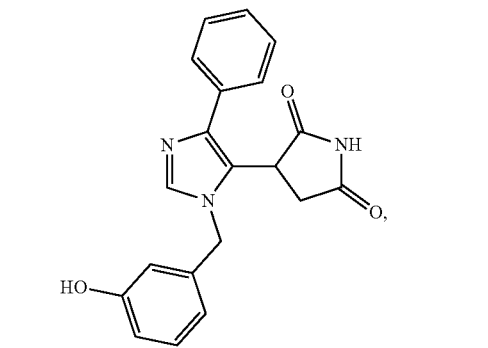

93
-continued
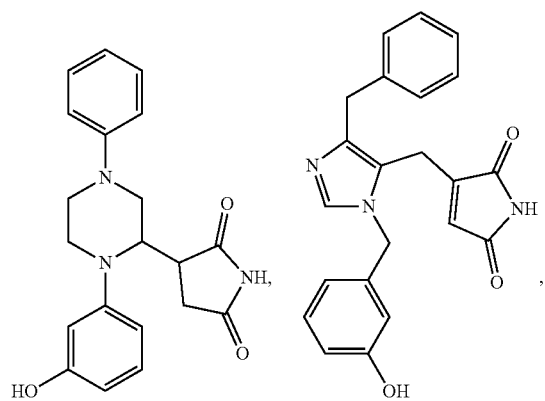
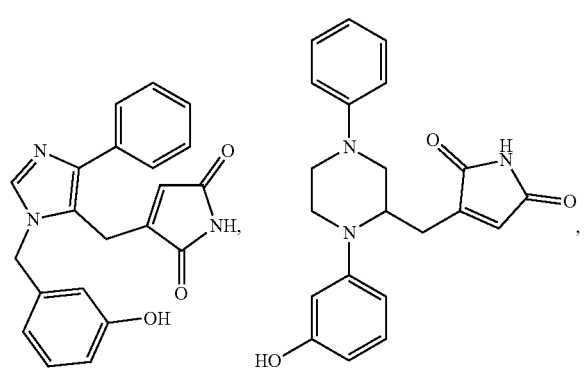
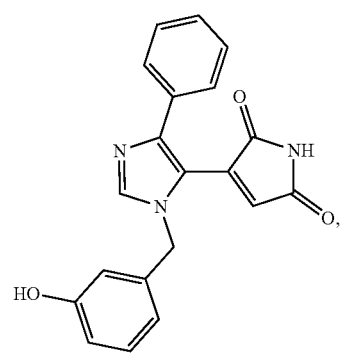
94
-continued
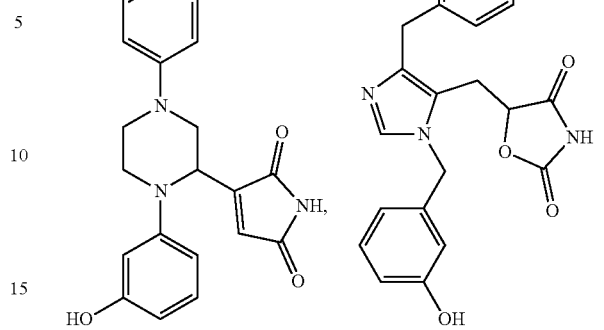
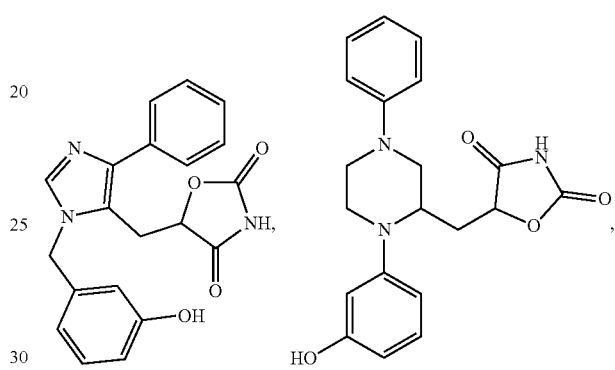
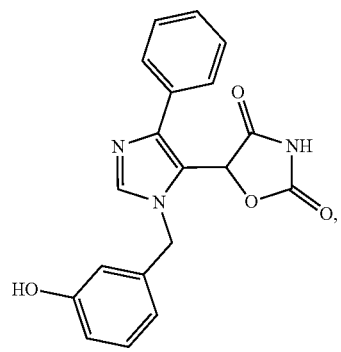

95
-continued
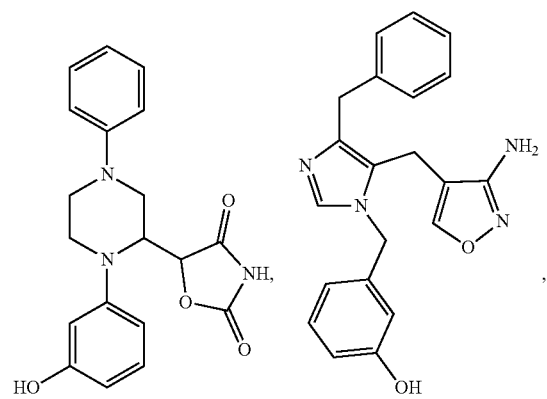
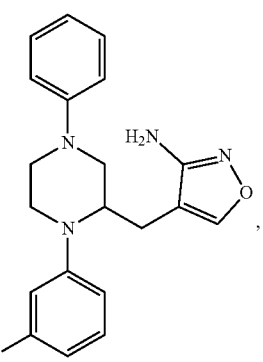
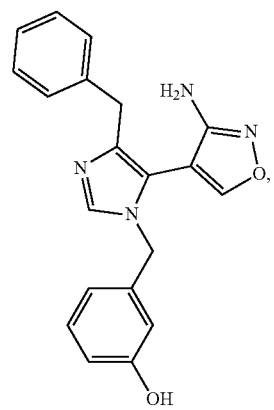
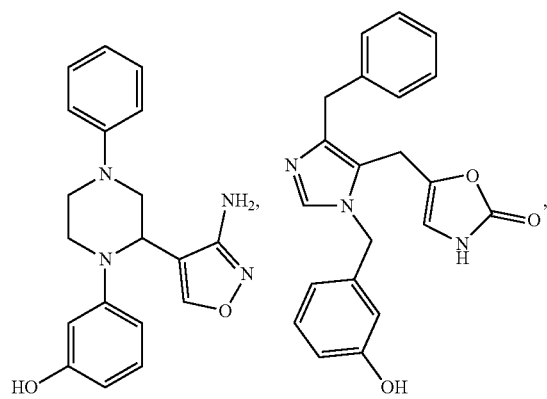
96
-continued
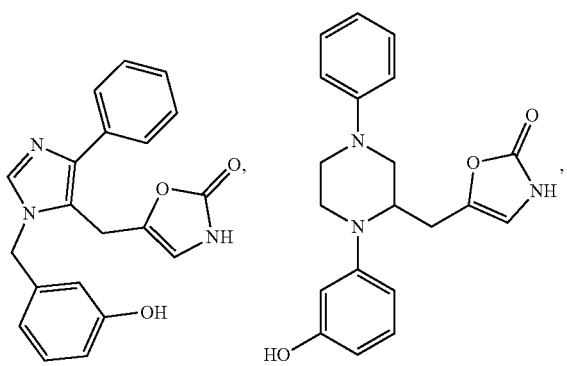
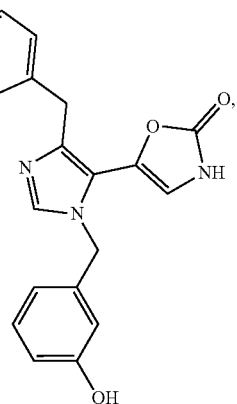
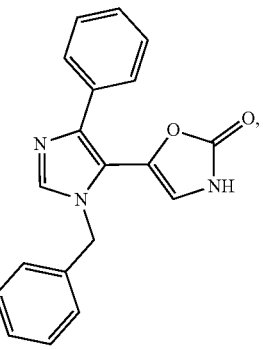
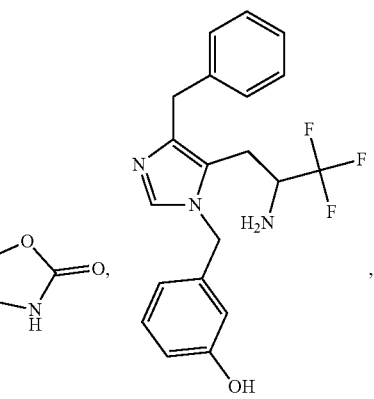

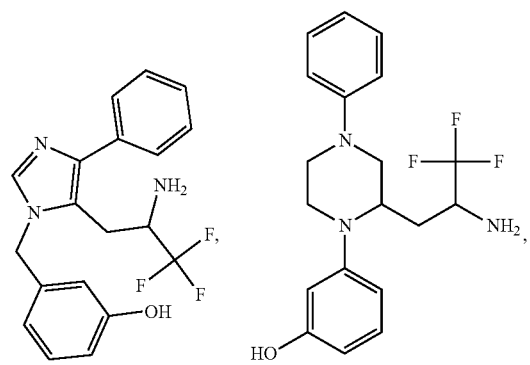
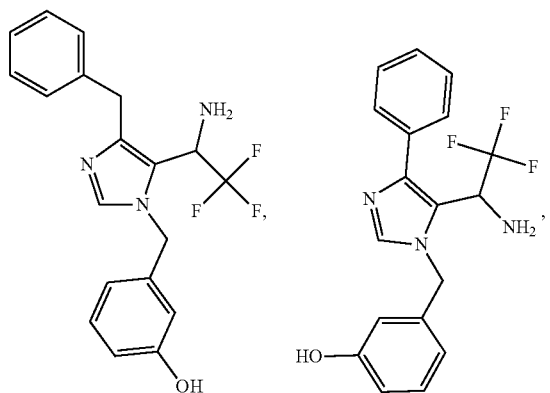
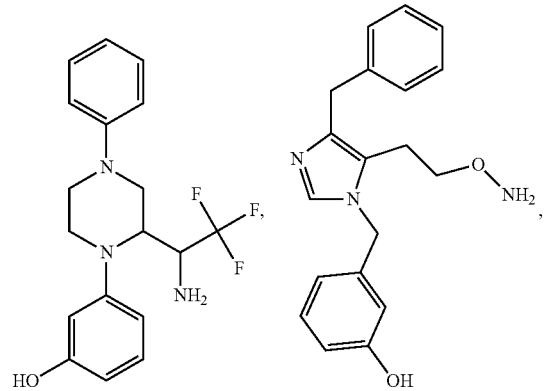
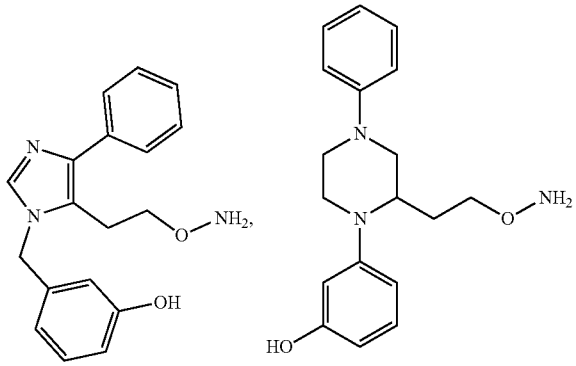
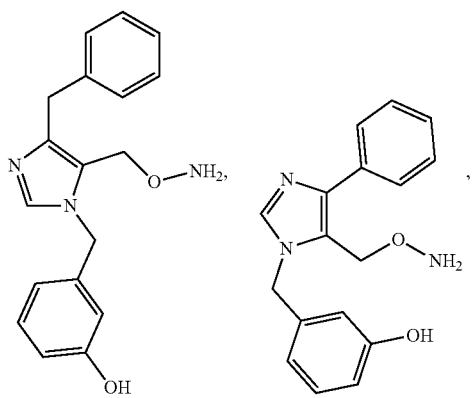
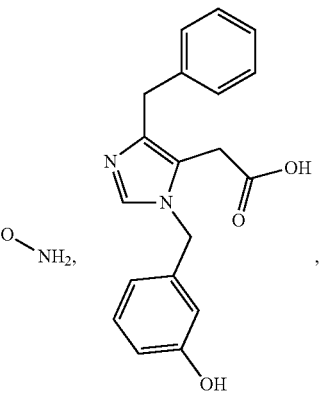
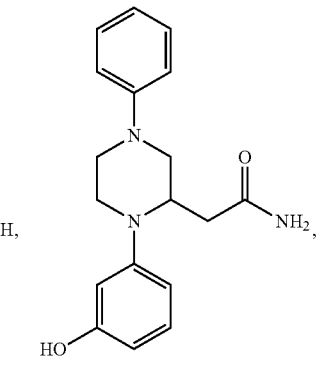
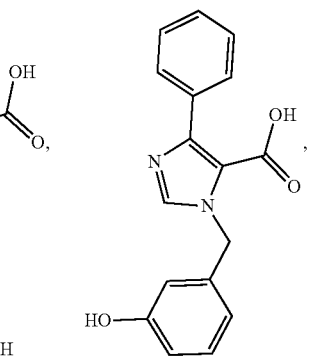

99
-continued
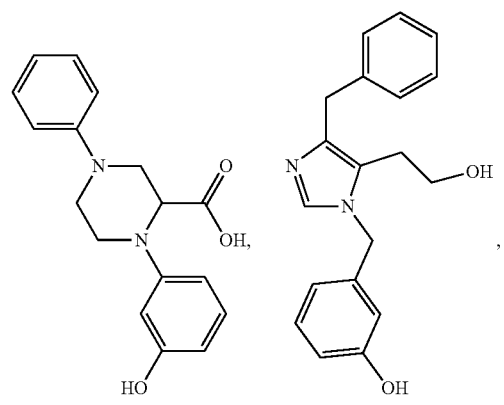
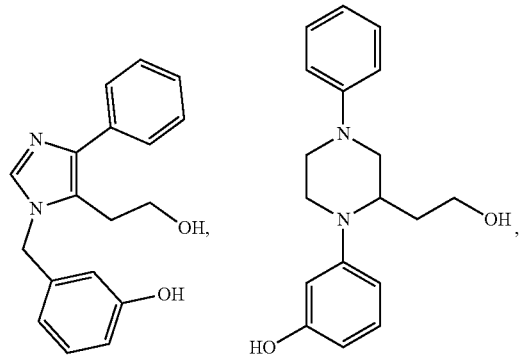
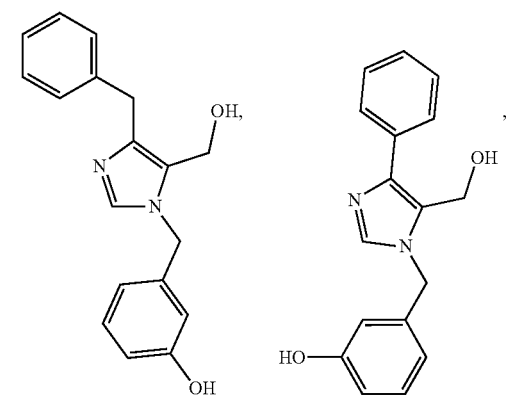
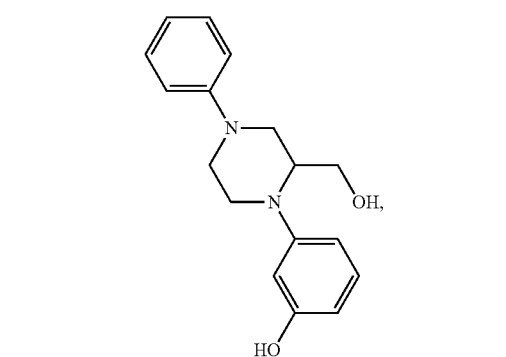
100
-continued
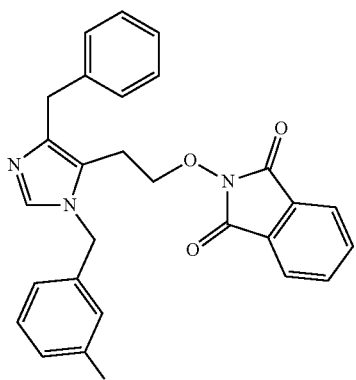
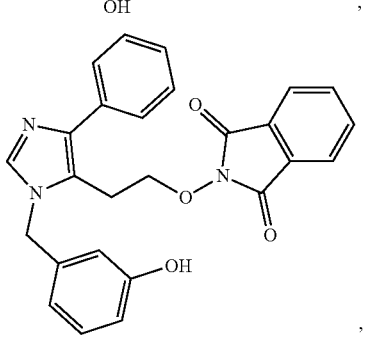
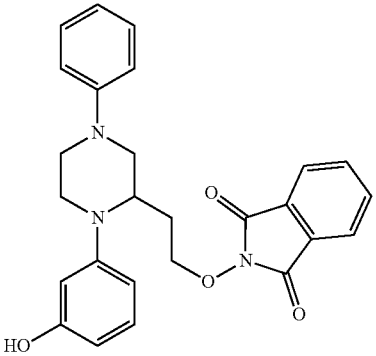
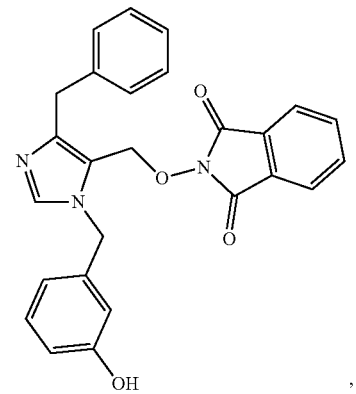

-continued

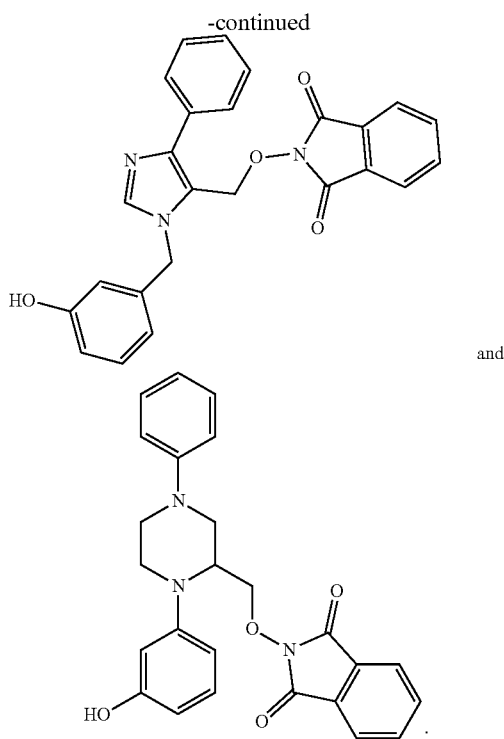

and

As used herein, the term "halo" designates —F, —Cl, —Br or —I; the term "hydroxy" means —OH; the term "amino" means —$NH_2$; and the term "substituted amino" includes —NHW, wherein W is selected from —CN, —$SO_2(X)_aY$ and —$CO(X)_aY$, a is 0 or 1, X is selected from —NH— and —O—, and Y is selected from —H, —$CH_3$, —$CH_2CH_3$, —$CH_2OH$ and —$CH_2CH_2OH$.

As used herein, the abbreviations Me, Et, Ph, Ms represent methyl, ethyl, phenyl, and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Compounds of the present invention may exist in particular geometric or stereoisomeric forms. The present invention contemplates all such compounds, including cis- and trans-isomers, (R)- and (S)-enantiomers, diastereomers, (d)-isomers, (l)-isomers, the racemic mixtures thereof, and other mixtures thereof, as falling within the scope of the invention. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, diastereomeric salts may be formed with an appropriate optically active acid or base, followed by resolution of the diastereomers thus formed by fractional crystallization or chromatographic means well known in the art, and subsequent recovery of the pure enantiomers.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

The present invention also contemplates pharmaceutically acceptable salts of the compounds. The term "pharmaceutically acceptable salt" includes both acid and base addition salts and refers to salts which retain the biological effectiveness and properties of the free bases or acids, and which are not biologically or otherwise undesirable. The pharmaceutically acceptable salts are formed with inorganic or organic acids or bases, and can be prepared in situ during the final isolation and purification of the compounds, or by separately reacting a purified compound in its free base or acid form with a suitable organic or inorganic acid or base, and isolating the salt thus formed.

The term "fibrosis" as used in the context of the present invention includes, but is not limited to, myocardial fibrosis, kidney fibrosis, liver fibrosis and/or lung fibrosis.

In addition to treatment of established fibrosis, the compounds of the present invention may be used prophylactically in subjects at risk of developing fibrosis. As an example of subjects in the risk category for developing fibrosis are those having hypertension, diabetes, myocarditis, ischaemic heart disease, Conn's Syndrome, pheochromocytoma, genetic predisposition high salt diet and/or receiving drugs used in cancer chemotherapy (such as daunorubicin). The term "prophylactic" as used in the context of the present invention is intended inter alia to encompass treatments used to prevent or slow down the development of fibrosis in the at risk group. Subjects who may be given prophylactic treatment may already have signs of early heart failure on echocardiography.

The term "hypertension" as used in the context of the present invention indicates an adult blood pressure of above about 139 mmHg systolic and/or above about 89 mmHg diastolic.

The term "prehypertension" as used in the context of the present invention indicates an adult blood pressure in the range about 120-139 mmHg systolic and/or about 80-89 mmHg diastolic.

The present invention also contemplates pharmaceutical compositions which include the compounds of the present invention, in conjunction with acceptable pharmaceutical excipients. The term "pharmaceutically acceptable excipient" as used in the context of the present invention means any pharmaceutically acceptable inactive component of the composition. As is well known in the art, excipients include diluents, buffers, binders, lubricants, disintegrants, colorants, antioxidants/preservatives, pH-adjusters, etc. The excipients are selected based on the desired physical aspects of the final form: e.g. obtaining a tablet with desired hardness and friability being rapidly dispersible and easily swallowed etc. The desired release rate of the active substance from the composition after its ingestion also plays a role in the choice of excipients. Pharmaceutical compositions may include any type of dosage form such as tablets, capsules, powders, liquid formulations, delayed or sustained release, patches, snuffs, nasal sprays and the like. The physical form and content of the pharmaceutical compositions contemplated are conventional preparations that can be formulated by those skilled in the pharmaceutical formulation field and are based on well established principles and compositions described in, for example, Remington: The Science and Practice of Pharmacy, 19th Edition, 1995; British Pharmacopoeia 2000 and similar formulation texts and manuals.

For example, where the compounds or compositions are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent.

When the compound(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The dosage of a compound and frequency of administration that should be used can also be easily determined by the practicing physician in order to produce the desired response.

Although the dosage will vary depending on the symptoms, age and body weight of the patient, the nature and severity of the disorder to be treated or prevented, the route of administration and the form of the drug, in general, a daily dosage of from 0.0001 mg to 200 mg of the compound of the present invention may be a suitable effective amount for an adult human patient, and this may be administered in a single dose or in divided doses.

A "patient" or "subject" to be treated by the subject method can mean either a human or non-human subject.

An "effective amount" of a subject compound, with respect to a method of treatment, refers to an amount of the therapeutic in a preparation which, when applied as part of a desired dosage regimen provides a benefit according to clinically acceptable standards for the treatment or prophylaxis of a particular disorder.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1—Synthesis of Compounds

The synthetic route used to prepare 2-[4-Benzyl-1-(3-hydroxybenzyl)-1H-imidazol-5-yl]acetamide (VB0002) is shown in FIG. 1. A condensation reaction between Boc-phenylalanine and methyl malonate potassium salt promoted by 1,1'-carbonyldiimidazole (CDI) gave the intermediate 4. Removal of the Boc group then provided compound 5 as a hydrochloride salt. The salt 5 was reacted with isothiocyanate B, and the cyclic thiourea 6 was obtained in low yield. Conversion of cyclic thiourea 6 to imidazole 7 was achieved under oxidative conditions. Treatment of imidazole 7 with aqueous ammonia afforded VB0002.

Figure 2:
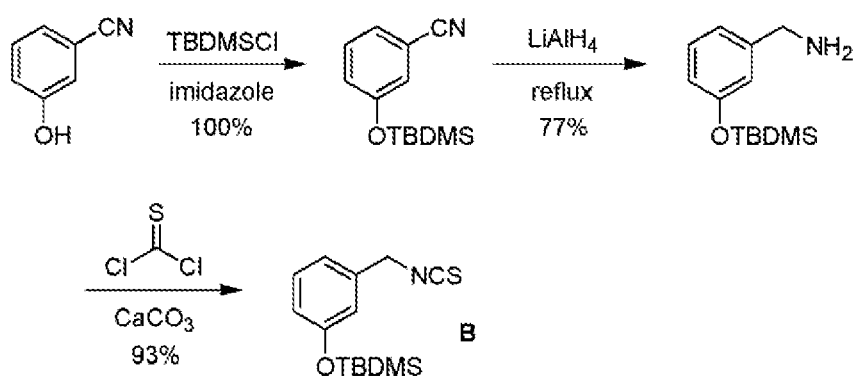
FIG. 2: Synthesis of 3-(tert-Butyldimethylsilyloxy)benzylisothiocyanate (compound B).

Compound B was not commercially available, and was prepared as shown in FIG. 2. 3-Cyanophenol was initially protected as a tert-butyldimethylsilyl ether, and the cyano group subsequently reduced to the corresponding amine, which was reacted with thiophosgene to form compound B.

Figure 3:
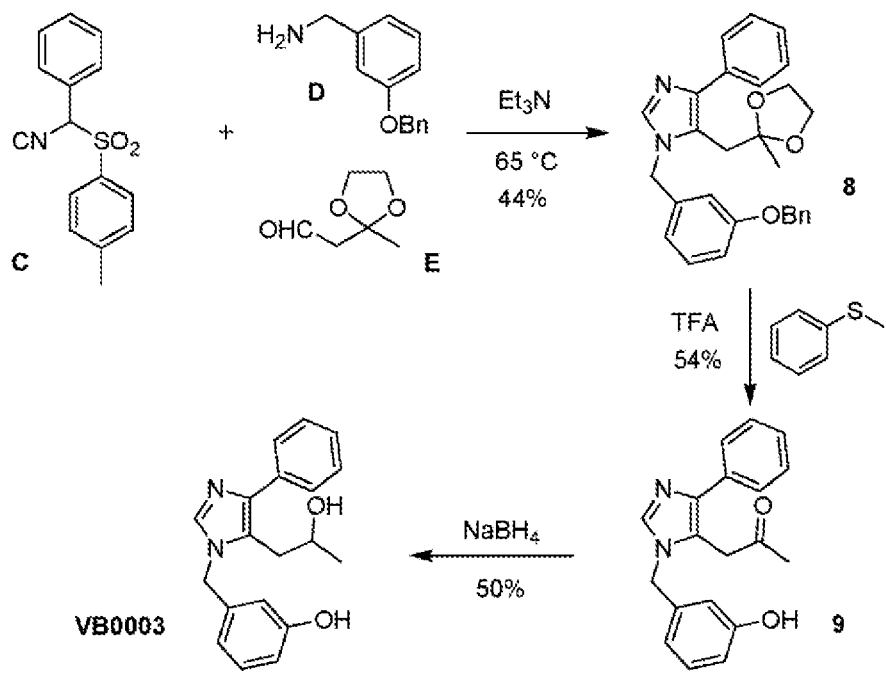
FIG. 3: Synthesis of 3-[5-(2-hydroxypropyl)-4-phenyl-imidazol-1-ylmethyl]-phenol (VB0003).

The synthetic route used to prepare 3-[5-(2-hydroxypropyl)-4-phenyl-imidazol-1-ylmethyl]-phenol (VB0003) is shown in FIG. 3. Firstly, imidazole 8 was conveniently assembled by a three-component coupling reaction of α-tosylbenzylisocyanide C, benzylamine D and the protected aldehyde E. Both protecting groups were subsequently removed using a thioanisole-trifluoroacetic acid (TFA) system to give compound 9, which was reduced to afford VB0003.

Figure 4:
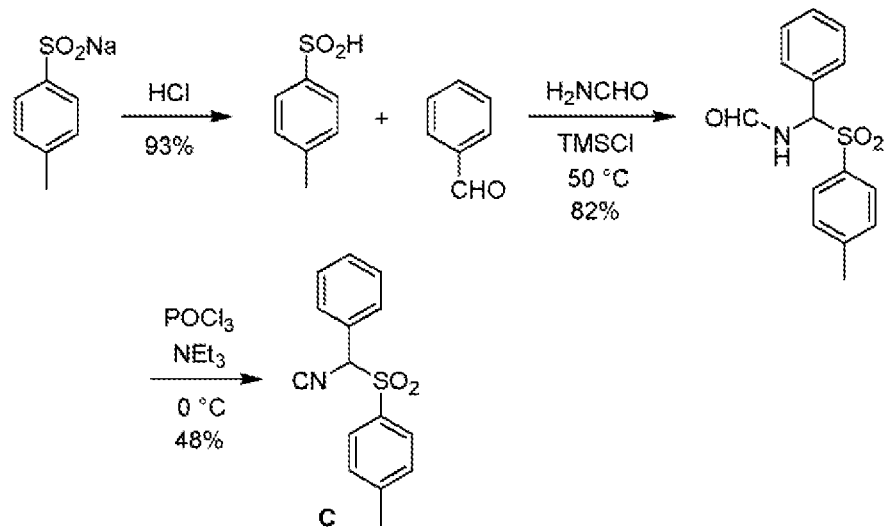
FIG. 4: Synthesis of α-Tosylbenzylisocyanide (compound C).

Compound C was prepared as shown in FIG. 4. 4-Toluenesulfinic acid, prepared from the corresponding sodium salt, was involved in a three-component reaction with benzaldehyde and formamide to form an intermediate which upon dehydration gave compound C.

Figure 5:
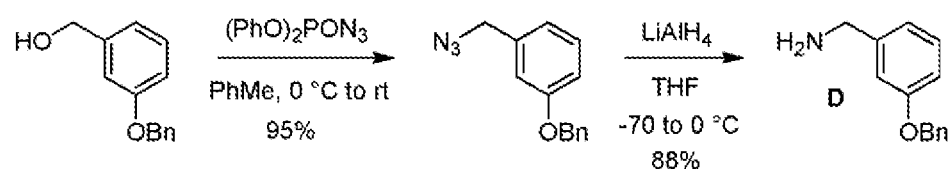
FIG. 5 Synthesis of 3-(Benzyloxy)benzylamine (compound D).

Compound D was not commercially available and was prepared as shown in FIG. 5. This was accomplished by converting 3-(benzyloxy)benzyl alcohol into the corresponding azide using diphenylphosphoryl azide, and subsequent reduction to give benzylamine D.

Figure 6:
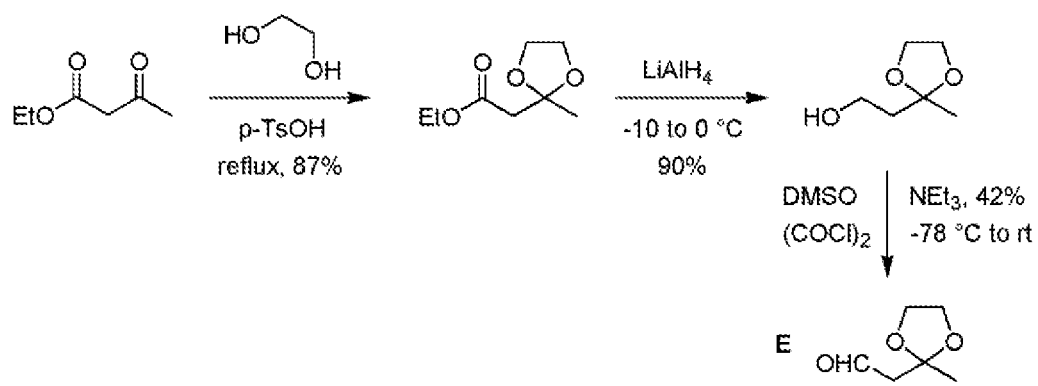
FIG. 6: Synthesis of 3,3-Ethylenedioxy-1-butanal (compound E).

Compound E was not commercially available and was prepared as shown in FIG. 6. Ethyl acetoacetate was initially protected as an acetal; the ester group was then reduced to a primary alcohol, which was subsequently subjected to a Swern oxidation to form protected aldehyde E.

Figure 7:
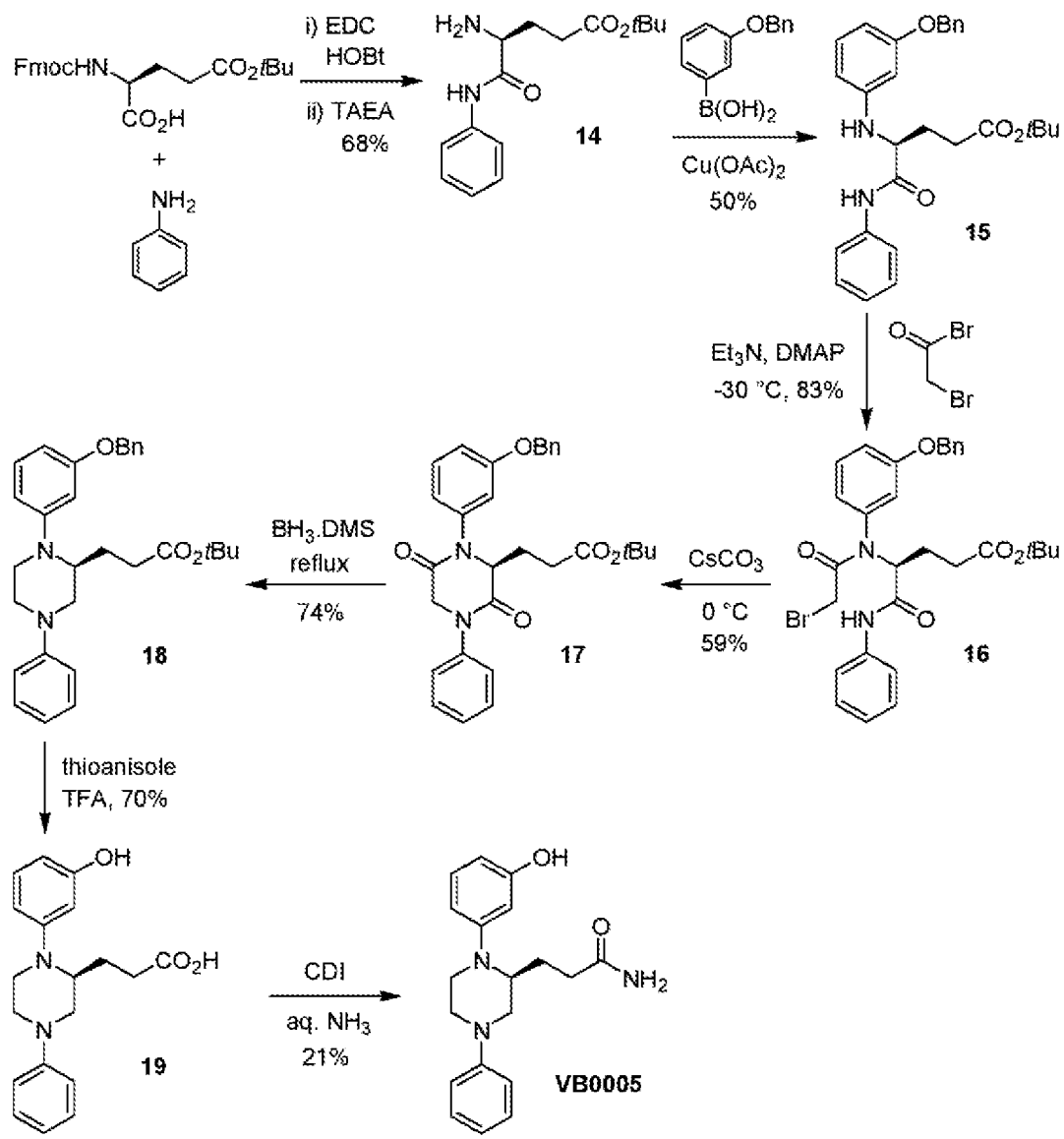
FIG. 7: Synthesis of (S)-3-[1-(3-Hydroxy)phenyl-4-phenylpiperazin-2-yl]propanamide (VB0005).

The synthetic route used to prepare (S)-3-[1-(3-Hydroxy)phenyl-4-phenylpiperazin-2-yl]propanamide (VB0005) is shown in FIG. 7. In a standard amide bond forming process Fmoc-L-glutamic acid 5-tert-butyl ester was reacted with aniline to form the corresponding amide, which was deprotected with tris(2-aminoethyl)amine (TAEA) to give compound 14. The free amine 14 underwent a copper-mediated cross-coupling reaction with 3-(benzyloxy)phenylboronic acid to afford the N-arylated product 15. This compound was subsequently reacted with bromoacetyl bromide to form compound 16, which was transformed into keto-piperazine 17; a selective reduction of this compound yielded piperazine 18. A subsequent double deprotection step employing a thioanisole-TFA system gave compound 19, which was subjected to an aminolysis reaction using aqueous ammonia and 1,1'-carbonyldiimidazole (CDI) to afford VB0005.

Methyl 4-(tert-butoxycarbonylamino)-3-oxo-5-phenylpentanoate (4)

A suspension of magnesium chloride (6.96 g, 73.0 mmol) and methyl malonate potassium salt (17.66 g, 113.2 mmol) was stirred in THF (280 mL) at 50° C., under a nitrogen atmosphere for 6 h. To a solution of N-(tert-butoxycarbonyl)-L-phenylalanine (20.0 g, 75.4 mmol) in THF (200 mL) in a separate flask, under nitrogen and at 0° C. was added portionwise 1,1'-carbonyldiimidazole (18.34 g, 113.1 mmol) and the reaction stirred at ambient temperature for 2 h, then added to the cooled malonate suspension. The reaction mixture was then stirred at room temperature for 17 h. Most of the THF was removed in vacuo. To the residue was added saturated potassium hydrogen sulphate (300 mL) and ethyl acetate (300 mL). The layers were separated then the aqueous layer was extracted twice more with ethyl acetate. The combined organic layers were washed with saturated sodium bicarbonate (2×300 mL) and brine (300 mL), dried and concentrated in vacuo to give methyl 4-(tert-butoxycarbonylamino)-3-oxo-5-phenylpentanoate (22.22 g, 92%) as a pale viscous oil which solidified. $^1$H NMR (400 MHz, CDCl$_3$) δ 7.33-7.08 (m, 5H), 5.20-4.80 (m, 1H), 4.62-4.48 (m, 1H), 3.69 (s, 3H), 3.52 (d, J=16.0 Hz, 1H), 3.45 (d, J=16.0 Hz, 1H), 3.25-2.88 (m, 2H), 1.39 (s, 9H). $^{13}$C NMR (100 MHz, CDCl$_3$) δ 201.8, 167.3, 155.2, 136.1, 129.2, 128.6, 126.9, 80.1, 60.4, 52.3, 46.5, 36.7, 28.2. EIMS: m/z 321 [M]$^+$. HRMS calcd for C$_{17}$H$_{23}$NO$_5$ 321.1576, found 321.1555.

Methyl 4-amino-3-oxo-5-phenylpentanoate hydrochloride (5)

Methyl 4-(tert-butoxycarbonylamino)-3-oxo-5-phenylpentanoate (22.20 g, 69.2 mmol) was stirred for 2 days with ethyl acetate saturated with hydrogen chloride. The resultant solid was collected by filtration, washed with diethyl ether and dried in the air to give methyl 4-amino-3-oxo-5-phenylpentanoate hydrochloride (16.25 g, 92%) as an unstable cream solid. $^1$H NMR (400 MHz, DMSO-d$_6$) δ 8.58 (br s, 3H), 7.37-7.20 (m, 5H), 4.49 (t, J=6.6 Hz, 1H), 3.83 (d, J=17.1 Hz, 1H), 3.74 (d, J=17.1 Hz, 1H), 3.62 (s, 3H), 3.22 (dd, J=14.4, 6.4 Hz, 1H), 3.11 (dd, J=14.4, 7.0 Hz, 1H).

Methyl 2-{5-benzyl-3-[3-(tert-butyldimethylsilyloxy)benzyl]-2-thioxo-2,3-dihydro-1H-imidazol-4-yl}acetate (6)

A mixture of methyl 4-amino-3-oxo-5-phenylpentanoate hydrochloride (7.15 g, 27.9 mmol), 3-(tert-butyldimethylsilyloxy)benzylisothiocyanate (9.34 g, 33.5 mmol), triethylamine (5.8 mL, 41.9 mmol) and pyridinium 4-toluenesulfonate (0.70 g, 2.8 mmol) in toluene (100 mL) was heated at a gentle reflux under nitrogen for 5 h. The reaction mixture was cooled to room temperature, then partitioned between water (150 mL) and ethyl acetate (150 mL). The layers were separated and the aqueous was extracted twice more with ethyl acetate. The combined organic layers were washed with water (2×150 mL), dried and concentrated in vacuo to give a tan oil. The crude material was dissolved in diethyl ether, seeded and left to crystallise for 20 h. Methyl 2-{5-benzyl-3-[3-(tert-butyldimethylsilyloxy)benzyl]-2-thioxo-2,3-dihydro-1H-imidazol-4-yl}acetate (2.14 g, 13%) was collected by filtration as a cream needles; mp 154.0-156.0° C. $^1$H NMR (400 MHz, CDCl$_3$) δ 9.68 (br s, 1H), 7.34-7.22 (m, 2H), 7.19-7.14 (m, 3H), 6.83-6.71 (m, 3H), 5.32 (s, 2H), 3.79 (s, 2H), 3.61 (s, 3H), 3.33 (s, 2H), 0.96 (s, 9H), 0.18 (s, 6H). $^{13}$C NMR (125 MHz, CDCl$_3$) δ 169.1, 161.5, 156.1, 137.4, 136.3, 129.9, 128.9, 128.6, 127.2, 125.8, 119.8, 119.5, 119.4, 118.6, 52.4, 47.9, 30.1, 29.6, 25.7, 18.2, −4.4. EIMS: m/z 482 [M]$^+$. HRMS calcd for C$_{26}$H$_{34}$N$_2$O$_3$SSi 482.2054, found 482.2039.

Methyl 2-{4-benzyl-1-[3-(tert-butyldimethylsilyloxy)benzyl]-1H-imidazol-5-yl}acetate (7)

To a suspension of methyl 2-{5-benzyl-3-[3-(tert-butyldimethylsilyloxy)benzyl]-2-thioxo-2,3-dihydro-1H-imidazol-4-yl}acetate (1.00 g, 2.1 mmol) in acetic acid (3.4 mL) under nitrogen, was slowly added 30% hydrogen peroxide (941 μL). After 10 min the reaction solution was cooled in an ice-bath and then quenched with 10% sodium carbonate (20 mL). The pH was adjusted to 9-10 with 1M sodium hydroxide, then extracted with ethyl acetate (3×20 mL), dried and concentrated in vacuo to give methyl 2-{4-benzyl-1-[3-(tert-butyldimethylsilyloxy)benzyl]-1H-imidazol-5-yl}acetate (0.86 g, 91%) as a tan oil. $^1$H NMR (400 MHz, CDCl$_3$) δ 7.50 (s, 1H), 7.27-7.10 (m, 6H), 6.80-6.74 (m, 1H), 6.69- 6.60 (m, 1H), 6.50-6.47 (m, 1H), 5.06 (s, 2H), 3.93 (s, 2H), 3.55 (s, 3H), 3.38 (s, 2H), 0.95 (s, 9H), 0.14 (s, 6H). $^{13}$C NMR (50 MHz, CDCl$_3$) δ 170.0, 156.3, 139.9, 139.6, 137.3, 136.2, 130.1, 128.6, 128.4, 126.0, 120.4, 119.8, 118.4, 117.4, 52.2, 48.9, 33.5, 29.1, 25.6, 18.0, −4.5. EIMS: m/z 450 [M]$^+$. HRMS calcd for C$_{26}$H$_{34}$N$_2$O$_3$Si, 450.2333, found 450.2323.

2-[4-Benzyl-1-(3-hydroxybenzyl)-1H-imidazol-5-yl]acetamide (VB0002)

To a solution of methyl 2-{4-benzyl-1-[3-(tert-butyldimethylsilyloxy)benzyl]-1H-imidazol-5-yl}acetate (0.86 g, 1.9 mmol) in methanol (2 mL) was added 25% aqueous ammonia solution. The flask was stoppered and the reaction mixture stirred at room temperature for 3 days. More methanol and diethyl ether were added and the reaction mixture stirred for 2 h. The fine precipitate was collected by filtration, washing well with diethyl ether, then air dried to give 2-[4-benzyl-1-(3-hydroxybenzyl)-1H-imidazol-5-yl]acetamide (0.193 g, 32%) as a colourless solid; mp 249° C. (dec.). $^1$H NMR (400 MHz, DMSO-d$_6$) δ 9.44 (s, 1H), 7.52 (s, 1H), 7.37 (br s, 1H), 7.24-7.07 (m, 5H), 6.95 (br s, 1H), 6.66 (m, 1H), 6.53-6.49 (m, 1H), 6.45-6.43 (m, 1H), 5.10 (s, 2H), 3.76 (s, 2H), 3.30 (s, 2H). $^{13}$C NMR (50 MHz, DMSO-d$_6$) δ 170.8, 157.7, 141.1, 138.9, 137.9, 136.9, 129.7, 128.5, 127.9, 125.5, 112.0, 117.3, 114.5, 113.5, 47.7, 32.8, 29.6. EIMS: m/z 321 [M]$^+$. HRMS calcd for C$_{19}$H$_{19}$N$_3$O$_2$ 321.1477, found 321.1470.

3-(tert-Butyldimethylsilyloxy)benzonitrile

To a stirred solution of 3-cyanophenol (10.34 g, 86.8 mmol) and imidazole (14.77 g, 217 mmol) in DMF (100 mL) under nitrogen, and at 0° C. was added portionwise tert-butyldimethylsilylchloride (13.74 g, 91 mmol) over 5 min. The reaction was allowed to warm to ambient temperature and was stirred for another 2 h. The reaction mixture was transferred to a separatory funnel and was partitioned between diethyl ether (150 mL) and water (150 mL). The layers were separated and the aqueous was extracted twice more with diethyl ether. The combined organic extracts were washed with water (2×100 mL), dried and concentrated to give 3-(tert-butyldimethylsilyloxy)benzonitrile (20.38 g, quantitative) as a pale yellow oil. $^1$H NMR (400 MHz, CDCl$_3$) δ 7.35-7.29 (m, 1H), 7.27-7.22 (m, 1H), 7.11-7.04 (m, 2H), 0.98 (s, 9H), 0.21 (s, 6H). $^{13}$C NMR (100 MHz, CDCl$_3$) δ 156.0, 130.4, 125.0, 124.9, 123.3, 118.5, 113.2, 25.5, 18.1, −4.6. EIMS: m/z 233 [M]$^+$. HRMS calcd for C$_{13}$H$_{19}$NOSi 233.1236, found 233.1227.

3-(tert-Butyldimethylsilyloxy)benzylamine

A mixture of lithium aluminium hydride (4.97 g, 131 mmol) and diethyl ether (400 mL) was heated at reflux for 1 h, then cooled to ambient temperature. A solution of 3-(tert-butyldimethylsilyloxy)benzonitrile (15.25 g, 65.5 mmol) in diethyl ether (50 mL) was added dropwise so that a gentle reflux was maintained. The reaction was then heated at reflux for 3 h and then cooled in an ice bath. Water (5 mL) was cautiously added dropwise, followed by 15% sodium hydroxide solution (5 mL) and then water (15 mL). The solids were filtered off and washed thoroughly with diethyl ether. The filtrate was washed with water, dried and concentrated in vacuo to give a pale yellow oil (14.68 g, 95%). The crude material was preabsorbed onto Celite, then chromatographed by DCVC eluting with a gradient of ethyl acetate in PE (5%-100% ethyl acetate) to give 3-(tert-butyldimethylsilyloxy)benzylamine (11.85 g, 77%) as a pale yellow oil. $^1$H NMR (400 MHz, CDCl$_3$) δ 7.13 (t, J=7.7 Hz, 1H), 6.84 (d, J=7.7 Hz, 1H), 6.79-6-75 (m, 1H), 6.68 (dd, J=8.0, 2.4 Hz, 1H), 3.75 (s, 2H), 0.97 (s, 9H), 0.18 (s, 6H). $^{13}$C NMR (100 MHz, CDCl$_3$) δ 155.5, 144.7, 129.1, 119.7, 118.5, 118.0, 46.0, 25.4, 17.9, −4.7. EIMS: m/z 237 [M]$^+$. HRMS calcd for C$_{13}$H$_{23}$NOSi 237.1543, found 237.1545.

3-(tert-Butyldimethylsilyloxy)benzylisothiocyanate (B)

A mixture of 3-(tert-butyldimethylsilyloxy)benzylamine (13.0 g, 54.8 mmol), calcium carbonate (5.65 g, 56.4 mmol), thiophosgene (8.5 mL, 111 mmol), water (41 mL) and chloroform (356 mL) was stirred vigorously at room temperature for 20 h in a stoppered flask. The reaction mixture was washed with water (2×250 mL), dried and concentrated in vacuo to give 3-(tert-butyldimethylsilyloxy)benzylisothiocyanate (14.29 g, 93%) as a pale tan oil. $^1$H NMR (400 MHz, CDCl$_3$) δ 7.27-7.21 (m, 1H), 6.92-6.88 (m, 1H), 6.83-6.79 (m, 2H), 4.65 (s, 2H), 1.00 (s, 9H), 0.22 (s, 6H). $^{13}$C NMR (100 MHz, CDCl$_3$) δ 156.1, 135.7, 132.4, 129.9, 120.0, 119.6, 118.5, 48.4, 25.6, 18.2, −4.4. EIMS: m/z 279 [M]$^+$. HRMS calcd for C$_{14}$H$_{21}$NOSi 279.1108, found 279.1105.

1-(3-Benzyloxybenzyl)-5-(2-methyl-1,3-dioxolan-2-yl-methyl)-4-phenyl-1H-imidazole (8)

To a solution of 3,3-ethylenedioxy-1-butanal (1.37 g, 10.5 mmol) in dry methanol (60 mL) was added 3-benzyloxybenzyl amine (2.10 g, 10.5 mmol) and the clear solution was allowed to stir at 25° C. for 90 min. α-Tosylbenzylisocyanide (2.86 g, 10.5 mmol) was added, followed by triethylamine (2.93 mL, 21.1 mmol), and the reaction mixture was stirred and heated at 65° C. for 4 h. The solvent was then removed and the residue dissolved in ethyl acetate (50 mL), washed with water (50 mL), dried and the solvent removed in vacuo. The residue was purified by column chromatography (gradient elution using 20-80% ethyl acetate/PE) to afford 1-(3-benzyloxybenzyl)-5-(2-methyl-[1,3]-dioxolan-2-yl-methyl)-4-phenyl-1H-imidazole (2.05 g, 44%) as a sticky pale orange oil. $^1$H NMR (200 MHz, CDCl$_3$) δ 7.89 (m, 2H) 7.58 (s, 1H), 7.21-7.7.44 (m, 9H), 6.90 (m, 1H), 6.65 (m, 2H), 5.31 (s, 2H), 5.01 (s, 2H), 3.83 (m, 2H), 3.59 (m, 2H), 3.02 (s, 2H), 1.33 (s, 3H). $^{13}$C NMR (50 MHz, CDCl$_3$) δ 159.2, 138.5, 137.6, 136.6, 135.3, 130.0, 128.6, 128.3, 128.0, 127.4, 127.2, 126.5, 119.0, 114.0, 113.1, 109.9, 69.9, 65.0, 48.8, 33.9, 29.7, 25.5. ESIMS: m/z 441 [M+H]$^+$. HRMS calcd for C$_{28}$H$_{28}$N$_2$O$_3$ 440.2094, found 440.2075.

1-[3-(3-hydroxybenzyl)-5-phenyl-3H-imidazol-4-yl]propan-2-one (9)

To a stirred solution of 1-(3-benzyloxybenzyl)-5-(2-methyl-[1,3]-dioxolan-2-yl-methyl)-4-phenyl-1H-imidazole (1.12 g, 2.54 mmol) in TFA (5 mL) was added thioanisole (598 μL, 5.09 mmol) and the reaction allowed to stir at 25° C. for 15 h. The reaction mixture was then cooled to 0° C., and water (30 mL) was slowly added followed by ethyl acetate (50 mL). The mixture was transferred to a separatory funnel and the aqueous layer removed. The organic phase was washed with water (2×50 mL), dried and the solvent removed in vacuo. The residue was then passed through a small plug of silica gel (90% ethyl acetate/PE), the solvent removed under reduced pressure, and recrystallised from chloroform/PE to give 1-[3-(3-hydroxybenzyl)-5-phenyl-3H-imidazol-4-yl]-propan-2-one (419 mg, 54%) as a white solid; mp 173.7-175.5° C. $^1$H NMR (200 MHz, CD$_3$CN) δ 8.52 (s, 1H), 7.48 (s, 5H), 7.25 (t, 1H, J=7.8 Hz), 6.79 (m, 3H), 5.16 (s, 2H), 3.94 (s, 2H), 2.14 (s, 3H). $^{13}$C NMR (50 MHz, CD$_3$OD) δ 204.6, 159.6, 136.7, 136.0, 134.5, 131.7, 131.1, 130.5, 129.2, 128.3, 126.0, 120.0, 117.1, 116.0, 52.1, 38.7, 29.5. ESIMS: m/z 307 [M+H]$^+$. HRMS calcd for C$_{19}$H$_{18}$N$_2$O$_2$ 306.1363, found 306.1365.

3-[5-(2-hydroxypropyl)-4-phenyl-imidazol-1-ylmethyl]-phenol (VB0003)

To an ice-cold solution of 1-[3-(3-Hydroxybenzyl)-5-phenyl-3H-imidazol-4-yl]propan-2-one (419 mg, 1.37 mmol) in dry methanol (50 mL) was added sodium borohydride (155 mg, 4.10 mmol) and the mixture allowed to stir at 25° C. for 15 h. Acetone (20 mL) was then added and the reaction mixture was stirred for a further 2 h. The solvent was then removed in vacuo; the residue was dissolved in ethyl acetate (50 mL), washed with water (50 mL) and the organic phase dried and the solvent removed under reduced pressure. The resulting solid was recrystallised from methanol, collected and washed with cold acetonitrile (4×) to afford 3-[5-(2-hydroxypropyl)-4-phenyl-imidazol-1-ylmethyl]-phenol (210 mg, 50%) as a white solid; mp 193-194° C. $^1$H NMR (200 MHz, CD$_3$OD) δ 7.72 (s, 1H), 7.62 (m, 2H), 7.39 (m, 2H), 7.28 (d, 1H, J=7.4 Hz), 7.18 (m, 1H), 6.72 (m, 1H), 6.65 (d, 2H, J=7.6 Hz), 6.54 (s, 1H), 5.34 (d, 1H, J=16.0 Hz), 5.24 (d, 1H, J=16.0 Hz), 3.90 (sextet, 1H), 2.82 (d, 2H, J=6.4 Hz), 1.05 (d, 3H, J=6.2 Hz). $^{13}$C NMR (50 MHz, CD$_3$OD) δ 159.3, 140.2, 139.8, 138.7, 136.4, 131.1, 129.5, 128.7, 127.9, 127.4, 118.9, 115.9, 114.6, 68.4, 34.1, 23.3. ESIMS: m/z 309 [M+H]$^+$. HRMS calcd for C$_{19}$H$_{20}$N$_2$O$_2$ 308.1519, found 308.1517. HPLC purity=98%.

4-Toluenesulfinic Acid

A 500 mL Erlenmeyer flask was charged with 4-toluenesulfinic acid sodium salt tetrahydrate (26.82 g, 0.11 mol) and water (134 mL) and stirred for 30 min until all the solid dissolved. tert-Butylmethyl ether (134 mL) was added to the stirred solution followed by the slow addition of 32% HCl (12.2 mL, 0.11 mol) over 5 min. The reaction was stirred for 30 min and transferred to a separatory funnel, and the organic phase separated and diluted with toluene (134 mL). The solvent was concentrated to ca. 50 mL on a rotary evaporator, after which heptane (40 mL) was added to give a solid that was collected using a Büchner funnel. Subsequent washing with heptane (50 mL) and drying under vacuum gave 4-toluenesulfinic acid (15.48 g, 93%) as a white solid.

N-(α-Tosylbenzyl)formamide

A 500 mL, three-necked, flask fitted with a reflux condenser was charged with acetonitrile (35 mL), toluene (35 mL), benzaldehyde (6.74 mL, 66 mmol), formamide (6.57 mL, 166 mmol) and TMSCl (9.18 mL, 72 mmol). After heating the reaction mixture for 4 h at 50° C. (internal temperature), 4-toluenesulfinic acid (15.48 g, 99 mmol) was added with stirring. Within 1 h a solid had formed and the reaction was stirred with a teflon stirring rod every 30 min for a period of 4 h. The reaction was then allowed to cool to room temperature, and tert-butylmethyl ether (35 mL) was added and the stirring continued for 5 min after which water (170 mL) was added. The solid was collected on a Buchner funnel, washed with tert-butylmethyl ether (2×50 mL) and dried in vacuo to give N-(α-tosylbenzyl)formamide (16.73 g, 82%). $^1$H NMR (200 MHz, DMSO-d$_6$) δ 9.77 (d, 1H, J=10.6 Hz) 7.96 (s, 1H), 7.71 (d, 2H, J=8.2 Hz), 7.54 (m, 2H), 7.42 (m, 5H), 6.38 (d, 1H, J=10.6 Hz), 2.41 (s, 3H).

α-Tosylbenzylisocyanide (C)

A 500 mL, three-necked, flask fitted with a thermometer was charged with N-(α-tosylbenzyl)formamide (16.73 g, 57.8 mmol) and dry THF (120 mL). Phosphorus oxychloride (10.78 mL, 116.0 mmol) was added via syringe and resulting solution allowed to stir for 5 min at 25° C. After cooling the solution to ca. 0° C. with an ice/salt bath, triethylamine (48.4 mL, 347.0 mmol) was added by means of a dropping funnel over 45 min whilst keeping the internal temperature below 10° C. After the triethylamine addition was complete, the reaction was stirred for 45 min at 5-10° C. (ice bath). Ethyl acetate (85 mL) then water (85 mL) was added to the reaction, the mixture stirred for 5 min and, after transferring the mixture to a separatory funnel, the aqueous layer removed. The organic phase was washed with water (2×85 mL), saturated sodium bicarbonate solution (85 mL), brine (50 mL) and concentrated under reduced pressure until a slurry remained. The residue was diluted with n-propanol (85 mL) and concentrated to half its original volume. The precipitate was cooled to 0° C. for 15 min, collected on a Buchner funnel, washed with n-propanol (2×50 mL) and dried in vacuo. This afforded α-tosylbenzylisocyanide (7.47 g, 48%) as a beige solid. $^1$H NMR (200 MHz, CDCl$_3$) δ 7.60 (d, 2H, J=8.2 Hz) 7.30-7.52 (m, 7H), 5.61 (s, 1H), 2.47 (s, 3H).

3-(Benzyloxy)benzyl Azide

To a stirred solution of 3-benzyloxybenzyl alcohol (5.0 g, 23.3 mmol) and diphenylphosphoryl azide (6.03 mL, 28.0 mmol) in dry toluene (40 mL) at 0° C., under an argon atmosphere, was added 1,8-diazabicyclo[5.4.0]undec-7-ene (3.83 mL, 25.6 mmol). The resulting mixture was allowed to warm to ambient temperature, and stirred for 18 h. The reaction mixture was washed with water (2×) and 5% HCl solution (1×), then dried and concentrated under reduced pressure. The crude material was filtered through a short column of silica, eluting with 4/96 ethyl acetate/pentane, to afford 3-(benzyloxy)benzyl azide (5.28 g, 95%) as a clear colourless oil. $^1$H NMR (200 MHz, CDCl$_3$) δ 7.48-7.22 (m, 6H); 6.99-6.86 (m, 3H); 5.07 (s, 2H); 4.30 (s, 2H). $^{13}$C NMR (50 MHz, CDCl$_3$) δ 159.4, 137.2, 137.0, 130.1, 128.8, 128.3, 127.7, 120.9, 114.9, 114.9, 70.3, 54.9. $v_{N=N=N}$/cm$^{-1}$ 2101.

3-(Benzyloxy)benzylamine(D)

3-(Benzyloxy)benzyl azide (1.0 g, 4.2 mmol) was dissolved in anhydrous THF (20 mL) and the solution cooled to −70° C. Solid lithium aluminium hydride (238 mg, 6.3 mmol) in THF (6 mL) was added dropwise under an argon atmosphere. After the addition, the reaction was allowed to warm to 0° C. and stirred for 1 h. The reaction was carefully quenched with water, then 1.0 M Rochelle's salt was added and extracted with diethyl ether (3×). The combined organic extracts were washed with brine (1×) then dried and concentrated to afford 3-(benzyloxy)benzylamine (787 mg, 88%) as a clear, pale yellow oil. Further purification was not required. $^1$H NMR (200 MHz, CDCl$_3$) δ 7.48-7.17 (m, 6H); 6.98-6.79 (m, 3H), 5.06 (s, 2H); 3.83 (s, 2H), 1.43 (br s, 2H).

Ethyl 3,3-ethylenedioxybutanoate

A mixture of ethyl acetoacetate (9.72 mL, 76.84 mmol), ethylene glycol (7.50 mL, 134.50 mmol) and p-toluenesulfonic acid (15 mg, 0.08 mmol) in benzene (125 mL) was heated at reflux under Dean-Stark conditions for 24 h. The reaction mixture was allowed to cool, then washed with 5% NaHCO$_3$ solution (1×) and water (2×), dried and concentrated to afford ethyl 3,3-ethylenedioxy-butanoate (11.67 g, 87%) as a clear, colourless oil. Further purification was not required. $^1$H NMR (200 MHz, CDCl$_3$) δ 4.16 (q, 2H, J=7.2 Hz); 3.97 (s, 4H); 2.66 (s, 2H); 1.50 (s, 3H); 1.26 (t, 3H, J=7.2 Hz). $^{13}$C NMR (100 MHz, CDCl$_3$) δ 169.7, 107.9, 65.0, 60.8, 44.5, 24.7, 14.4. $v_{C=O}$/cm$^{-1}$ 1741.

3,3-Ethylenedioxy-1-butanol

A solution of ethyl 3,3-ethylenedioxybutanoate (5.0 g, 28.70 mmol) in anhydrous THF (10 mL) was added dropwise under an argon atmosphere, to a suspension of lithium aluminium hydride (1.10 g, 28.70 mmol) in THF (50 mL) at −10° C. The reaction was stirred at 0° C. for 1.5 h, and then quenched with a 1.0 M solution of Rochelle's salt (75 mL). The mixture was extracted with diethyl ether (3×), then the combined organic extracts washed with brine (1×) then dried and concentrated to afford 3,3-ethylenedioxy-1-butanol (3.43 g, 90%) as a clear, pale yellow liquid. Further purification was not required. $^1$H NMR (200 MHz, CDCl$_3$) δ 3.99 (s, 4H), 3.76 (q, 2H, J=5.6 Hz), 2.78 (t, 1H, J=5.6 Hz), 1.95 (m, 2H), 1.36 (s, 3H).

3,3-Ethylenedioxy-1-butanal (E)

Into a dropping funnel was added dry DMSO (4.42 mL, 62.3 mmol) and dry dichloromethane (25 mL). This solution was added dropwise over a period of 10 min to a stirred solution of oxalyl chloride (2.64 mL, 31.14 mmol) in dry dichloromethane (75 mL) at −78° C. After 10 min, a solution of 2-(2-methyl-1,3-dioxolan-2-yl)ethanol (3.43 g, 26.0 mmol) in dry dichloromethane (25 mL) was added dropwise (by means of a dropping funnel) over a period of 10 min. The resultant solution was stirred at −78° C. for 15 min, and then triethylamine (14.47 mL, 103.8 mmol) was added dropwise via syringe. The cooling bath was removed and the reaction mixture allowed to stir for a further 30 min. Water (70 mL) was then added, and stirring continued for a further 10 min. The organic phase was separated, and the aqueous phase washed with dichloromethane (70 mL). The combined organics were washed with water (4×70 mL), dried and the solvent removed in vacuo. The residue was purified by filtration through a small plug of silica gel (dichloromethane) to give 2-(2-methyl[1,3]-dioxolan-2-yl)acetaldehyde (1.40 g, 42%) as a pale yellow oil. $^1$H NMR (200 MHz, CDCl$_3$) δ 9.75 (t, 1H, J=2.8 Hz), 4.04-3.98 (m, 4H), 2.71 (d, 2H, J=2.8 Hz), 1.43 (s, 3H).

(S)-tert-Butyl-(4-amino-5-oxo-5-phenylamino)pentanoate (14)

To a stirred solution of (S)-2-(9H-fluoren-9-ylmethoxycarbonylamino)-5-tert-butoxy-5-oxo-pentanoic acid (25.3 g, 57 mmol) in DMF (150 mL) was added N-(3-dimethylaminopropyl)-N-ethylcarbodiimide (12.08 g, 63 mmol), 1-hydroxybenzotriazole hydrate (8.51 g, 63 mmol) and aniline (5.2 mL, 57 mmol), and the reaction mixture allowed to stir at ambient temperature for 2 days. Water (300 mL) was added followed by ethyl acetate (300 mL). The mixture was transferred to a separatory funnel and the layers separated. The aqueous layer was extracted twice more with ethyl acetate. The combined organic layers were washed with water (2×300 mL), dried and the solvent removed in vacuo to give crude (S)-tert-butyl-4-(9H-fluoren-9-ylmethoxycarbonylamino)-5-oxo-5-(phenylamino)pentanoate as a yellow oil. It was used without purification in the next step. To a stirred solution of crude (S)-tert-butyl-4-(9H-fluoren-9-yl-methoxycarbonylamino)-5-oxo-5-(phenylamino)pentanoate in dichloromethane (300 mL) was added tris(2-aminoethyl) amine (40 mL, 267 mmol) and the reaction mixture stirred at ambient temperature for 1-2 h. The reaction mixture was then washed with pH 5.5 phosphate buffer (2×200 mL), then water (200 mL), dried and the solvent removed in vacuo. The residue was dissolved in dichloromethane and an insoluble by-product was removed by filtration. The solution was preabsorbed onto Celite, then chromatographed (DCVC) eluting with gradient of chloroform in PE, and then a gradient of ethyl acetate in chloroform. Like fractions were combined to give (S)-tert-butyl-(4-amino-5-oxo-5-phenylamino)pentanoate (10.85 g, 68%) as pale yellow oil. $^1$H NMR (400 MHz, CDCl$_3$) δ 9.41 (br s, 1H), 7.63-7.55 (m, 2H), 7.37-7.28 (m, 2H), 7.12-7.07 (m, 1H), 3.51 (dd, J=7.6, 5.0 Hz, 1H), 2.49-2.34 (m, 2H), 2.26-2.15 (m, 1H), 1.96-1.84 (m, 1H), 1.66 (br s, 2H), 1.45 (s, 9H). $^{13}$C NMR (50 MHz, CDCl$_3$) δ 172.8, 172.6, 137.7, 129.0, 124.1, 119.4, 80.8, 55.2, 32.2, 30.2, 28.1. EIMS: m/z 278 [M]$^+$. HRMS calcd for $C_{15}H_{22}N_2O_3$ 278.1625, found 278.1612.

(S)-tert-butyl 4-[(3-benzyloxy)phenylamino]-5-oxo-5-(phenylamino)pentanoate (15)

A solution of 3-(benzyloxy)phenylboronic acid (7.05 g, 30.0 mmol) in toluene (150 mL) was azeotropically refluxed for 2.5 h, under nitrogen, to form 2,4,6-tris(3-benzyloxy)phenyl)-1,3,5,2,4,6-trioxatriborinane. Toluene was removed in vacuo and to the residue, at ambient temperature, was added a solution of (S)-tert-butyl-(4-amino-5-oxo-5-phenylamino)pentanoate (4.30 g, 15.5 mmol) in dichloromethane (100 mL), pyridine (2.5 mL, 30.9 mmol) and anhydrous copper(II) acetate (4.64 g, 23.2 mmol). The reaction mixture was opened to the air and allowed to stir at ambient temperature for 2 days. The reaction mixture was then poured onto a short column packed with silica gel and topped with a layer of Celite. The crude product was eluted with chloroform and fractions containing the crude product were combined. The crude material was preabsorbed onto Celite and then purified by silica gel DCVC eluting with a gradient of chloroform in PE (60-100% chloroform) to give (S)-tert-butyl 4-[(3-benzyloxy)phenylamino]-5-oxo-5-(phenylamino)pentanoate (3.35 g, 50%) as a pale tan oil. $^1$H NMR (400 MHz, CDCl$_3$) δ 8.69 (br s, 1H), 7.57-7.48 (m, 2H), 7.46-7.23 (m, 7H), 7.15-7.06 (m, 2H), 6.49-6.42 (m, 1H), 6.33-6.24 (m, 2H), 5.06-5.02 (m, 1H), 5.00 (s, 2H), 3.80-3.72 (m, 1H), 2.67-2.54 (m, 1H), 2.49-2.37 (m, 1H), 2.36-2.24 (m, 1H), 2.21-2.09 (m, 1H), 1.46 (s, 9H). $^{13}$C NMR (50 MHz, CDCl$_3$) δ 173.6, 171.3, 160.0, 148.2, 137.3, 136.9, 130.2, 128.9, 128.5, 127.8, 127.4, 124.4, 119.9, 106.8, 105.5, 100.8, 81.3, 69.8, 61.1, 32.7, 28.0, 27.8. EIMS: m/z 460 [M]$^+$. HRMS calcd for $C_{28}H_{32}N_2O_4$ 460.2357, found 460.2341.

(S)-tert-butyl 4-[N-(3-benzyloxy)phenyl-2-bromoacetamido]-5-oxo-5-(phenylamino)pentanoate (16)

To a stirred solution of (S)-tert-butyl 4-(3-benyloxyphenylamino)-5-oxo-5-(phenylamino)pentanoate (4.05 g, 8.80 mmol) in dichloromethane (80 mL), under nitrogen and at −30° C. was added sequentially triethylamine (1.22 mL, 8.80 mmol), N,N-dimethylaminopyridine (20 mg) and bromoacetyl bromide (941 □L, 10.80 mmol). The reaction mixture was allowed to warm up to ambient temperature and then stirred for 30 min. The reaction mixture was transferred to a separatory funnel, washed with 10% citric acid (50 mL) and brine (2×50 mL), dried and the solvent removed in vacuo. The residue was preabsorbed onto Celite, then purified by silica gel DCVC to (S)-tert-butyl 4-[N-(3-benzyloxy)phenyl-2-bromoacetamido]-5-oxo-5-(phenylamino)pentanoate (4.28 g, 83%) as a pale yellow oil. $^1$H NMR (400 MHz, CDCl$_3$) δ 8.61 (br s, 1H), 7.63-7.53 (m, 2H), 7.49-7.21 (m, 8H), 7.17-7.09 (m, 1H), 7.08-7.02 (1H), 6.89-6.84 (m, 2H), 5.21 (dd, J=8.8, 6.2 Hz, 1H), 5.04 (br s, 2H), 3.64 (dd, J=19.7, 11.2 Hz, 2H), 2.44-2.19 (m, 2H), 2.05-1.91 (m, 1H), 1.80-1.67 (m, 1H), 1.43 (s, 9H). $^{13}$C NMR (50 MHz, CDCl$_3$) δ 171.8, 168.2, 167.8, 159.4, 138.3, 137.8, 136.1, 130.4, 128.9, 128.5, 128.1, 127.5, 124.3, 121.4, 119.9, 116.6, 115.5, 80.7, 70.2, 59.4, 31.8, 28.0, 27.4, 23.9. EIMS: m/z 581 [M]$^+$. HRMS calcd for $C_{30}H_{33}BrN_2O_5$ 580.1567, found 580.1547.

(S)-tert-Butyl 3-[1-(3-benzyloxy)phenyl-3,6-dioxo-4-phenylpiperazine-2-yl]propanoate (17)

To a stirred solution of (S)-tert-butyl 4-[N-(3-benzyloxy)phenyl-2-bromoacetamido]-5-oxo-5-(phenylamino)pentanoate (4.15 g, 7.15 mmol) in DMF (70 mL), under nitrogen and cooled in an ice-bath, was added cesium carbonate (2.33 g, 7.15 mmol). The reaction mixture was allowed to warm up to ambient temperature and was stirred for 4 h. The mixture was cooled in an ice-bath and water (100 mL) was added followed by ethyl acetate (100 mL). The mixture was transferred to a separatory funnel and the layers separated. The aqueous phase was extracted twice more with ethyl acetate. The combined organic layers were washed with 10% citric acid (100 mL), saturated sodium bicarbonate (100 mL) and brine (100 mL), dried and the solvent removed in vacuo. The residue was preabsorbed onto Celite then purified by silica gel DCVC. Like fractions were combined, then triturated with diethyl ether to give (S)-tert-butyl 3-[1-(3-benzyloxy)phenyl-3,6-dioxo-4-phenylpiperazine-2-yl]propanoate (4.18 g, 59%) as a colourless solid; mp 141.6-143.6° C. $^1$H NMR (400 MHz, CDCl$_3$) δ 7.48-7.29 (m, 11H), 7.03-6.95 (m, 3H), 5.08 (s, 2H), 4.55 (dd, J=17.6, 17.0 Hz, 2H), 4.45 (dd, J=9.1, 5.2 Hz, 1H), 2.52-2.14 (m, 4H), 1.37 (s, 9H). $^{13}$C NMR (50 MHz, CDCl$_3$) δ 171.4, 165.7, 163.8, 159.6, 139.9, 139.8, 136.5, 130.4, 129.3, 128.6, 128.1, 127.6, 127.4, 125.1, 119.3, 114.7, 113.7, 81.0, 70.25, 63.9, 52.9, 30.6, 28.0, 26.9. EIMS: m/z 500 [M]$^+$. HRMS calcd for $C_{31}H_{32}N_2O_5$ 500.2306, found 500.2294.

(S)-tert-Butyl 3-[1-(3-benzyloxy)phenyl-4-phenylpiperazine-2-yl]propanoate (18)

To a stirred solution of (S)-tert-butyl 3-[1-(3-benzyloxy)phenyl-3,6-dioxo-4-phenylpiperazine-2-yl]propanoate (2.97 g, 5.95 mmol) in anhydrous THF (40 mL) under nitrogen, was added borane-methylsulfide complex (7.14 mL, 14.30 mmol, 2M in THF) and the reaction allowed to stir at ambient temperature for 20 h. The reaction mixture was then cooled in an ice-bath and a solution of methanol (2 mL) in THF (8 mL) was added dropwise. The solvent was removed in vacuo, whereupon more methanol (10 mL) was added. The solvent was removed in vacuo and this procedure was repeated once more. The residue was preabsorbed onto Celite then purified by silica gel (DCVC) eluting with a gradient of ethyl acetate in PE (2%-7% ethyl acetate) to give (S)-tert-butyl 3-[1-(3-benzyloxy)phenyl-4-phenylpiperazine-2-yl]propanoate (2.08 g, 74%) as a pale yellow oil. $^1$H NMR (400 MHz, CDCl$_3$) δ 7.47-7.42 (m, 2H), 7.42-7.35 (m, 2H), 7.35-7.25 (m, 3H), 7.19-7.13 (m, 1H), 6.97-6.92 (m, 2H), 6.91-6.85 (m, 1H), 6.57-6.52 (m, 2H), 6.48-6.42 (m, 1H), 5.06 (s, 2H), 3.97-3.88 (m, 1H), 3.61-3.50 (m, 2H), 3.50-3.41 (m, 1H), 3.38-3.27 (m, 1H), 3.13-3.04 (m, 1H), 3.03-2.29 (m, 1H), 2.33-2.14 (m, 2H), 2.12-1.90 (m, 2H), 1.41 (s, 9H). $^{13}$C NMR (100 MHz, CDCl$_3$) δ 172.6, 160.1, 151.7, 151.2, 137.3, 13.0, 129.2, 128.5, 127.9, 127.6, 119.9, 116.4, 108.8, 104.5, 103.2, 80.4, 70.0, 55.2, 51.8, 48.8, 43.1, 32.7, 28.1, 22.8. EIMS: m/z 472 [M]$^+$. HRMS calcd for C$_{30}$H$_{36}$N$_2$O$_3$ 472.2720, found 472.2710.

(S)-3-[1-(3-Hydroxy)phenyl-4-phenylpiperazin-2-yl] propanoic Acid (19)

To a stirred solution of (S)-tert-butyl 3-[1-(3-benzyloxy) phenyl-4-phenylpiperazine-2-yl]propanoate (0.82 g, 1.75 mmol) in trifluoroacetic acid (3.5 mL) was added thioanisole (620 □L, 5.22 mmol) and the reaction allowed to stir at ambient temperature for 3 days. The reaction mixture was then cooled to 0° C., and water (10 mL) was slowly added followed by EtOAc (15 mL). The mixture was transferred to a separatory funnel, the layers separated and the aqueous phase extracted twice more with EtOAc, dried and the solvent removed in vacuo. The dark tan oil was preabsorbed onto Celite, then chromatographed (DCVC) eluting with a gradient of methanol in chloroform (0-5% MeOH) to give (S)-3-[1-(3-hydroxy)phenyl-4-phenylpiperazin-2-yl]propanoic acid (418 mg, 70%) as a tan foam. $^1$H NMR (400 MHz, CDCl$_3$) δ 7.37-7.31 (m, 2H), 7.30-7.24 (m, 2H), 7.17 (br s, 1H), 7.08-7.00 (m, 3H), 6.92-6.79 (m, 2H), 3.99-3.89 (m, 1H), 3.70-3.37 (m, 6H), 2.42-2.18 (m, 2H), 2.02-1.88 (m, 2H). $^{13}$C NMR (50 MHz, MeOH-d$_4$) δ 175.8, 160.6, 151.0, 144.0, 132.6, 130.6, 123.0, 118.5, 116.7, 112.7, 109.3, 63.7, 55.6, 53.7, 49.2, 30.8, 25.0. EIMS: m/z 326 [M]$^+$. HRMS calcd for C$_{19}$H$_{22}$N$_2$O$_3$ 326.1625, found 326.1620.

(S)-3-[1-(3-Benzyloxy)phenyl-4-phenylpiperazin-2-yl] propanoic acid (230 mg, 30%) was also obtained from this reaction and was isolated as a pale tan foam. $^1$H NMR (400 MHz, CDCl$_3$) δ 10.59 (br s, 1H), 7.45-7.25 (m, 8H), 7.17-6.90 (m, 6H), 5.07 (s, 2H), 3.99-3.88 (m, 1H), 3.76-3.41 (m, 6H), 2.33-2.15 (m, 2H). $^{13}$C NMR (100 MHz, CDCl$_3$) δ 176.2 160.1, 148.9, 144.3, 136.2, 131.1, 129.6, 128.7, 128.2, 127.6, 122.8, 117.8, 113.5, 112.6, 107.5, 70.3, 60.5, 52.7, 52.4, 48.9, 29.9, 23.3. EIMS: m/z 416 [M]$^+$. HRMS calcd for C$_{26}$H$_{28}$N$_2$O$_3$ 416.2094, found 416.2091.

(S)-3-[1-(3-Hydroxy)phenyl-4-phenylpiperazin-2-yl] propanamide (VB0005)

To a stirred solution of (S)-3-[1-(3-hydroxy)phenyl-4-phenylpiperazin-2-yl]propanoic acid (0.76 g, 2.32 mmol) in THF (20 mL) was added 1,1'-carbonylimidazole (0.94 g, 5.80 mmol) and the reaction stirred for 2 h. Aqueous ammonia solution (25%) (20 mL) was added and the reaction stirred for a further 3 h. The reaction mixture was transferred to a separatory funnel and the layers separated. The aqueous phase was then extracted with ethyl acetate (2×20 mL). Combined organic layers were washed with brine (20 mL), dried and concentrated in vacuo. The crude residue was passed through a short florsil column eluting with a gradient of EtOAc in PE (50-100% ethyl acetate). Like fractions were combined, dissolved in dichloromethane (20 mL) and washed with water (3×20 mL). A solid crystallised out from the wet dichloromethane. Petroleum ether 40-60° C. was added and the mixture left for 1 h. The resultant solid was collected by filtration to give racemic product (100 mg, 13%). The filtrate was concentrated to dryness to give (S)-3-[1-(3-hydroxy)phenyl-4-phenylpiperazin-2-yl]propanamide (185 mg, 21%) as a pale tan foam. $^1$H NMR (400 MHz, CDCl$_3$) δ 7.31-7.24 (m, 2H), 7.13-7.06 (m, 1H), 6.95-6.84 (m, 4H), 6.47-6.41 (m, 2H), 6.35-6.30 (m, 1H), 5.74 (br s, 1H), 5.53 (br s, 1H), 4.00-3.91 (m, 1H), 3.60-3.41 (m, 3H), 3.35-3.23 (m, 1H), 3.10-3.00 (m, 1H), 3.00-2.90 (m, 2H), 2.32-1.96 (m, 4H). $^{13}$C NMR (50 MHz, CDCl$_3$) δ 176.0, 157.3, 151.6, 151.2, 130.4, 129.2, 119.9, 116.4, 107.5, 106.3, 102.9, 54.7, 51.7, 48.8, 42.9, 32.7, 23.4. EIMS: m/z 325 [M]$^+$. HRMS calcd for C$_{19}$H$_{23}$N$_3$O$_2$ 325.1790, found 325.1776. [□]$_D$=−13.5° (CHCl$_3$, c=0.005).

3-[5-(2-hydroxypropyl)-4-phenyl-imidazol-1-ylmethyl]phenol Hydrochloride (20)

A solution of 3-[5-(2-hydroxypropyl)-4-phenyl-imidazol-1-ylmethyl]phenol (14 mg, 0.05 mmol), concentrated hydrochloric acid (3.6 µL, 0.05 mmol) and methanol (1 mL) was allowed to stir at ambient temperature for 20 min. The solvent was then removed in vacuo; the residue was then taken up in diethyl ether (2 mL), the solvent removed under reduced pressure and the procedure repeated. The resulting white foam was dried in vacuo at 35° C., dissolved in water (10 mL), filtered through a plug of glass filter paper and freeze-dried to afford 3-[5-(2-hydroxypropyl)-4-phenyl-imidazol-1-ylmethyl]phenol hydrochloride as a fluffy white solid; mp 84-88° C. $^1$H NMR (400 MHz, CD$_3$OD) δ 8.84 (s, 1H), 7.63 (m, 2H), 7.53 (m, 3H), 7.25 (m, 1H), 6.81 (m, 1H), 6.77 (d, 1H, J=8.0 Hz), 6.70 (s, 1H), 5.53 (d, 1H, J=16.0 Hz), 5.48 (d, 1H, J=16.0 Hz), 3.92 (sextet, 1H), 2.85 (d, 2H, J=8.0 Hz), 1.12 (d, 3H, J=8.0 Hz). $^{13}$C NMR (125 MHz, CD$_3$OD) δ 159.8, 136.9, 136.3, 133.3, 131.8, 131.0, 130.5, 130.4, 129.7, 129.0, 119.8, 117.0, 115.7, 67.9, 52.3, 33.3, 23.8.

The synthesis schemes, processes and reagents for the production of other compounds of the present invention will be readily apparent to the skilled addressee based on the above information, commercially-available reagents and routine knowledge in the field of organic chemistry and compound synthesis.

Example 2—In Vivo Experiments

Fourteen week old spontaneous hypertensive rats (SHR; Australian Animal Resources Centre, WA) on a 2.2% salt diet (Glenn Forrest Stockfeeders, WA) were randomized to the following treatment groups: 14-week control, or VB0002 infusion (20 pmol/kg/min in 20% DMSO) or vehicle control infusion (20% DMSO) for 4 weeks. VB0002 and vehicle control infusions were via Alzet osmotic minipump, which was inserted under general anaesthesia (Isoflurane 3% in oxygen) at 14 weeks.

Fourteen week old spontaneous hypertensive rats on a 2.2% salt diet were also randomized to the following treatment groups: 14-week control, or VB0003 administration (10, 100 or 500 pmol/kg/min in 5% ethanol), VB0005 administration (100 pmol/kg/min in 5% ethanol) or drinking solution (5% ethanol) administration for 4 weeks.

The 14-week control group were anaesthetized using isoflurane (3%) delivered in oxygen, then had blood sampled and hearts and kidneys harvested for quantitation of fibrosis. The remaining groups were weighed and had blood pressure measured by tail cuff plethysmography (ADI Instruments) twice weekly for a further 4 weeks. After 4 weeks treatment, rats were anaesthetized and samples collected as per the 14-week control group. Results are mean±sem for n=5 rats per group.

For quantitation of fibrosis, tissue slices ≤3 mm thick were fixed in 10% buffered formalin for 24 hours, processed and embedded in paraffin. Three μm transverse sections were stained using Masson's Trichrome. A minimum of 20 random fields at 40× magnification from transverse sections (5 at each of 2 levels) were digitized. The degree of fibrosis was determined as a percent of field area of each digitized image using Image-Pro Plus V.5 (Media Cybernetics, Bethesda, Md., USA), and then averaged to determine the level of fibrosis for each rat.

Figure 8:
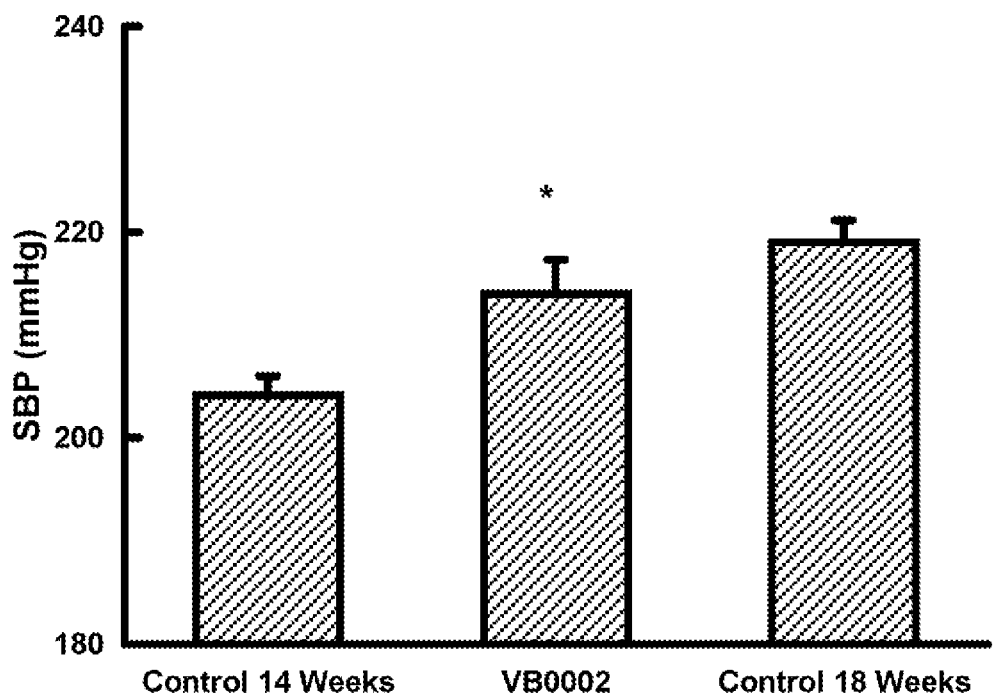
FIG. 8: Systolic blood pressure in SHR on a 2.2% salt diet with VB0002 (in 20% DMSO) at a dose of 20 pmol/kg/min or vehicle control (20% DMSO) administered intravenously via osmotic minipump for 4 weeks. * p<0.005 vs 18 week control.
Figure 9:
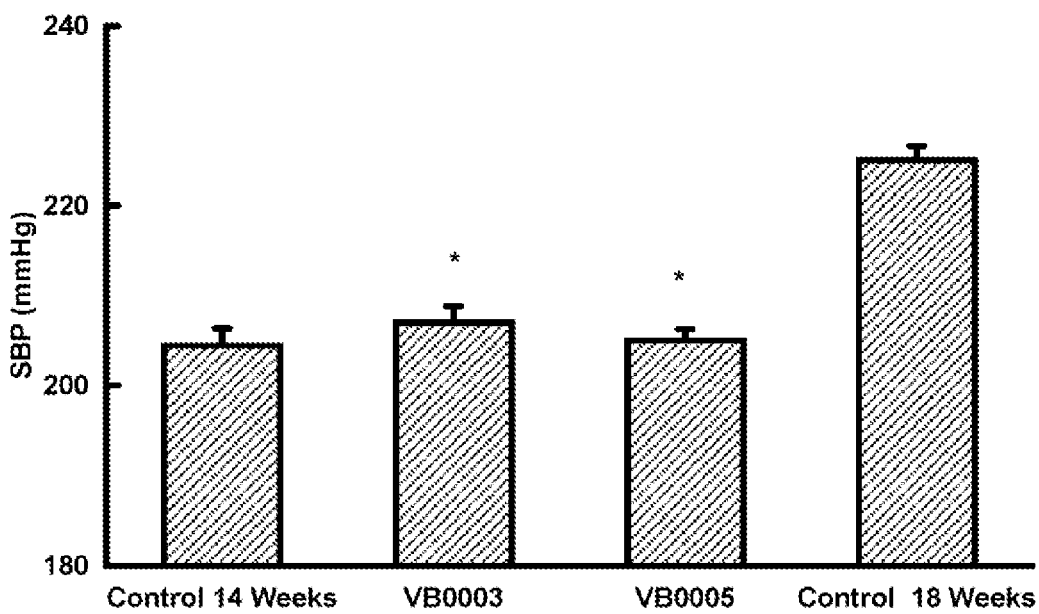
FIG. 9: Systolic blood pressure in SHR on a 2.2% salt diet with VB0003 (in 5% ethanol) at a dose of 20 pmol/kg/min, VB0005 (in 5% ethanol) at a dose of 20 pmol/kg/min or vehicle control (5% ethanol) administered in the drinking solution for 4 weeks. * p<0.0005 vs 18 week control.

Systolic blood pressure in rats treated with VB0002, VB0003 and VB0005 was reduced compared to 18 week controls (FIGS. 8 and 9), showing that these compounds are effective in lowering blood pressure.

Figure 10:
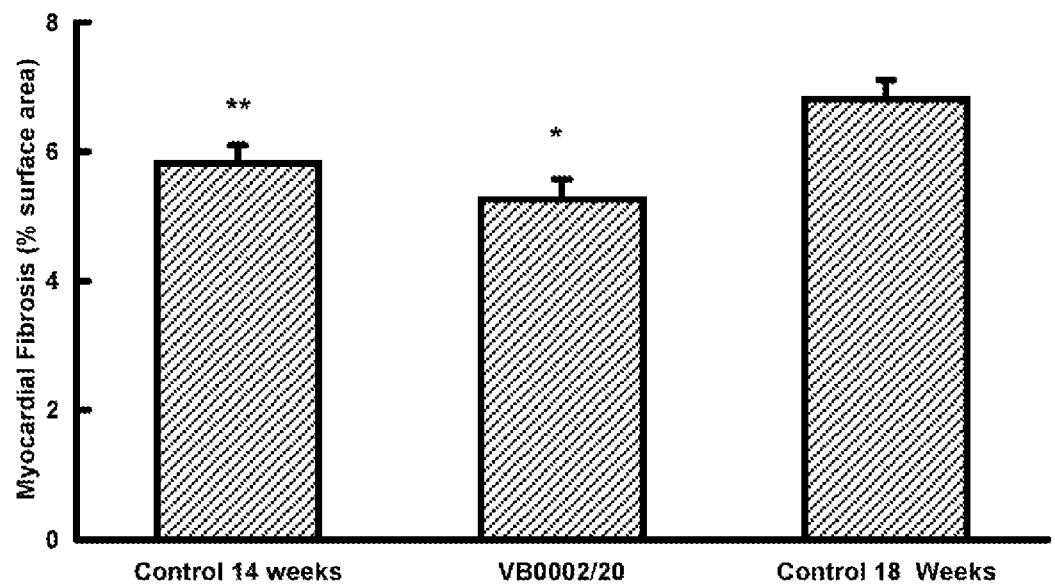
FIG. 10: Myocardial fibrosis in SHR on a 2.2% salt diet with VB0002 (in 20% DMSO) at a dose of 20 pmol/kg/min or vehicle control (20% DMSO) administered intravenously via an osmotic minipump for 4 weeks. * p<0.005 vs 18 week control, ** p<0.0005 vs 18 week control.

Myocardial fibrosis in rats treated with VB0002 at 20 pmol/kg/min was reduced compared to 14 week controls and 18 week controls (FIG. 10), showing that this compound reduces the development of myocardial fibrosis and reverses established myocardial fibrosis.

Figure 11:
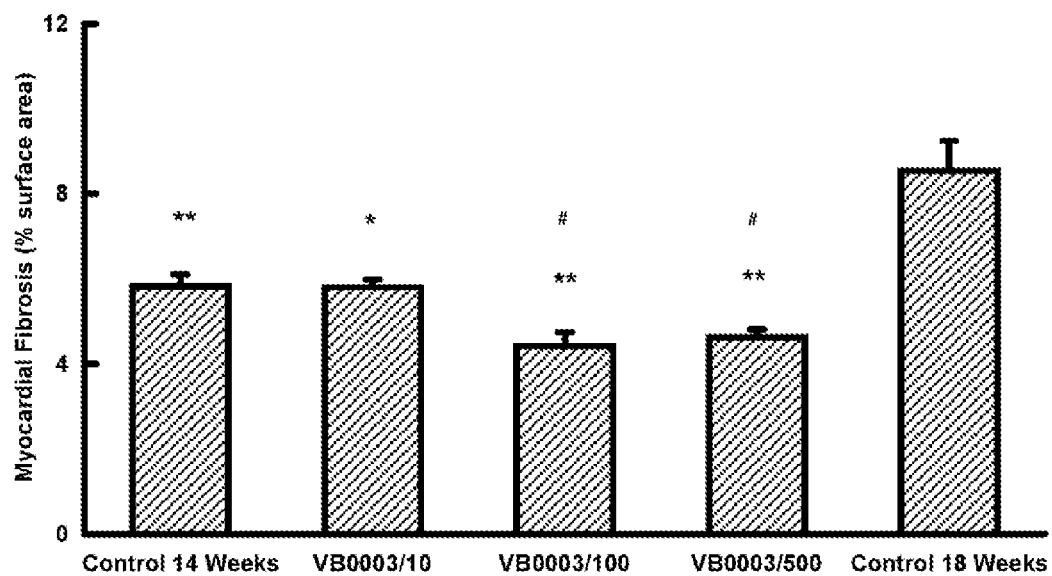
FIG. 11: Myocardial fibrosis in SHR on a 2.2% salt diet with VB0003 (in 5% ethanol) at dosages of 10, 100 and 500 pmol/kg/min or vehicle control (5% ethanol) administered in the drinking solution for 4 weeks. * p<0.005 vs 18 week control, ** p<0.0005 vs 18 week control, #p<0.01 vs 14 week control.

Myocardial fibrosis in rats treated with VB0003 at 10, 100 and 500 pmol/kg/min was reduced compared to 18 week controls (FIG. 11), showing that these compounds reduce the development of myocardial fibrosis. Myocardial fibrosis in rats treated with VB0003 at 100 and 500 pmol/kg/min was reduced compared to 14 week controls (FIG. 11), showing that these dosages of the compound reverse established myocardial fibrosis.

Figure 12:
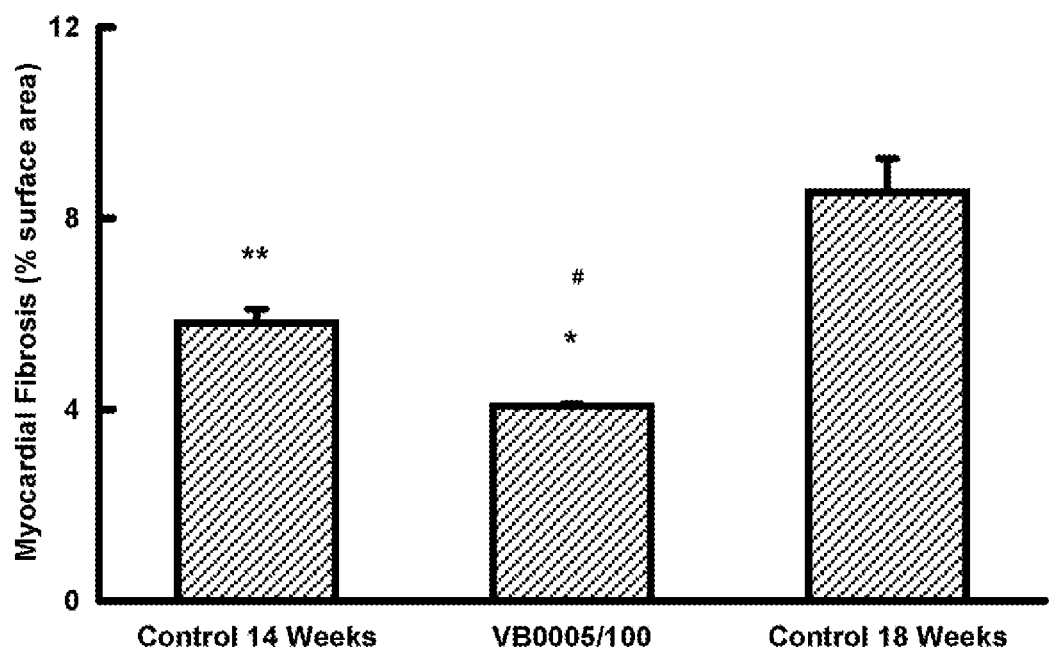
FIG. 12: Myocardial fibrosis in SHR on a 2.2% salt diet with VB0005 (in 5% ethanol) at a dosage of 100 pmol/kg/min or vehicle control (5% ethanol) administered in the drinking solution for 4 weeks. * p<0.001 vs 18 week control, ** p<0.0005 vs 18 week control, #p<0.01 vs 14 week control.

Myocardial fibrosis in rats treated with VB0005 at 100 pmol/kg/min was reduced compared to 14 week controls and 18 week controls (FIG. 10), showing that this compound reduces the development of myocardial fibrosis and reverses established myocardial fibrosis (FIG. 12).

The claims defining the invention are as follows:
1. A compound of the formulae:

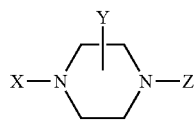

wherein:
X is selected from the group consisting of:

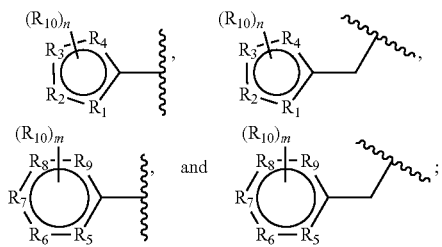

$R_1$ to $R_9$ are independently C, N, O or S;
$R_{10}$ is independently selected from $C_{1-6}$alkyl, halo, $C_{0-6}$alkyl carboxylic acid, amino, hydroxy and $C_{1-6}$alkoxy;
Y is A, $CH_2$-A or CH=A;

A is selected from

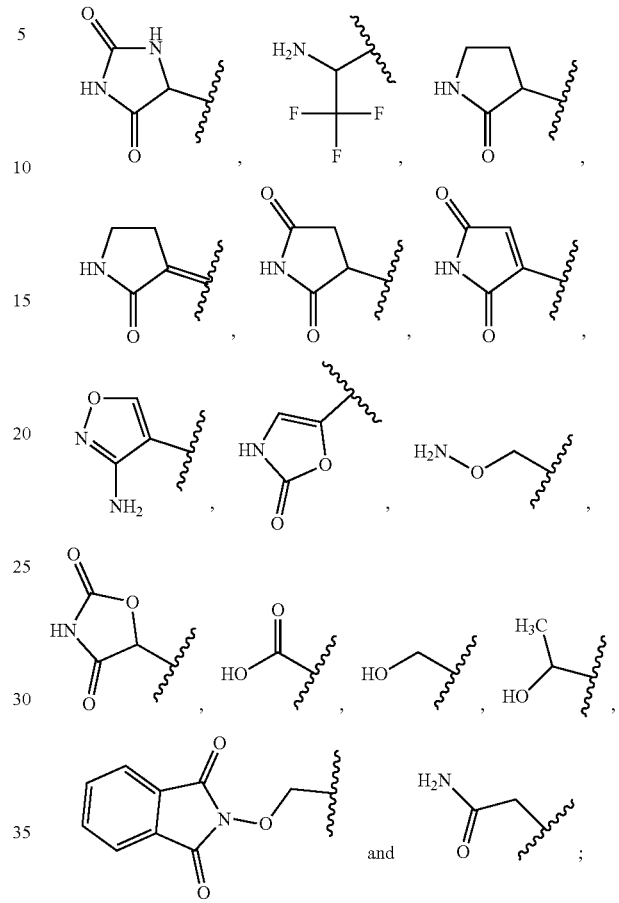

Z is selected from the group consisting of:

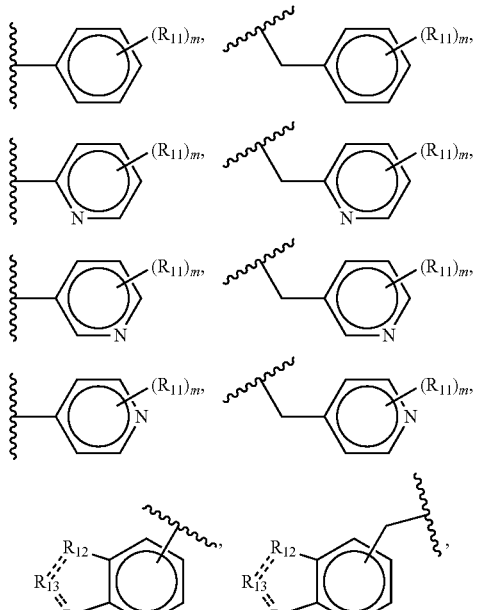

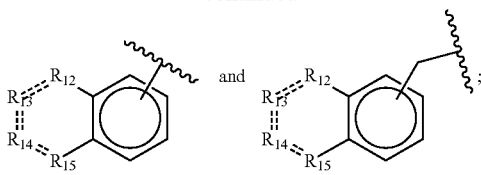

$R_{11}$ is independently selected from halo, alkyl, hydroxy, amino and substituted amino;

$R_{12}$, $R_{14}$ and $R_{15}$ are independently C, CH, CH$_2$, O, N, NH or S;

$R_{13}$ is C, CH, CH$_2$, N, NH, C—CF$_3$, CH—CF$_3$ or C=O;

m is 0, 1, 2, 3, 4 or 5; and n is 0, 1, 2, 3 or 4, or a stereoisomer or pharmaceutically acceptable salt thereof.

2. The compound, or a stereoisomer or pharmaceutically acceptable salt thereof, according to claim 1 wherein $R_{10}$ is independently selected from —CH$_3$, —C(O)OH, —F, —NH$_2$, —OH and —OCH$_3$.

3. The compound, or a stereoisomer or pharmaceutically acceptable salt thereof, according to claim 1, wherein $R_5$ to $R_9$ are independently C or N.

4. The compound, or a stereoisomer or pharmaceutically acceptable salt thereof, according to claim 1, wherein the $C_{0-6}$alkyl carboxylic acid is carboxylic acid.

5. The compound, or a stereoisomer or pharmaceutically acceptable salt thereof, according to claim 1, wherein $R_{11}$ is halo selected from the group consisting of F, Cl, Br and I.

6. The compound, or a stereoisomer or pharmaceutically acceptable salt thereof, according to claim 1, wherein Ru is substituted amino of the formula —NHR$_{16}$ and wherein:

$R_{16}$ is selected from —CN, —SO$_2$(R$_{17}$)$_a$R$_{18}$ and —CO(R$_{17}$)$_a$R$_{18}$, a is 0 or 1, $R_{17}$ is selected from —NH— and —O—, and $R_{18}$ is selected from —H, —CH$_3$, —CH$_2$CH$_3$, —CH$_2$OH and —CH$_2$CH$_2$OH.

7. The compound, or a stereoisomer or pharmaceutically acceptable salt thereof, according to claim 1, wherein Ru is substituted amino selected from the group consisting of —NHSO$_2$CH$_3$, —NHCOH, —NHCONHCH$_3$, —NHCONHCH$_2$CH$_3$, —NHSO$_2$NHCH$_3$, —NHSO$_2$NHCH$_2$CH$_3$, —NHCOCH$_3$, —NHCOOCH$_3$, —NHCOOCH$_2$CH$_2$OH, —NHCONH$_2$, and —NHCN.

8. The compound, or a stereoisomer or pharmaceutically acceptable salt thereof, according to claim 1, wherein $R_{11}$ is alkyl selected from the group consisting of methyl, ethyl, propyl, butyl and pentyl.

9. The compound, or a stereoisomer or pharmaceutically acceptable salt thereof, according to claim 1, wherein the compound is selected from the group consisting of:

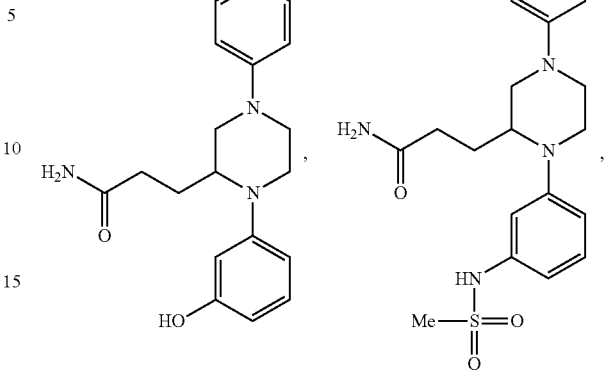

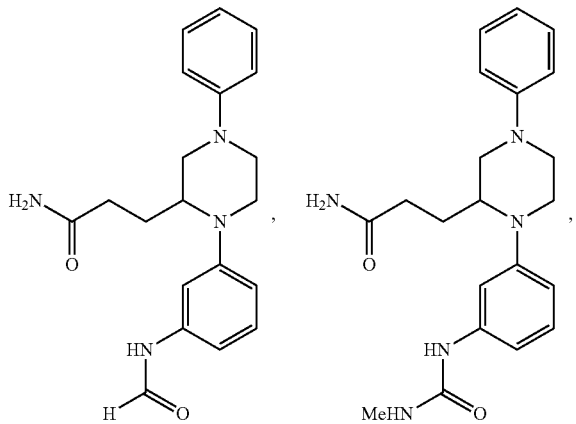

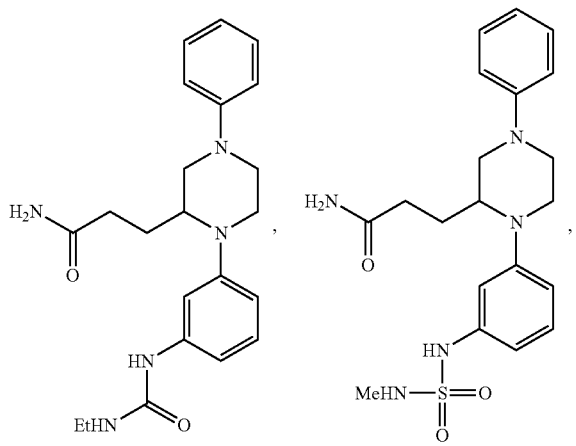

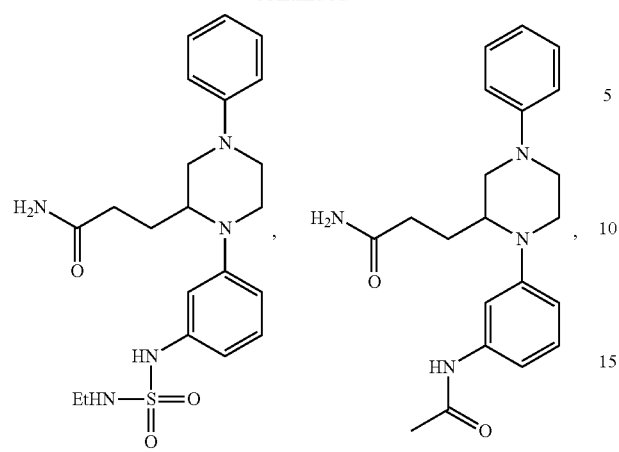
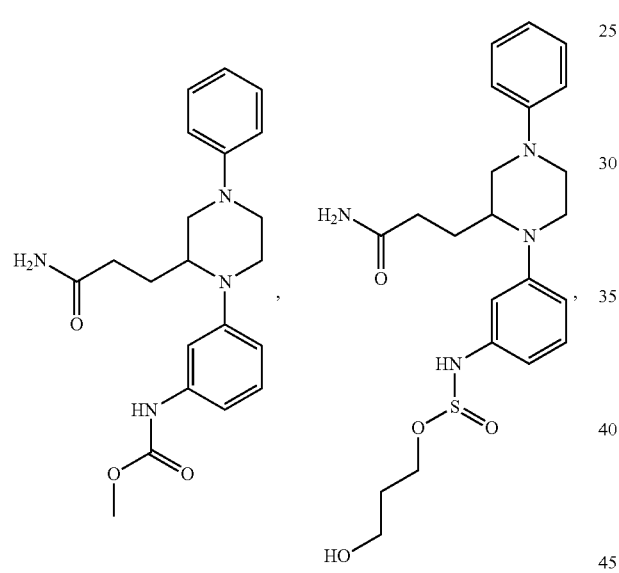
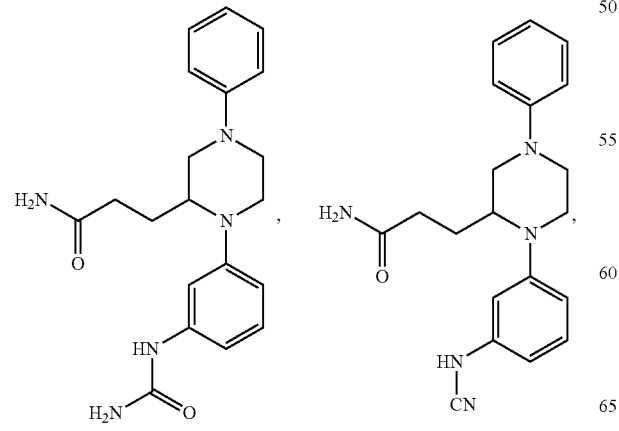
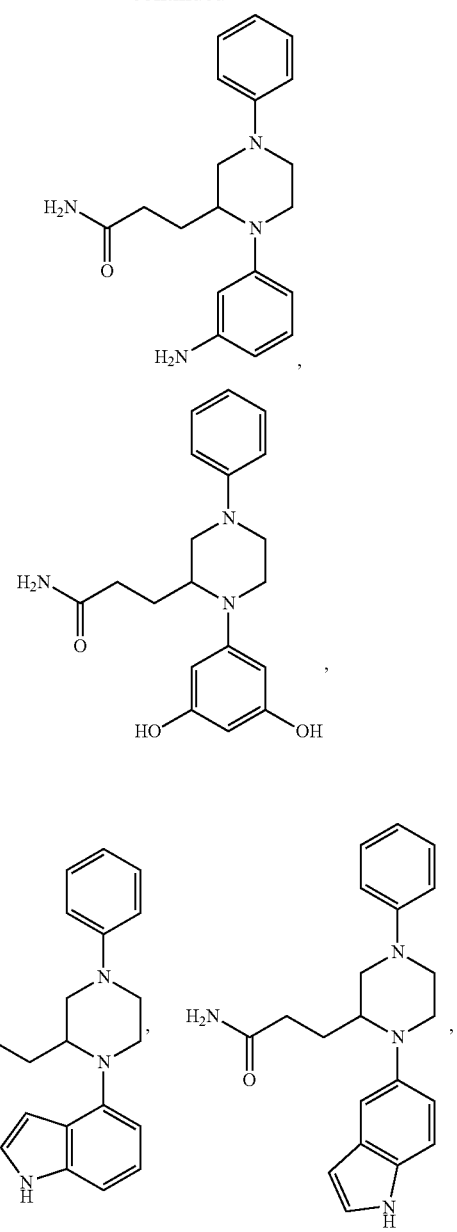
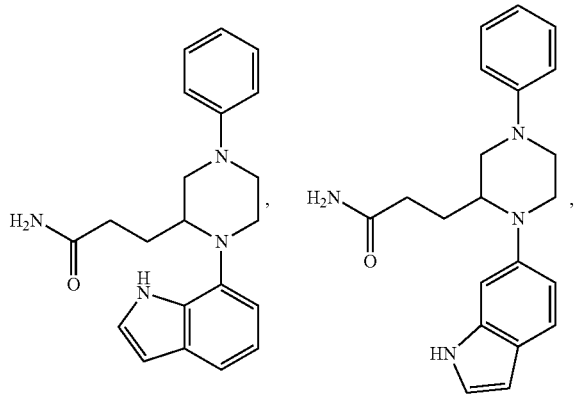

-continued
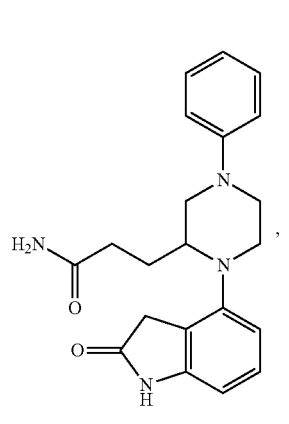 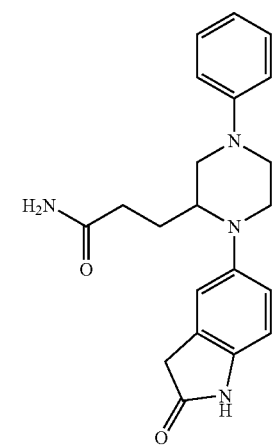 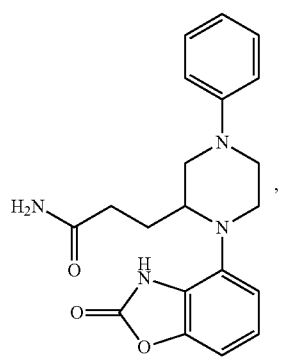 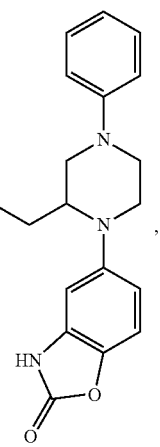
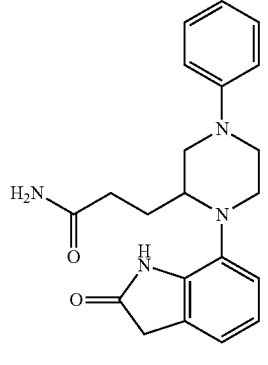 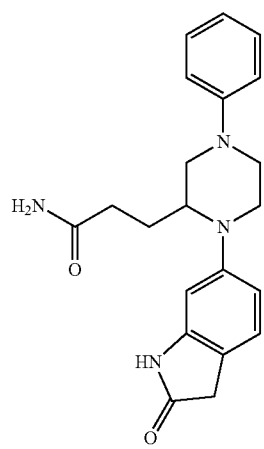 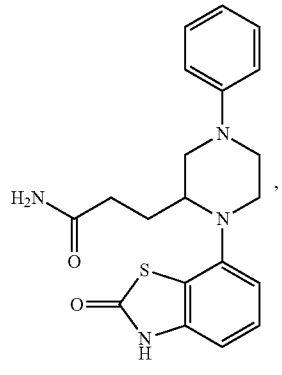 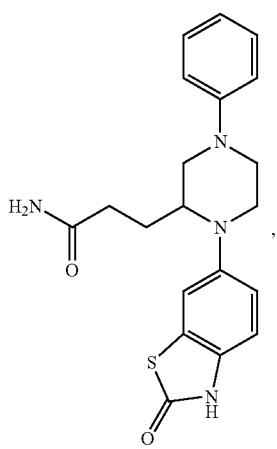
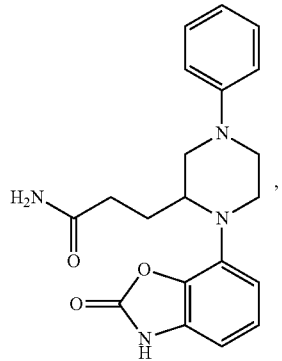 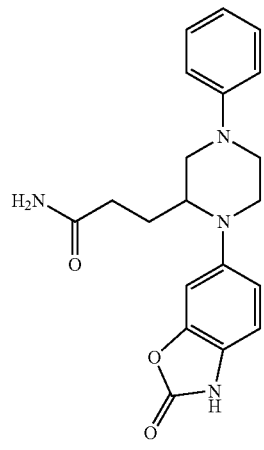 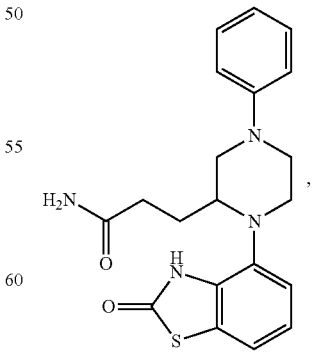 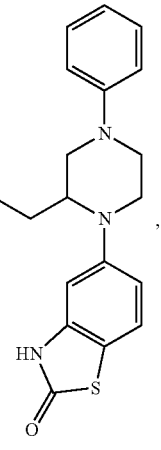

123
-continued
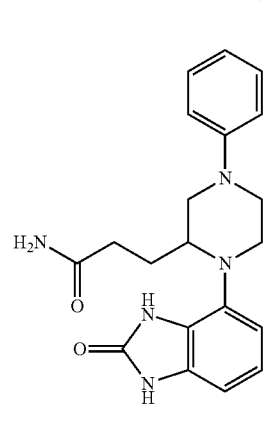
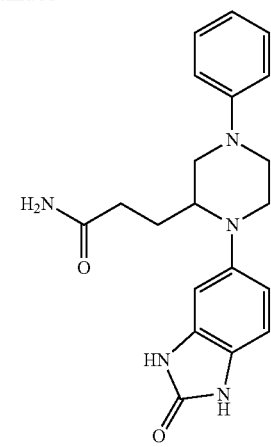
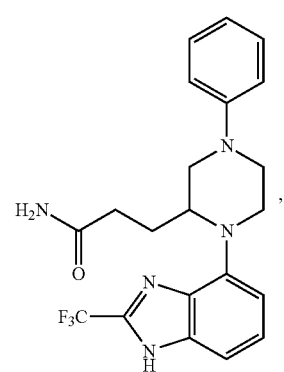
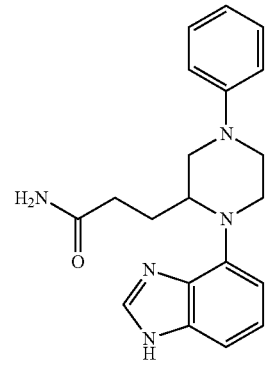
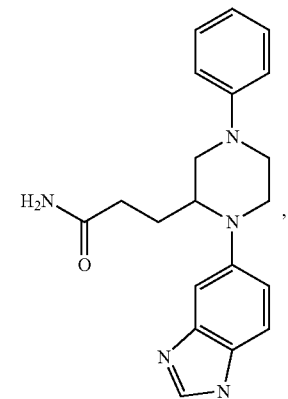
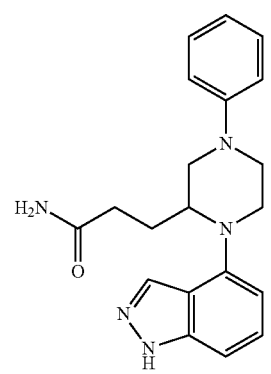
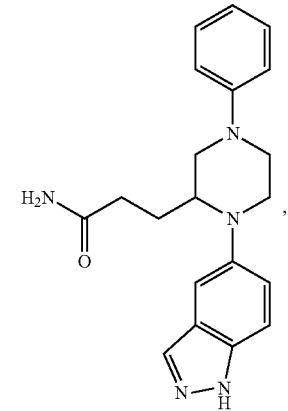
124
-continued
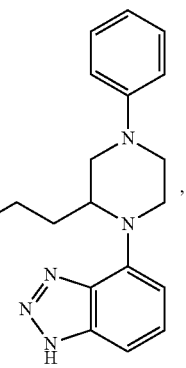
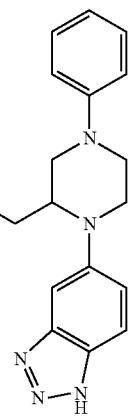
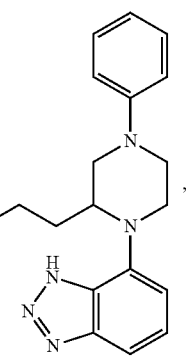
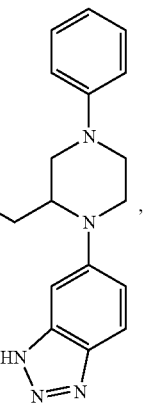
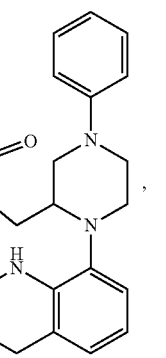
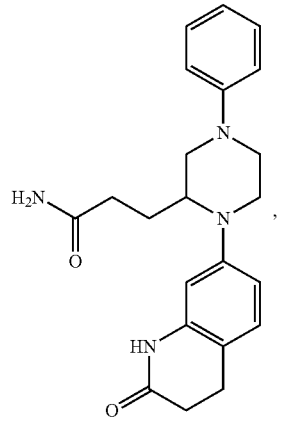
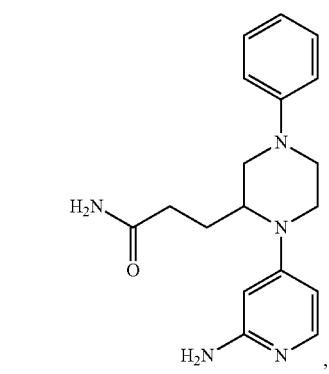

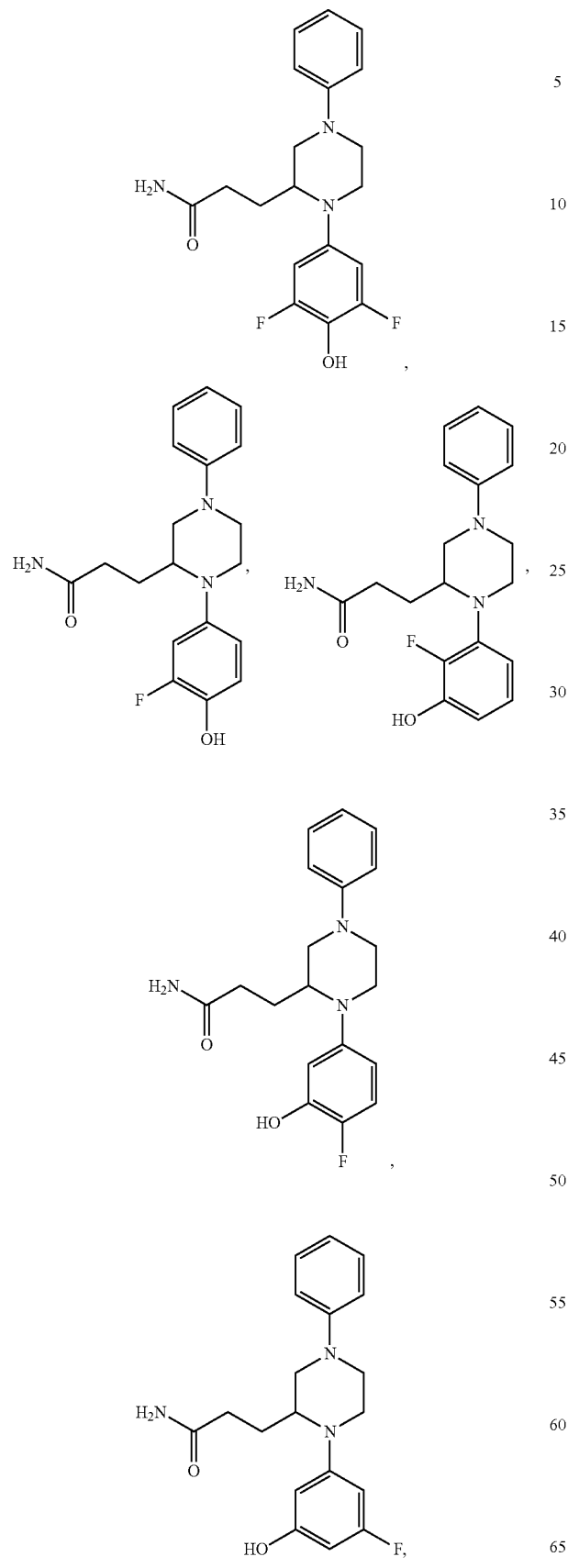
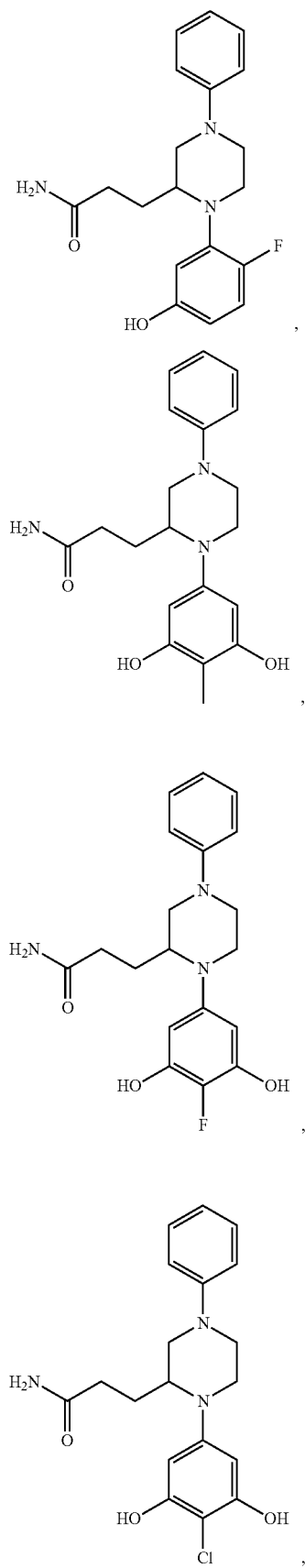

127 -continued
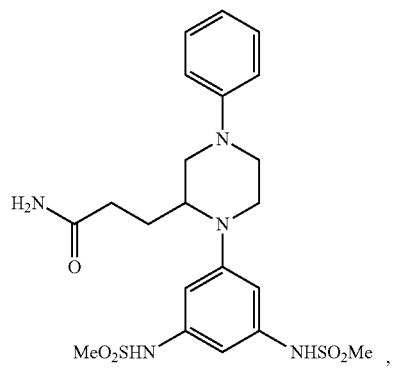
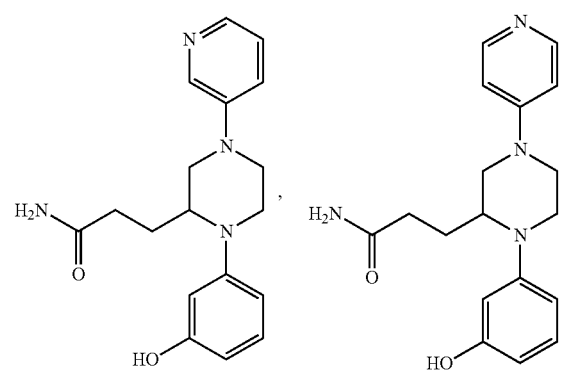
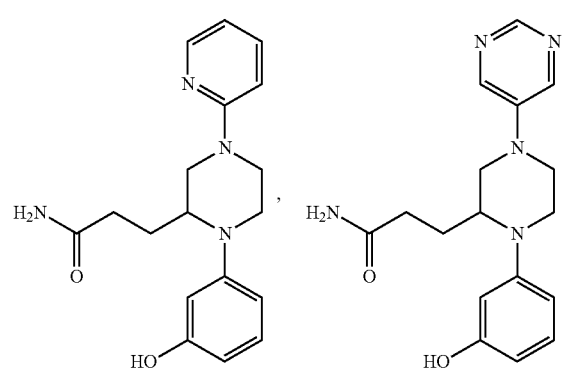
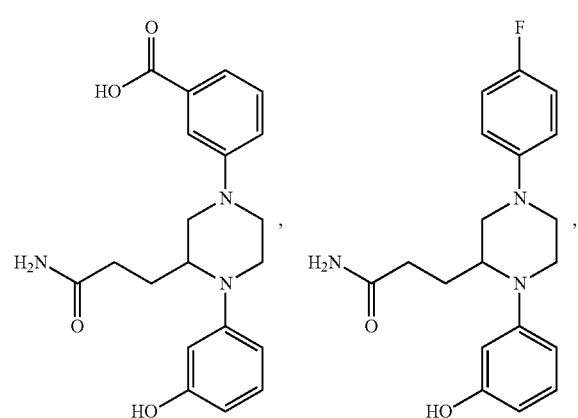
128 -continued
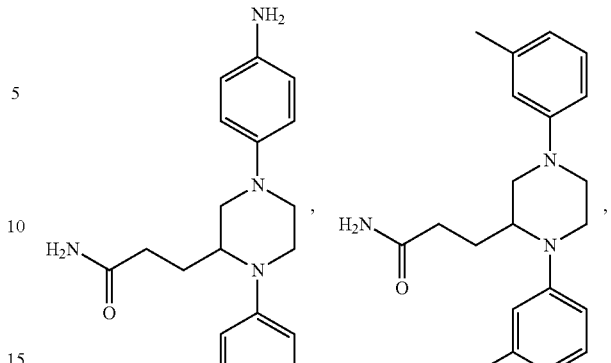
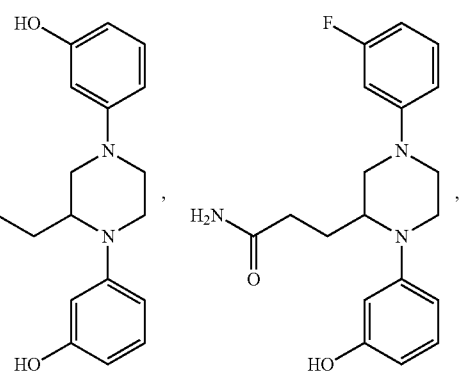
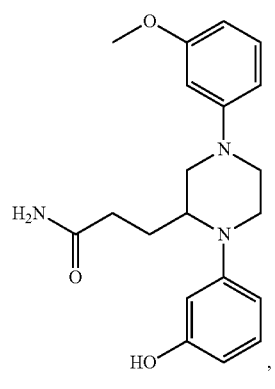
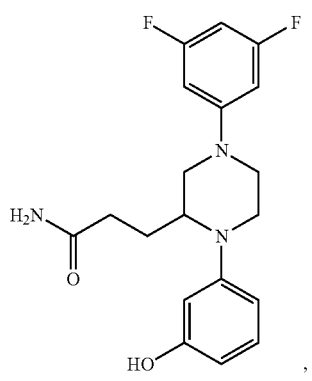

129
-continued
130
-continued
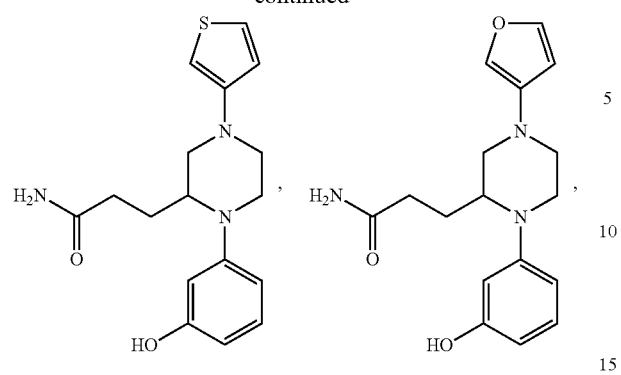
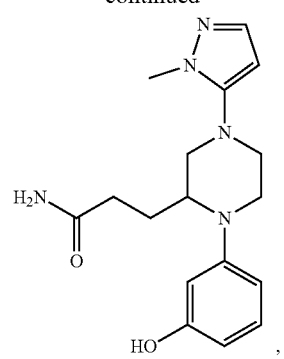
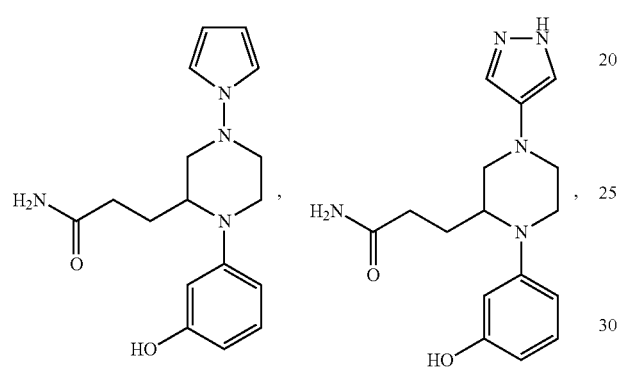
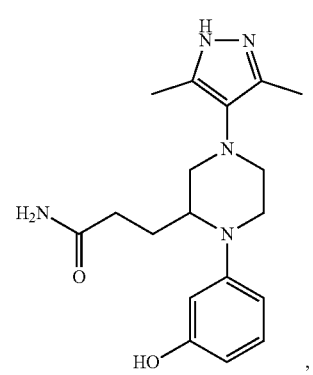
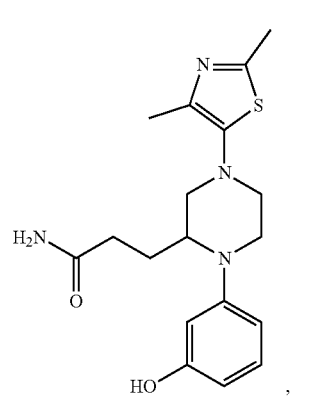
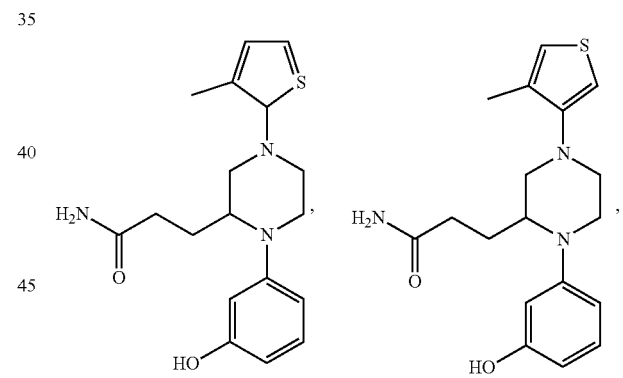
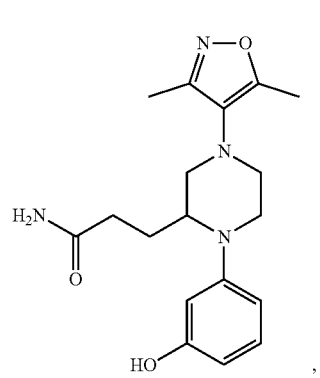
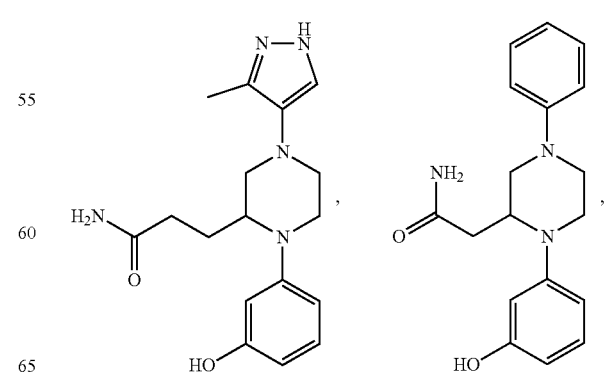

131
-continued
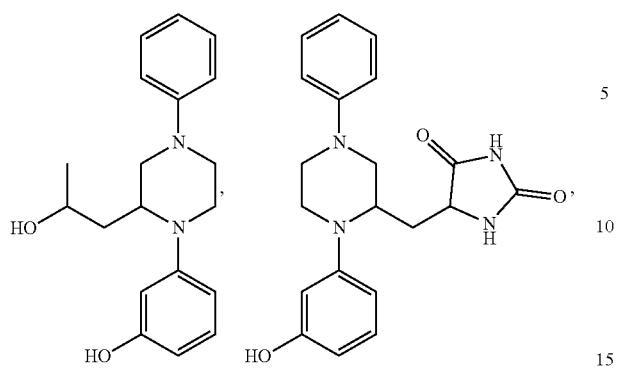
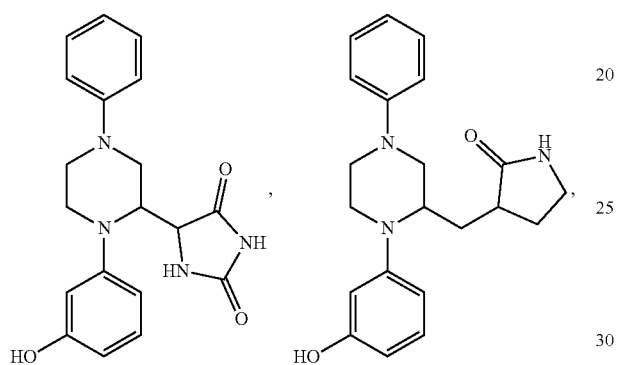
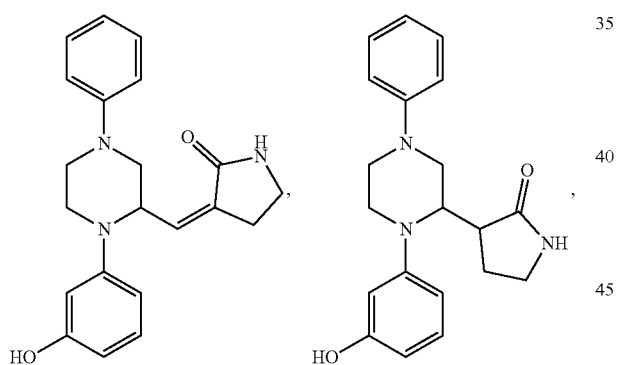
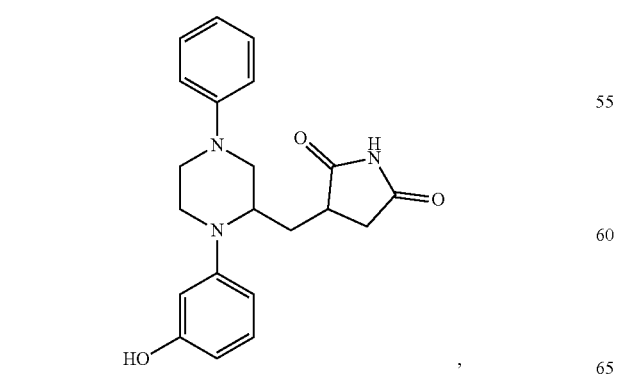
132
-continued
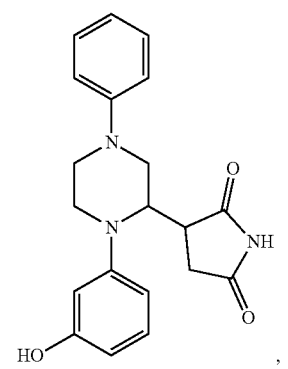
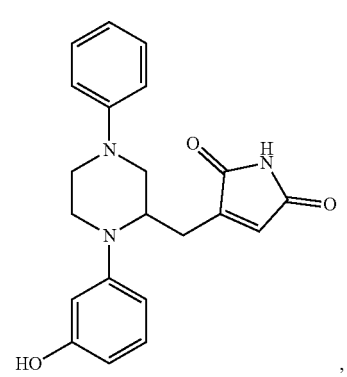
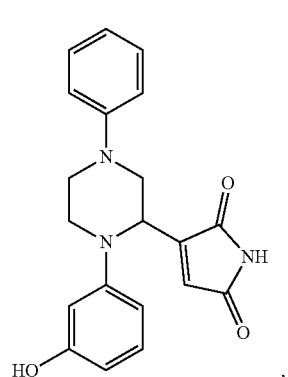
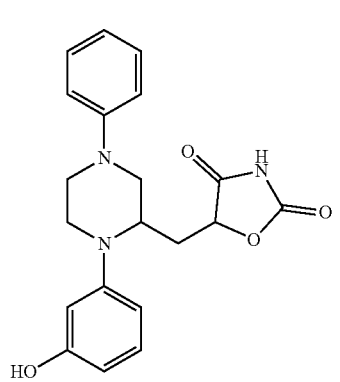

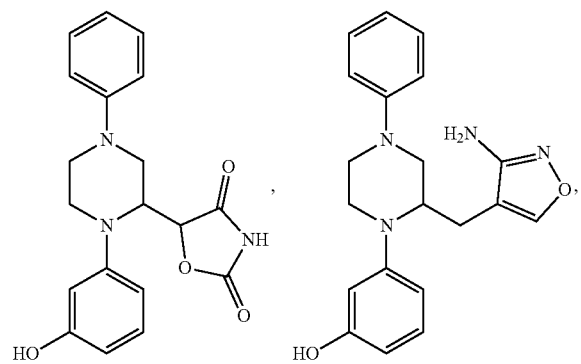
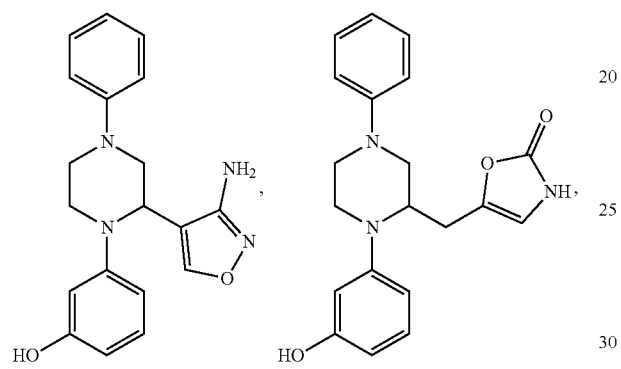
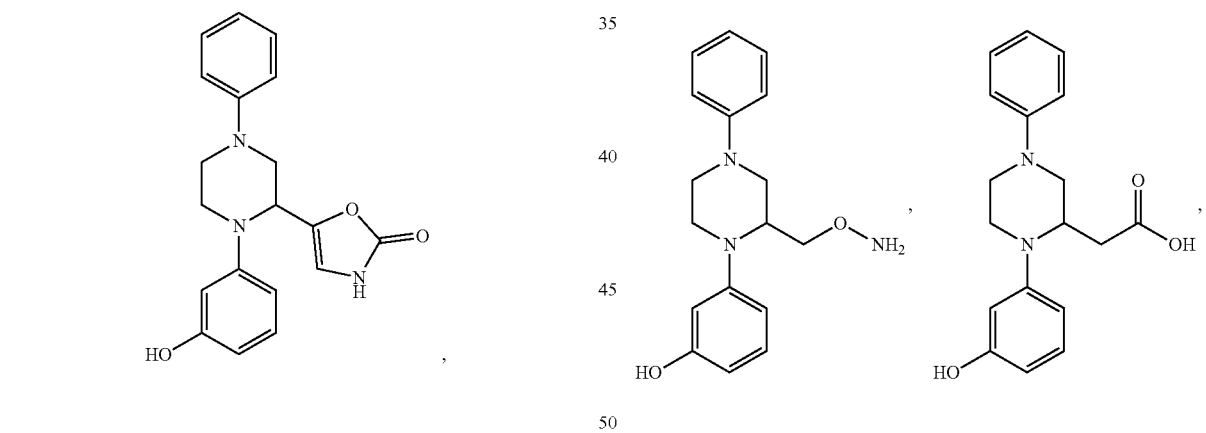
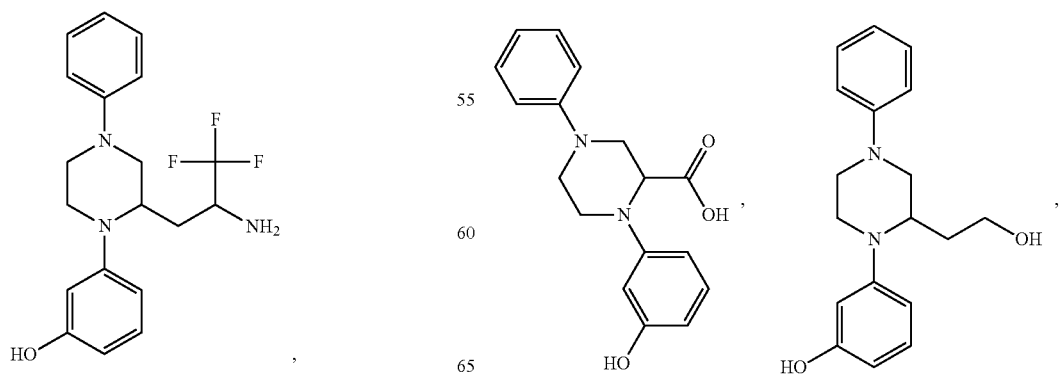
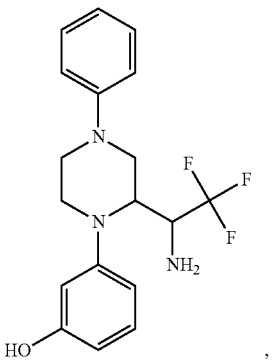
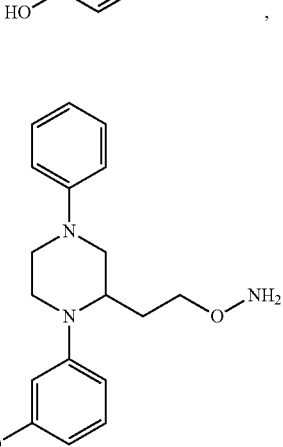
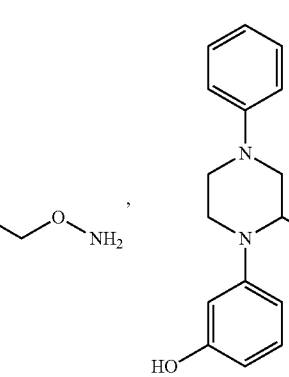
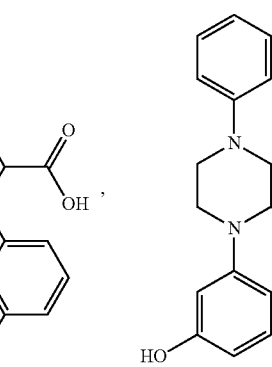

-continued

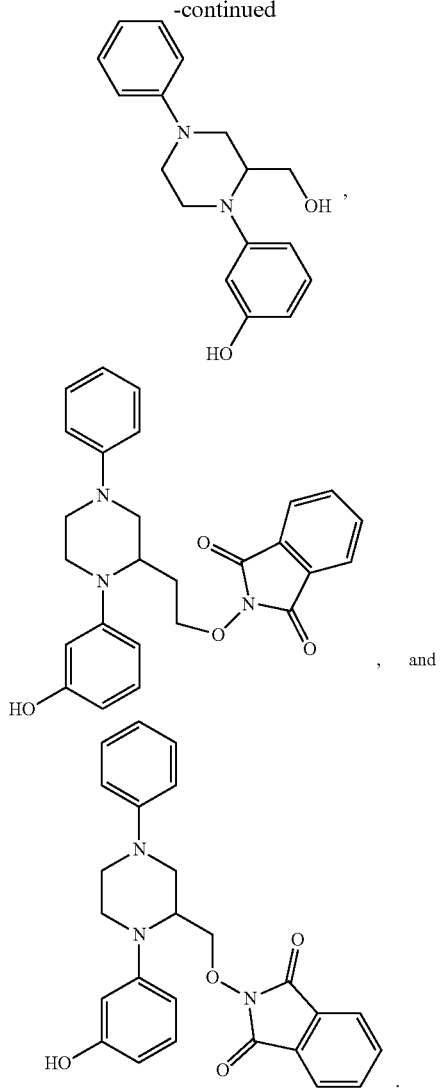

, and

10. The compound, or a stereoisomer or pharmaceutically acceptable salt thereof, according to claim 1, wherein the compound is

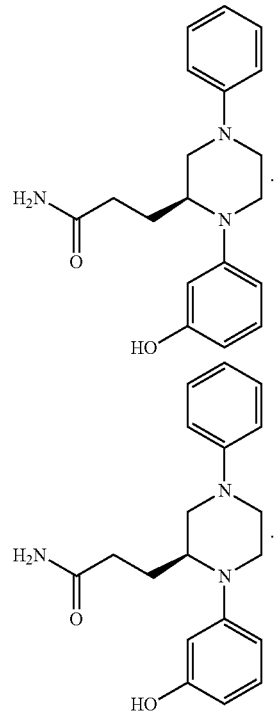

11. A pharmaceutical composition comprising a compound, or a stereoisomer or pharmaceutically acceptable salt thereof, according to claim 1 and a pharmaceutically-acceptable excipient.

12. A method for the therapeutic treatment of: hypertension or prehypertension in a subject; or
fibrosis in a subject; or
hypertension and fibrosis in a subject; or prehypertension and fibrosis in a subject,
the method comprising administering to the subject a compound, or a stereoisomer or pharmaceutically acceptable salt thereof, according to claim 1.

13. The method according to claim 12 wherein the fibrosis selected from myocardial fibrosis, kidney fibrosis, liver fibrosis and lung fibrosis.

\* \* \* \* \*